(12) United States Patent
Ohashi et al.

(10) Patent No.: US 8,057,985 B2
(45) Date of Patent: Nov. 15, 2011

(54) POLYMERIZABLE ANION-CONTAINING SULFONIUM SALT AND POLYMER, RESIST COMPOSITION, AND PATTERNING PROCESS

(75) Inventors: Masaki Ohashi, Joetsu (JP); Takeshi Kinsho, Joetsu (JP); Youichi Ohsawa, Joetsu (JP); Jun Hatakeyama, Joetsu (JP); Seiichiro Tachibana, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 315 days.

(21) Appl. No.: 12/549,191

(22) Filed: Aug. 27, 2009

(65) Prior Publication Data
US 2010/0055608 A1 Mar. 4, 2010

(30) Foreign Application Priority Data

Aug. 28, 2008 (JP) ................................ 2008-219475

(51) Int. Cl.
G03F 7/038 (2006.01)
G03F 7/039 (2006.01)
G03F 7/20 (2006.01)
G03F 7/30 (2006.01)

(52) U.S. Cl. ...................... 430/270.1; 430/325; 430/326; 430/330; 430/907; 430/910; 430/921; 430/923; 430/925; 430/942; 562/108; 562/109; 562/110; 562/111; 562/113; 526/243; 526/245; 526/287

(58) Field of Classification Search ......................... None
See application file for complete search history.

(56) References Cited

U.S. PATENT DOCUMENTS

| | | |
|---|---|---|
| 5,580,702 A | 12/1996 | Hayase et al. |
| 5,650,483 A | 7/1997 | Malik et al. |
| 5,945,250 A | 8/1999 | Aoai et al. |
| 6,048,672 A | 4/2000 | Cameron et al. |
| 6,312,867 B1 | 11/2001 | Kinsho et al. |
| 6,746,817 B2 | 6/2004 | Takeda et al. |
| 6,830,866 B2 | 12/2004 | Kobayashi et al. |
| 6,849,374 B2 | 2/2005 | Cameron et al. |
| 7,288,359 B2 | 10/2007 | Iwasawa et al. |
| 7,449,573 B2 | 11/2008 | Kodama et al. |
| 7,569,326 B2 * | 8/2009 | Ohsawa et al. ............ 430/270.1 |
| 2002/0197558 A1 | 12/2002 | Ferreira et al. |
| 2003/0113659 A1 | 6/2003 | Hatakeyama et al. |
| 2004/0260031 A1 | 12/2004 | Takeda et al. |
| 2007/0003871 A1 | 1/2007 | Kodama et al. |
| 2007/0149702 A1 | 6/2007 | Ando et al. |
| 2007/0231738 A1 | 10/2007 | Kaneko et al. |
| 2008/0026331 A1 | 1/2008 | Hasegawa et al. |
| 2008/0102407 A1 | 5/2008 | Ohsawa et al. |
| 2009/0069521 A1 | 3/2009 | Nagai et al. |

FOREIGN PATENT DOCUMENTS

| | | |
|---|---|---|
| EP | 0 473 547 A1 | 3/1992 |
| JP | 4-230645 A | 8/1992 |
| JP | 11-282168 A | 10/1999 |
| JP | 2000-122296 A | 4/2000 |
| JP | 2000-336121 A | 12/2000 |
| JP | 3238465 B2 | 12/2001 |
| JP | 2002-214774 A | 7/2002 |
| JP | 2003-66612 A | 3/2003 |
| JP | 2003-140332 A | 5/2003 |
| JP | 2004-2252 A | 1/2004 |
| JP | 2004-115630 A | 4/2004 |
| JP | 2004-531749 A | 10/2004 |
| JP | 2005-8766 A | 1/2005 |
| JP | 3613491 B2 | 1/2005 |
| JP | 2005-84365 A | 3/2005 |
| JP | 2005-266766 A | 9/2005 |
| JP | 2006-178317 A | 7/2006 |
| JP | 3796560 B2 | 7/2006 |
| JP | 3865048 B2 | 1/2007 |
| JP | 2007-197718 A | 8/2007 |
| JP | 2007-297590 A | 11/2007 |
| JP | 2008-31298 A | 2/2008 |
| JP | 2008-133448 A | 6/2008 |
| WO | WO-2006/121096 A1 | 11/2006 |

OTHER PUBLICATIONS

Ralph R. Dammel et al., "193 nm Immersion Lithography—Taking the Plunge", Journal of Photopolymer Science and Technology, vol. 17, No. 4, pp. 587-601, 2004.

(Continued)

*Primary Examiner* — Sin J. Lee
(74) *Attorney, Agent, or Firm* — Birch, Stewart, Kolasch & Birch, LLP

(57) ABSTRACT

A polymerizable anion-containing sulfonium salt having formula (1) is provided wherein $R^1$ is H, F, methyl or trifluoromethyl, $R^2$, $R^3$ and $R^4$ are $C_1$-$C_{10}$ alkyl, alkenyl or oxoalkyl or $C_6$-$C_{18}$ aryl, aralkyl or aryloxoalkyl, or two of $R^2$, $R^3$ and $R^4$ may bond together to form a ring with S, A is a $C_1$-$C_{20}$ organic group, and n is 0 or 1. The sulfonium salt generates a very strong sulfonic acid upon exposure to high-energy radiation. A resist composition comprising a polymer derived from the sulfonium salt is also provided.

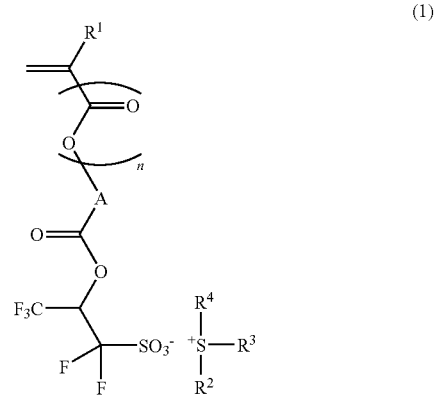

(1)

11 Claims, 15 Drawing Sheets

OTHER PUBLICATIONS

Cheng-Ping Qian et al., "Perfluoro-Enolate Chemistry: Facile Generation and Unique Reactivities of Metal F-1-Propen-2-Olates", Tetrahedron Letters, vol. 29, No. 33, pp. 4119-4122, 1988.

Koji Arimitsu et al., "Sensitivity Enhancement of Chemical-Amplification-Type Photoimaging Materials by Acetoacetic Acid Derivatives", Journal of Photopolymer Science and Technology, vol. 8, No. 1, pp. 43-44, 1995.

Kazuaki Kudo et al., "Enhancement of the Senesitivity of Chemical-Amplification-Type Photoimaging Materials by β-Tosyloxyketone Acetals", Journal of Photopolymer Science and Technology, vol. 8, No. 1, pp. 45-46, 1995.

Koji Arimitsu et al., "Effect of Phenolic Hydroxyl Residues on the Improvement of Acid-Proliferation-Type Photoimaging Materials", Journal of Photopolymer Science and Technology, vol. 9, No. 1, pp. 29-30, 1996.

* cited by examiner

POLYMERIZABLE ANION-CONTAINING SULFONIUM SALT AND POLYMER, RESIST COMPOSITION, AND PATTERNING PROCESS

CROSS-REFERENCE TO RELATED APPLICATION

This non-provisional application claims priority under 35 U.S.C. §119(a) on Patent Application No. 2008-219475 filed in Japan on Aug. 28, 2008, the entire contents of which are hereby incorporated by reference.

TECHNICAL FIELD

This invention relates to (1) a polymerizable anion-containing sulfonium salt useful as a photoacid generator or a monomer to sulfonic acid polymer, (2) a polymer derived from the sulfonium salt monomer and capable of generating a sulfonic acid in response to high-energy radiation or heat, (3) a resist composition comprising the polymer, and (4) a patterning process using the resist composition.

BACKGROUND ART

While a number of recent efforts are being made to achieve a finer pattern rule in the drive for higher integration and operating speeds in LSI devices, DUV and VUV lithography is thought to hold particular promise as the next generation in microfabrication technology. In particular, photolithography using an ArF excimer laser as the light source is thought requisite to the micropatterning technique capable of achieving a feature size of 0.13 µm or less.

The ArF lithography started partial use from the fabrication of 130-nm node devices and became the main lithography since 90-nm node devices. Although lithography using $F_2$ laser (157 nm) was initially thought promising as the next lithography for 45-nm node devices, its development was retarded by several problems. A highlight was suddenly placed on the ArF immersion lithography that introduces a liquid having a higher refractive index than air (e.g., water, ethylene glycol, glycerol) between the projection lens and the wafer, allowing the projection lens to be designed to a numerical aperture (NA) of 1.0 or higher and achieving a higher resolution. See Journal of Photopolymer Science and Technology, Vol. 17, No. 4, p 587 (2004).

In the photolithography using an ArF excimer laser (wavelength 193 nm) as the light source, a high sensitivity resist material capable of achieving a high resolution at a small dose of exposure is needed to prevent the degradation of precise and expensive optical system materials. Among several measures for providing high sensitivity resist material, the most common is to select each component which is highly transparent at the wavelength of 193 nm. For example, polymers of acrylic acid and derivatives thereof, norbornene-maleic anhydride alternating copolymers, polynorbornene, ring-opening metathesis polymers, and hydrogenated ring-opening metathesis polymers have been proposed as the base resin. This choice is effective to some extent in that the transparency of a resin alone is increased.

Studies have also been made on photoacid generators. In prior art chemically amplified resist compositions for lithography using KrF excimer laser, photoacid generators capable of generating alkane- or arene-sulfonic acids are used. However, the use of these photoacid generators in chemically amplified resist compositions for ArF lithography results in an insufficient acid strength to scissor acid labile groups on the resin, a failure of resolution, or a low sensitivity. Thus these photoacid generators are not suited for the fabrication of microelectronic devices.

For the above reason, photoacid generators capable of generating perfluoroalkanesulfonic acids having a high acid strength are generally used in ArF chemically amplified resist compositions. These photoacid generators capable of generating perfluoroalkanesulfonic acids have already been developed for use in the KrF resist compositions. For instance, JP-A 2000-122296 and U.S. Pat. No. 6,048,672 (or JP-A 11-282168) describe photoacid generators capable of generating perfluorohexanesulfonic acid, perfluorooctanesulfonic acid, perfluoro-4-ethylcyclohexanesulfonic acid, and perfluorobutanesulfonic acid. JP-A 2002-214774, US Patent Application Publication 2003-0113659 A1 (JP-A 2003-140332), and US Patent Application Publication 2002-0197558 A1 describe novel acid generators capable of generating perfluoroalkyl ether sulfonic acids.

Among these, perfluorooctanesulfonic acid and homologues thereof (collectively referred to as PFOS) are considered problematic with respect to their non-degradability and biological concentration in the environment. Manufacturers made efforts to develop partially fluorinated alkane sulfonic acids having a reduced degree of fluorine substitution as the replacement to PFOS. For instance, JP-A 2004-531749 describes the synthesis of α,α-difluoroalkanesulfonic acid salts from α,α-difluoroalkene and a sulfur compound and discloses a resist composition comprising a photoacid generator which generates such sulfonic acid upon exposure, specifically di(4-tert-butylphenyl)iodonium 1,1-difluoro-2-(1-naphthyl)-ethanesulfonate. JP-A 2004-2252 describes the development of α,α,β,β-tetrafluoroalkanesulfonic acid salts from α,α,β,β-tetrafluoro-α-iodoalkane and sulfur compound and discloses a photoacid generator capable of generating such a sulfonic acid and a resist composition comprising the same. JP-A 2002-214774 discloses such photoacid generators as difluorosulfoacetic acid alkyl esters and difluorosulfoacetic acid amides although their synthesis method is lacking. Furthermore, JP-A 2005-266766 discloses a photosensitive composition comprising a compound capable of generating a partially fluorinated alkane sulfonic acid having a sulfonylamide structure derived from perfluoroalkylene disulfonyl difluoride.

In an attempt to form a fine feature size pattern with a pitch of less than 200 nm, the problem of pattern density dependency (or optical proximity effect), that is, the size difference between isolated and grouped patterns having different optical contrast becomes significant. Using a photoacid generator capable of generating an acid with low diffusion, the problem of pattern density dependency can be overcome to some extent, but not to a satisfactory extent. While the resist composition is required to achieve a further reduction of the pattern rule as well as a good balance of sensitivity, substrate adhesion, and etching resistance, it is also required to ameliorate the pattern density dependency fundamentally without a loss of resolution.

Under the circumstances, it was proposed to form a polymer from an acryloyloxyphenyldiphenylsulfonium salt as a monomer for enhancing sensitivity (as described in JP-A 4-230645) and to incorporate the monomer into a polyhydroxystyrene resin for improving the line width roughness (LWR) of this base resin (as described in JP-A 2005-84365). However, since the sulfonium salt is bonded at its cation side to the polymer, the sulfonic acid generated therefrom upon exposure to high-energy radiation is equivalent to the sulfonic acids generated by conventional photoacid generators, which is unsatisfactory to overcome the outstanding problem. Also, sulfonium salts having an anion side incorporated into the polymer backbone such as polystyrenesulfonic acid are disclosed as effective in enhancing sensitivity or improving resist pattern profile (Japanese Patent No. 3613491). The acids generated therefrom are arenesulfonic and alkylsulfonic acid derivatives which have too low an acid strength to sever acid labile groups, especially acid labile groups in ArF chemically amplified resist compositions. JP-A 2006-178317 discloses a polymer having a plurality of partially fluorinated sulfonic acid anions as polymerizable units, and a resist material comprising the polymer. WO 2006-121096 discloses a polymer having three partially fluorinated sulfonic acid anions in combination with a specific lactone compound. JP-A 2007-197718 discloses three anions. Since they are esters of carboxylic acids which are strong acids, they are expected to be readily hydrolyzable and low stable. Copolymers derived therefrom have an insufficient solubility in resist solvents. Furthermore, JP-A 2008-133448 discloses a sulfonium salt having a partially fluorinated alkane sulfonic acid anion as a polymerizable unit, which has insufficient resist performance in terms of LWR.

With respect to the immersion lithography, some problems arise from minute water droplets which are left on the resist and wafer after the immersion exposure. They can often cause damages and defects to the resist pattern profile. The resist pattern after development can collapse or deform into a T-top profile. There exists a need for a patterning process which can form a satisfactory resist pattern after development according to the immersion lithography.

The lithography techniques which are considered promising next to the ArF lithography include electron beam (EB) lithography, $F_2$ lithography, extreme ultraviolet (EUV) lithography, and x-ray lithography. In these techniques, exposure must be done in vacuum or reduced pressure, which allows the sulfonic acid generated during exposure to volatilize, failing to form a satisfactory pattern profile. The sulfonic acid volatilized is damaging to the exposure system. In the EB and EUV lithography, it is desired to provide a resist material capable of minimizing the influence of acid diffusion in order to comply with further pattern size reductions.

CITATION LIST

Patent Document 1: JP-A 2000-122296
Patent Document 2: U.S. Pat. No. 6,048,672 (or JP-A H11-282168)
Patent Document 3: JP-A 2002-214774
Patent Document 4: US 2003-0113659 A1 (JP-A 2003-140332)
Patent Document 5: US 2002-0197558 A1
Patent Document 6: JP-A 2004-531749
Patent Document 7: JP-A 2004-2252
Patent Document 8: JP-A 2005-266766
Patent Document 9: JP-A 4-230645
Patent Document 10: JP-A 2005-84365
Patent Document 11: JP 3613491
Patent Document 12: JP-A 2006-178317
Patent Document 13: WO 2006-121096
Patent Document 14: JP-A 2007-197718
Patent Document 15: JP-A 2008-133448
Patent Document 16: JP 3796560
Patent Document 17: JP 3238465
Patent Document 18: JP 3865048
Non-Patent Document 1: Journal of Photopolymer Science and Technology, Vol. 17, No. 4, p 587 (2004)

SUMMARY OF INVENTION

An object of the present invention is to provide (1) a polymerizable anion-containing sulfonium salt useful as a monomer, (2) a polymer obtained from the sulfonium salt, (3) a resist composition comprising the polymer, which composition exhibits a high resolution and exposure latitude when processed by the photolithography using high-energy radiation, typically ArF excimer laser radiation, EUV radiation or EB as the light source, and (4) a patterning process using the resist composition.

The inventors have found that a polymerizable anion-containing sulfonium salt having the general formula (1) shown below can be easily prepared, and that a resist composition comprising as a base resin a polymer comprising recurring units of the polymerizable anion-containing sulfonium salt is improved in such properties as exposure latitude, pattern density dependency, and line width roughness (LWR), and best suited for precise micropatterning.

Thus the invention provides a polymerizable anion-containing sulfonium salt, a polymer derived therefrom, a resist composition, and a patterning process, as defined below.

[Claim 1]

A sulfonium salt having the general formula (1).

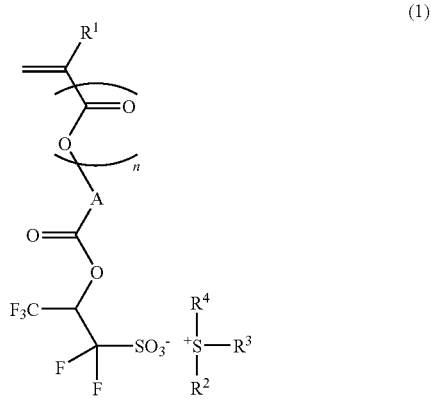

(1)

Herein $R^1$ is hydrogen, fluorine, methyl or trifluoromethyl, $R^2$, $R^3$ and $R^4$ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or at least two of $R^2$, $R^3$ and $R^4$ may bond together to form a ring with the sulfur atom to which they are attached, A is a divalent $C_1$-$C_{20}$ organic group which may contain a heteroatom, and n is 0 or 1.

[Claim 2]

A polymer capable of generating a sulfonic acid in response to high-energy radiation or heat, the sulfonic acid comprising recurring units of the general formula (1a).

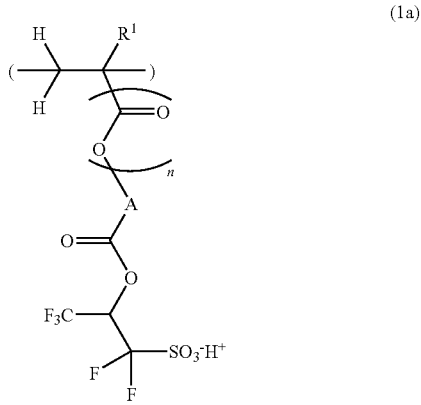

(1a)

Herein R¹ is hydrogen, fluorine, methyl or trifluoromethyl, A is a divalent $C_1$-$C_{20}$ organic group which may contain a heteroatom, and n is 0 or 1.

[Claim 3]

A polymer comprising recurring units of the general formula (1b).

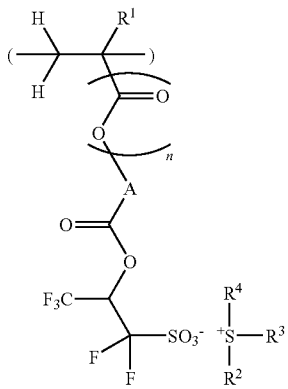
(1b)

Herein R¹ is hydrogen, fluorine, methyl or trifluoromethyl, $R^2$, $R^3$ and $R^4$ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or at least two of $R^2$, $R^3$ and $R^4$ may bond together to form a ring with the sulfur atom to which they are attached, A is a divalent $C_1$-$C_{20}$ organic group which may contain a heteroatom, and n is 0 or 1.

[Claim 4]

The polymer of claim 3, further comprising recurring units of at least one type selected from the general formulae (2) to (6).

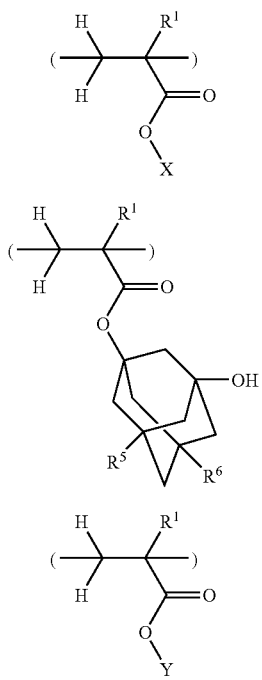
(2)
(3)
(4)

-continued

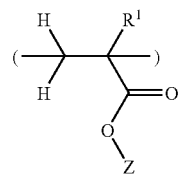
(5)
(6)

Herein R¹ is as defined above, $R^5$ and $R^6$ are each independently hydrogen or hydroxyl, X is an acid labile group, Y is a substituent group having lactone structure, Z is hydrogen, $C_1$-$C_{15}$ fluoroalkyl or $C_1$-$C_{15}$ fluoroalcohol-containing substituent group, N is an integer of 0 to 2, $R^7$ is hydrogen or $C_1$-$C_{10}$ alkyl, B is a single bond or a divalent $C_1$-$C_{10}$ organic group which may have oxygen substituted thereon, a is an integer of 0 to 3, and b is an integer of 1 to 3.

[Claim 5]

The polymer of claim 3 or 4, further comprising recurring units of at least one type selected from the general formulae (7) to (11).

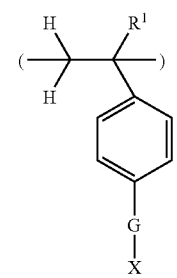
(7)

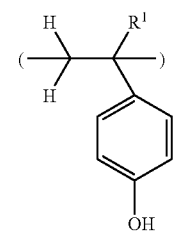
(8)

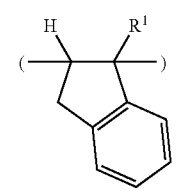
(9)

-continued

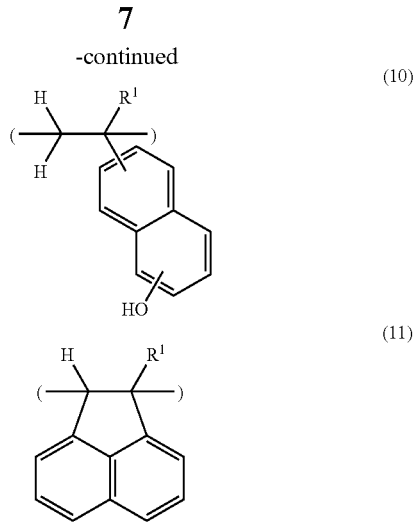

(10)

(11)

Herein R¹ and X are as defined above, and G is oxygen or carbonyloxy (—C(=O)O—).

[Claim 6]

A resist composition comprising the polymer of any one of claims 3 to 5 as a base resin.

[Claim 7]

A resist composition comprising the polymer of any one of claims 3 to 5 and a polymer free of recurring units of formula (1b) as a base resin.

[Claim 8]

The resist composition of claim 6 or 7, further comprising a surfactant which is insoluble in water and soluble in an alkaline developer.

[Claim 9]

A pattern forming process comprising the steps of applying the resist composition of any one of claims 6 to 8 onto a substrate to form a coating, heat treating the coating and exposing it to high-energy radiation through a photomask, optionally heat treating the exposed coating and developing it with a developer.

[Claim 10]

A pattern forming process comprising the steps of applying the resist composition of any one of claims 6 to 8 onto a substrate to form a resist coating, heat treating the resist coating, applying onto the resist coating a protective coating which is insoluble in water and soluble in an alkaline developer, exposing the coated substrate to high-energy radiation from a projection lens through a photomask while holding water between the substrate and the projection lens, optionally heat treating the exposed coating and developing it with a developer.

[Claim 11]

A pattern forming process comprising the steps of applying the resist composition of any one of claims 6 to 8 onto a substrate to form a coating, heat treating the coating, imagewise writing with an electron beam, heat treating the coating, and developing it with a developer.

It is noted that the resist composition of the invention can be applied to the immersion lithography. The immersion lithography involves prebaking a resist film and exposing the resist film to light through a projection lens with a liquid medium interposed between the resist film and the projection lens. The ArF immersion lithography generally uses pure water as the immersion medium. This technology, combined with a projection lens having a NA of at least 1.0, is important for the ArF lithography to survive to the 65 nm node and forth, with a further development thereof being accelerated.

The resist composition of the invention allows the feature size of the pattern after development to be reduced by various shrinkage techniques. For example, the hole size can be shrunk by such known techniques as thermal flow, RELACS, SAFIRE, and WASOOM. More effective shrinkage of hole size by thermal flow is possible particularly when the inventive polymer is blended with a hydrogenated cycloolefin ring-opening metathesis polymerization (ROMP) polymer having a low Tg.

ADVANTAGEOUS EFFECTS OF INVENTION

Since the polymerizable anion-containing sulfonium salt has fluorine atoms at α- and γ-positions relative to the sulfonic acid, it generates a sulfonic acid upon exposure to high-energy radiation, the sulfonic acid having a very high acidity enough to facilitate efficient scission of acid labile groups in chemically amplified resist compositions. The sulfonium salt is quite useful as a monomer for producing a base resin in a radiation-sensitive resist composition. Then, a radiation-sensitive resist composition comprising the polymer as a base resin exhibits a high resolution and is improved in pattern density dependency and exposure margin. The polymer is advantageously used as a resist material in precise micropatterning.

In the ArF immersion lithography, the leach-out of sulfonic acid in water is minimized, and the influence of water left on the wafer is minimized to restrain defect formation. In the disposal of resist-containing waste liquid after the device fabrication, (meth)acrylate moieties are hydrolyzable under basic conditions so that the polymer may be transformed into less accumulative compounds of lower molecular weight. In the disposal by combustion, the polymer is more combustible because of a low degree of fluorine substitution.

DESCRIPTION OF EMBODIMENTS

Figure 1:
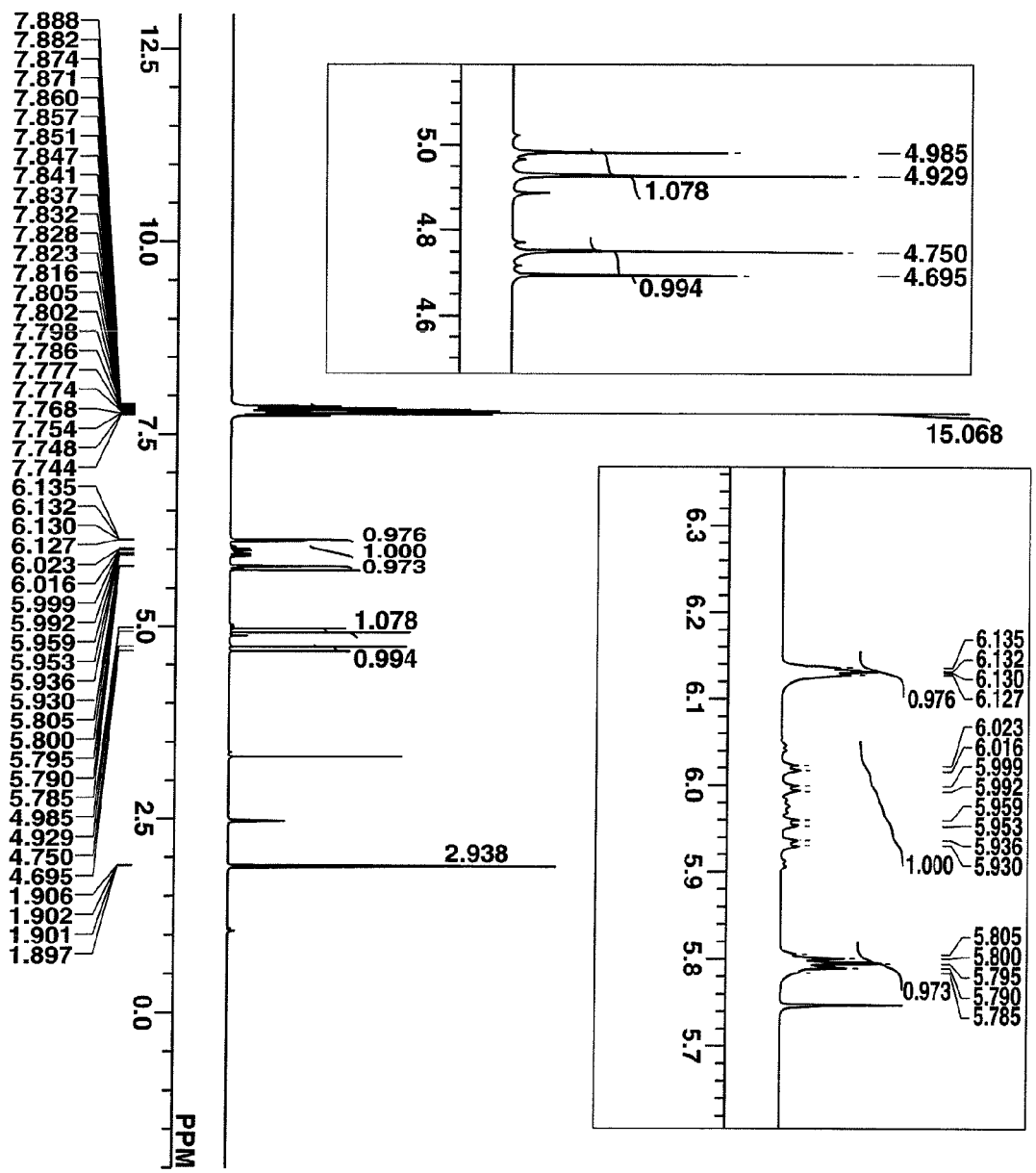
FIG. 1 is a diagram showing the $^1$H-NMR spectrum of Monomer 1 in Synthesis Example 2-1.

As used herein, the singular forms "a," "an" and "the" include plural referents unless the context clearly dictates otherwise. The notation (Cn—Cm) means a group containing from n to m carbon atoms per group. The term "high-energy radiation" is intended to encompass UV, deep UV, electron beam, EUV, x-ray, excimer laser, γ-ray and synchrotron radiation. In structural formulae, the broken line indicates a valence bond.

Sulfonium Salt

The first aspect of the invention relates to a polymerizable anion-containing sulfonium salt having the general formula (1).

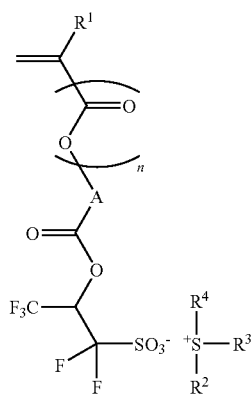

(1)

Herein $R^1$ is hydrogen, fluorine, methyl or trifluoromethyl, $R^2$, $R^3$ and $R^4$ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or at least two of $R^2$, $R^3$ and $R^4$ may bond together to form a ring with the sulfur atom to which they are attached, A is a divalent $C_1$-$C_{20}$ organic group which may contain a heteroatom, and n is 0 or 1.

In formula (1), $R^2$, $R^3$ and $R^4$ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or any two or more of $R^2$, $R^3$ and $R^4$ may bond together to form a ring with the sulfur atom to which they are attached.

Specifically, suitable alkyl groups include, but are not limited to, methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Suitable alkenyl groups include, but are not limited to, vinyl, allyl, propenyl, butenyl, hexenyl, and cyclohexenyl. Suitable oxoalkyl groups include, but are not limited to, 2-oxocyclopentyl, 2-oxocyclohexyl, 2-oxopropyl, 2-oxoethyl, 2-cyclopentyl-2-oxoethyl, 2-cyclohexyl-2-oxoethyl, and 2-(4-methylcyclohexyl)-2-oxoethyl. Suitable aryl groups include, but are not limited to, phenyl, naphthyl, thienyl, alkoxyphenyl groups such as 4-hydroxyphenyl, 4-methoxyphenyl, 3-methoxyphenyl, 2-methoxyphenyl, 4-ethoxyphenyl, 4-tert-butoxyphenyl, and 3-tert-butoxyphenyl, alkylphenyl groups such as 2-methylphenyl, 3-methylphenyl, 4-methylphenyl, 4-ethylphenyl, 4-tert-butylphenyl, 4-n-butylphenyl, and 2,4-dimethylphenyl, alkylnaphthyl groups such as methylnaphthyl and ethylnaphthyl, alkoxynaphthyl groups such as methoxynaphthyl and ethoxynaphthyl, dialkylnaphthyl groups such as dimethylnaphthyl and diethylnaphthyl, and dialkoxynaphthyl groups such as dimethoxynaphthyl and diethoxynaphthyl. Suitable aralkyl groups include benzyl, 1-phenylethyl, and 2-phenylethyl. Suitable aryloxoalkyl groups are 2-aryl-2-oxoethyl groups such as 2-phenyl-2-oxoethyl, 2-(1-naphthyl)-2-oxoethyl, and 2-(2-naphthyl)-2-oxoethyl. When any two or more of $R^2$, $R^3$ and $R^4$ bond together to form a ring with the sulfur atom, exemplary cyclic structures are shown below.

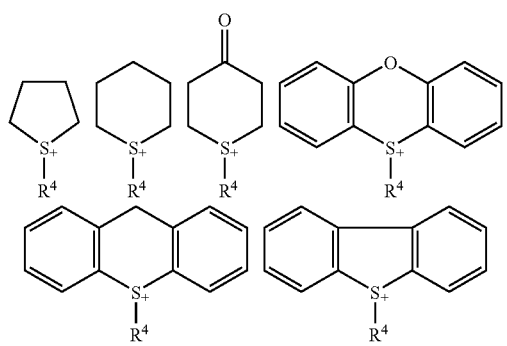

In the formulae, $R^4$ is as defined above.

Illustrative non-limiting examples of the sulfonium cation include triphenylsulfonium, 4-hydroxyphenyldiphenylsulfonium, bis(4-hydroxyphenyl)phenylsulfonium, tris(4-hydroxyphenyl)sulfonium, 4-tert-butoxyphenyldiphenylsulfonium, bis(4-tert-butoxyphenyl)phenylsulfonium, tris(4-tert-butoxyphenyl)sulfonium, 3-tert-butoxyphenyldiphenylsulfonium, bis(3-tert-butoxyphenyl)phenylsulfonium, tris(3-tert-butoxyphenyl)sulfonium, 3,4-di-tert-butoxyphenyldiphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, 4-tert-butoxycarbonylmethyloxyphenyldiphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyldiphenylsulfonium, (4-hydroxy-3,5-dimethylphenyl)diphenylsulfonium, (4-n-hexyloxy-3,5-dimethylphenyl)diphenylsulfonium, dimethyl(2-naphthyl)sulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl-2-thienylsulfonium, 4-n-butoxynaphthyl-1-thiacyclopentanium, 2-n-butoxynaphthyl-1-thiacyclopentanium, 4-methoxynaphthyl-1-thiacyclopentanium, and 2-methoxynaphthyl-1-thiacyclopentanium. Inter alia, triphenylsulfonium, 4-tert-butylphenyldiphenylsulfonium, 4-tert-butoxyphenyldiphenylsulfonium, tris(4-tert-butylphenyl)sulfonium, tris(4-tert-butoxyphenyl)sulfonium, and dimethylphenylsulfonium are preferred.

In formula (1), $R^1$ is a hydrogen atom, fluorine atom, methyl group or trifluoromethyl group, with hydrogen and methyl being preferred. The subscript n is 0 or 1. A is a divalent $C_1$-$C_{20}$ organic group which may contain a heteroatom, specifically a straight, branched or cyclic aliphatic hydrocarbon or aromatic hydrocarbon, typically straight, branched or cyclic alkylene group. Specifically exemplary structures of the anion moiety in formula (1) are illustrated below, but not limited thereto.
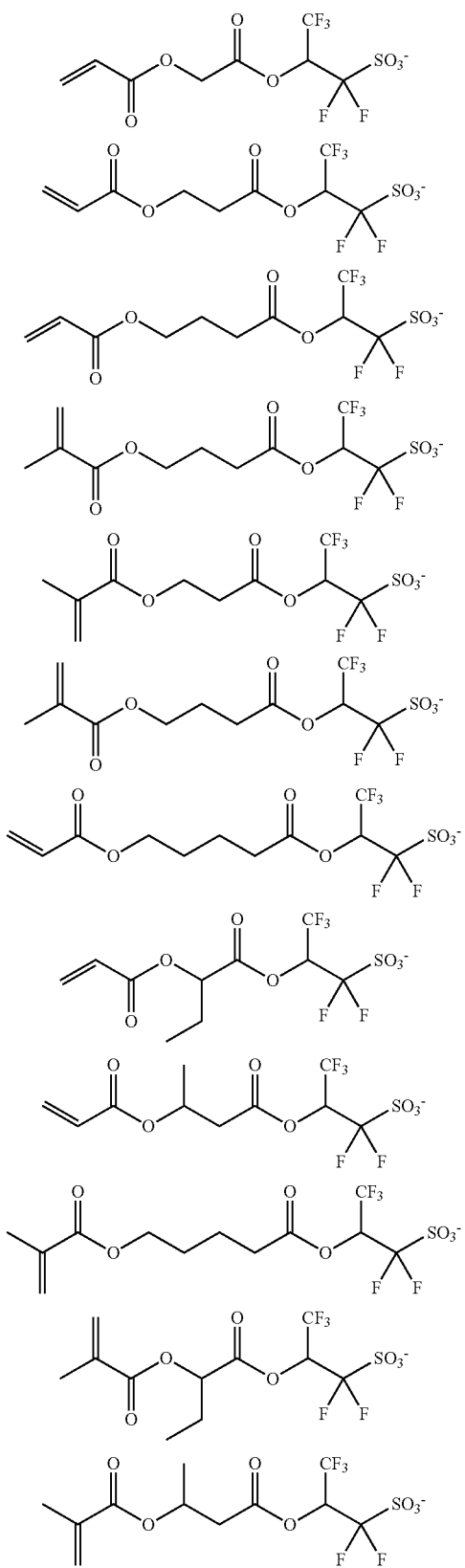
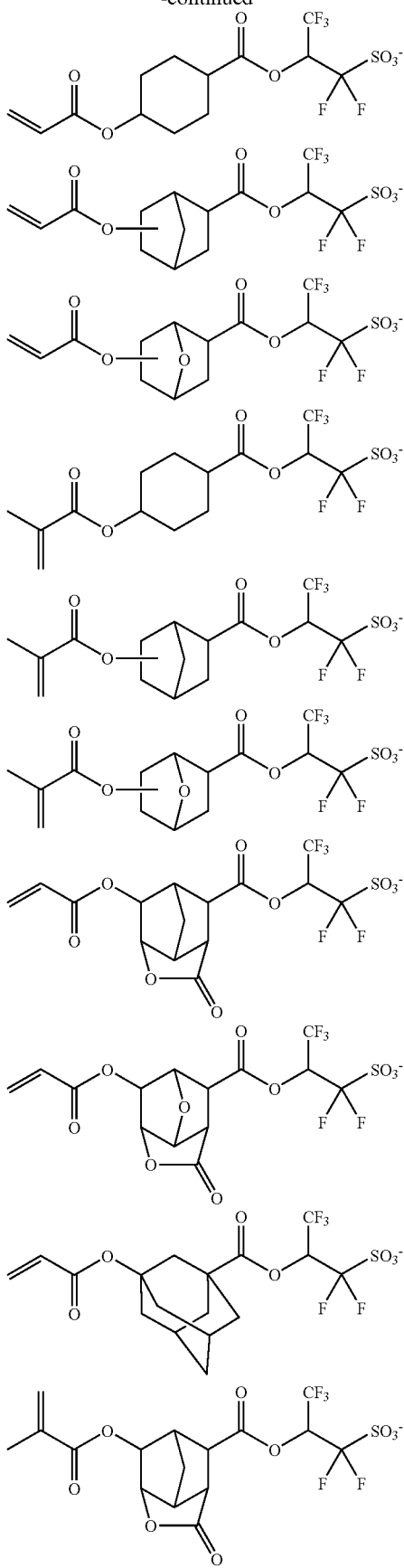

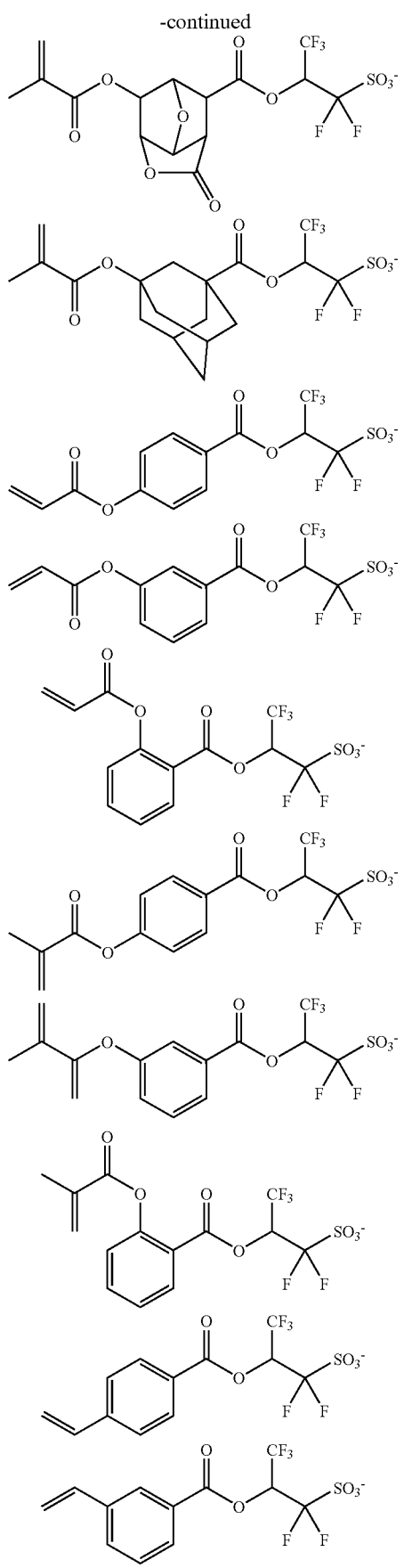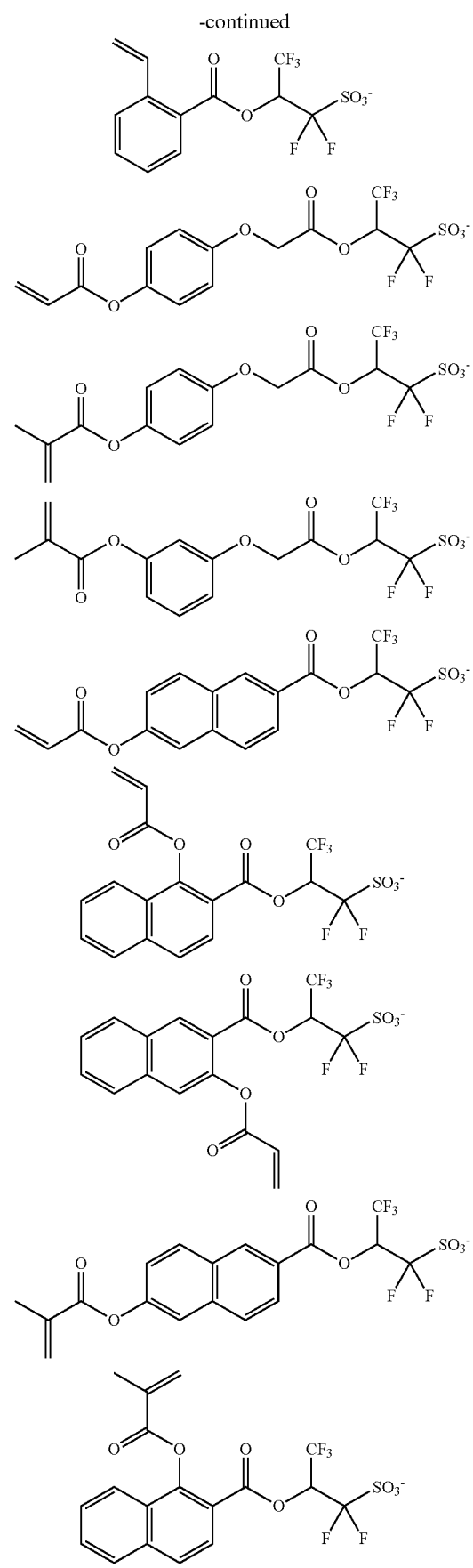

-continued

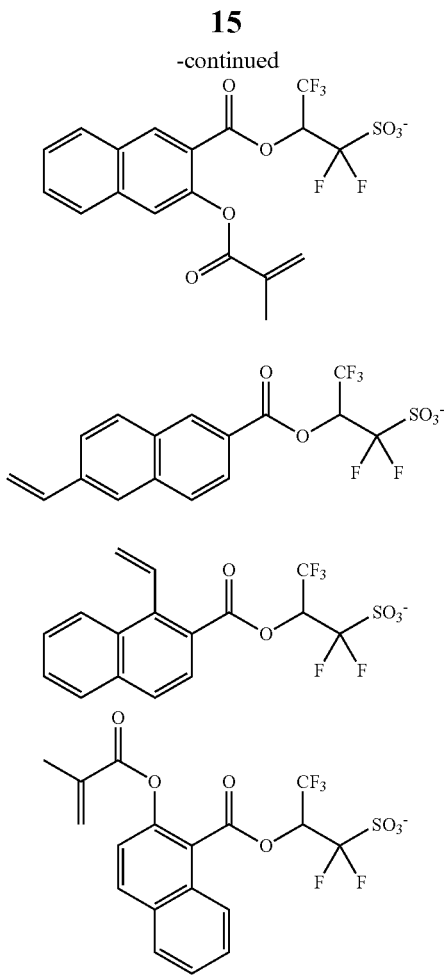

It is appreciated that the polymerizable anion-containing sulfonium salts of formula (1) are merely illustrative, and iodonium salts or ammonium salts having such a polymerizable anion may be synthesized by the same method as the invention and equally applicable to the polymer, resist composition and pattern-forming process to be described later.

Illustrative non-limiting examples of the iodonium cation include diphenyliodonium, bis(4-methylphenyl)iodonium, bis(4-(1,1-dimethylethyl)phenyl)iodonium, bis(4-(1,1-dimethylpropyl)phenyl)iodonium, and (4-(1,1-dimethylethoxy)phenyl)phenyliodonium. Illustrative non-limiting examples of the ammonium salt include tertiary ammonium salts such as trimethylammonium, triethylammonium, tributylammonium and N,N-dimethylanilinium, and quaternary ammonium salts such as tetramethylammonium, tetraethylammonium, and tetrabutylammonium. The iodonium salt having the specific polymerizable anion and a polymer having the iodonium salt in recurring units may be used as a component having a photoacid generating ability or thermal acid generating ability. The ammonium salt having the specific polymerizable anion and a polymer having the ammonium salt in recurring units may be used as a thermal acid generator.

The second aspect of the invention relates to a polymer or high-molecular weight compound capable of generating a sulfonic acid in response to high-energy radiation (e.g., UV, deep-UV, EUV, electron beam, x-ray, excimer laser, gamma-ray and synchrotron radiation) or heat, the sulfonic acid comprising recurring units of the general formula (1a):

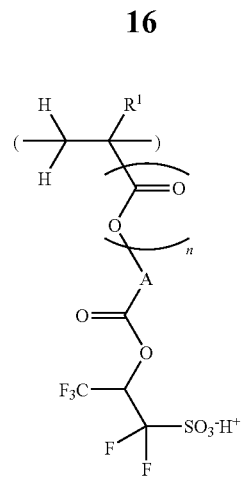

Herein $R^1$ is hydrogen, fluorine, methyl or trifluoromethyl, A is a divalent $C_1$-$C_{20}$ organic group which may contain a heteroatom, and n is 0 or 1.

In formula (1a), $R^1$, A and n are as defined above. When an acid generator is incorporated in a polymer unit (referred to as polymer-bound PAG, hereinafter), acid diffusion is suppressed and as a consequent, parameters such as exposure latitude and mask error factor may be improved, but line width roughness (LWR) may be degraded. When a resist composition comprising a polymer having the sulfonium salt of the invention incorporated therein is used, LWR may also be improved because the polymer-bound PAG is endowed with an appropriate mobility due to the interposition of a linker unit represented by A in formula (1a). Since the acid generator has fluorine atoms at α- and γ-positions relative to the sulfonic acid, it generates a sulfonic acid upon exposure to high-energy radiation, the sulfonic acid having a very high strength enough to facilitate efficient scission of acid labile groups in chemically amplified resist compositions. The compound is quite useful as a monomer for producing a base resin in a radiation-sensitive resist composition.

Now the method for synthesizing the sulfonium salt having a polymerizable anion represented by formula (1) according to the invention is described.

The sulfonium salt having a polymerizable anion represented by formula (1) can be synthesized by converting a carboxylic acid having a polymerizable functional group such as (meth)acryloyl or vinyl into a carboxylic acid chloride and reacting it with triphenylsulfonium 1,1,3,3,3-pentafluoro-2-hydroxypropanesulfonate, which has been synthesized by the inventors, under basic conditions.

Alternatively, the sulfonium salt having a polymerizable anion represented by formula (1) may be synthesized according to the following formulation. First, triphenylsulfonium 1,1,3,3,3-pentafluoro-2-hydroxypropane-sulfonate, which has been synthesized by the inventors, is reacted with chloroalkylcarboxylic chloride under basic conditions to form triphenylsulfonium 2-(chloroalkylcarbonyloxy)-1,1,3,3,3-pentafluoro-2-hydroxypropanesulfonate. This is reacted with a metal salt of a carboxylic acid having a polymerizable functional group such as (meth)acryloyl or vinyl or with the carboxylic acid under basic conditions, yielding the sulfonium salt having a polymerizable anion represented by formula (1). The synthesis formulation described above is merely exemplary and the invention is not limited thereto.

Briefly noted herein is the synthesis of triphenylsulfonium 1,1,3,3,3-pentafluoro-2-hydroxypropanesulfonate. First, an aliphatic or aromatic carboxylic acid ester of 1,1,3,3,3-pentafluoropropen-2-yl, typically 1,1,3,3,3-pentafluoropropen- 2-yl benzoate, which was developed by Nakai et al. (Tetrahedron Lett., Vol. 29, 4119 (1988)) using 1,1,1,3,3,3-hexafluoro-2-propanol as the starting reactant, is reacted with a sulfite in water, forming a corresponding 1,1,3,3,3-pentafluoro-2-acyloxy-propanesulfonic acid salt or 1,1,3,3,3-pentafluoro-2-arenecarbonyloxypropanesulfonic acid salt. This salt is ion-exchanged with a suitable sulfonium salt, forming triphenylsulfonium 1,1,3,3,3-pentafluoro-2-acyloxypropanesulfonate or triphenylsulfonium 1,1,3,3,3-pentafluoro-2-arenecarbonyloxypropanesulfonate. The carboxylate moiety of the sulfonate is then subjected to hydrolysis with the aid of an alkali such as sodium hydroxide or potassium hydroxide, or solvolysis with the aid of an alcohol and base, yielding the target compound, triphenylsulfonium 1,1,3,3,3-pentafluoro-2-hydroxypropanesulfonate. Synthesis of sulfonium salts other than triphenylsulfonium may be similarly carried out.

The reaction to synthesize the polymerizable anion proceeds readily by any well-known procedure. The reaction may be carried out by dissolving a sulfonium salt such as triphenylsulfonium 1,1,3,3,3-pentafluoro-2-hydroxypropanesulfonate in a solvent such as methylene chloride, tetrahydrofuran or acetonitrile, sequentially or simultaneously adding thereto a base such as triethylamine, pyridine or 4-dimethylaminopyridine and an acid chloride compound containing a polymerizable functional group, and cooling or heating the system as desired.

Polymer

The polymer or high-molecular weight compound of the invention comprises recurring units derived from the sulfonium salt having a polymerizable anion represented by formula (1). Specifically, the recurring units derived from the sulfonium salt having a polymerizable anion represented by formula (1) include units of the general formula (1b):

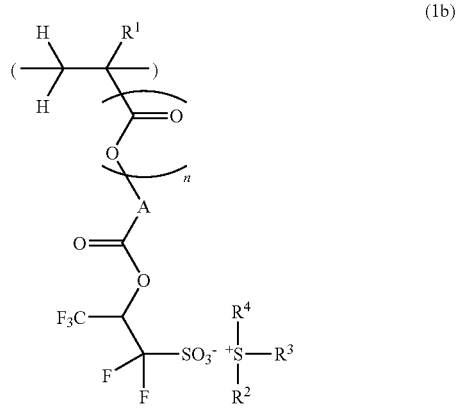

(1b)

wherein $R^1$ to $R^4$, A and n are as defined above.

In addition to the recurring units of formula (1b), the polymer of the invention may further comprise recurring units of at least one type selected from the general formulae (2) to (6):

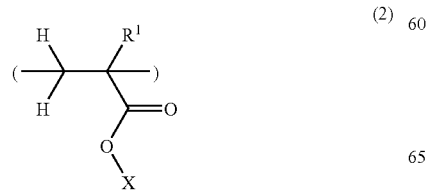

(2)

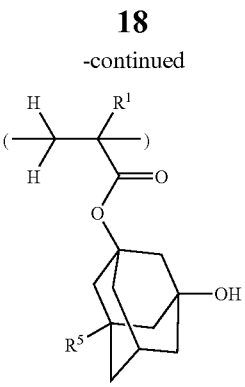

(3)

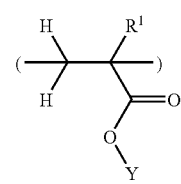

(4)

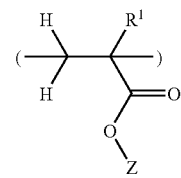

(5)

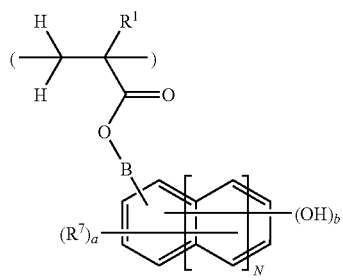

(6)

wherein $R^1$ is as defined above, $R^5$ and $R^6$ are each independently a hydrogen atom or hydroxyl group, X is an acid labile group, Y is a lactone structure-containing substituent group, Z is hydrogen, a $C_1$-$C_{15}$ fluoroalkyl group or a $C_1$-$C_{15}$ fluoroalcohol-containing substituent group, N is an integer of 0 to 2, $R^7$ is a hydrogen atom or $C_1$-$C_{10}$ alkyl group, B is a single bond or a divalent $C_1$-$C_{10}$ organic group which may have oxygen substituted thereon, a is an integer of 0 to 3, and b is an integer of 1 to 3.

Under the action of an acid, a polymer comprising recurring units of formula (2) is decomposed to generate a carboxylic acid and turns into an alkali-soluble polymer.

The acid labile groups represented by X may be selected from a variety of such groups, for example, groups of the following general formulae (L1) to (L4) and (L2-2), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

(L1)

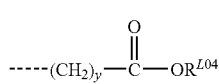  (L2)

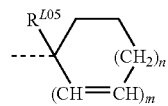  (L3)

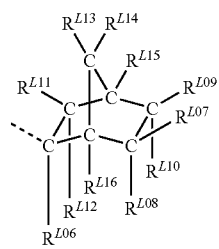  (L4)

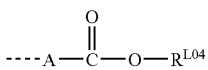  (L2-2)

The broken line indicates a valence bond.

In formula (L1), $R^{L01}$ and $R^{L02}$ are hydrogen or straight, branched or cyclic alkyl groups of 1 to 18 carbon atoms, preferably 1 to 10 carbon atoms. Examples include hydrogen, methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl.

$R^{L03}$ is a monovalent hydrocarbon group of 1 to 18 carbon atoms, preferably 1 to 10 carbon atoms, which may contain a hetero atom such as oxygen, examples of which include straight, branched or cyclic alkyl groups and substituted forms of these groups in which some hydrogen atoms are replaced by hydroxyl, alkoxy, oxo, amino, alkylamino or the like. Examples of the substituted alkyl groups are shown below.

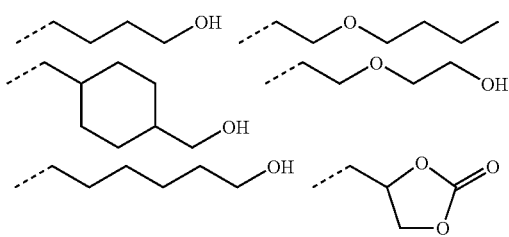

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

In formula (L2), $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. In formula (L2), y is an integer of 0 to 6.

In formula (L2-2), $R^{L04}$ is as defined above, and examples of the moiety of the formula:

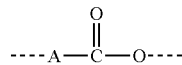

are given below.

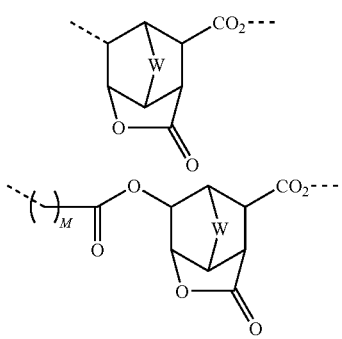

Herein W is an oxygen atom or $CH_2$, and M is an integer of 1 to 3.

In formula (L3), $R^{L05}$ is a substituted or unsubstituted, $C_1$-$C_8$ straight, branched or cyclic alkyl group or a substituted or unsubstituted $C_6$-$C_{20}$ aryl group. Examples of the substituted or unsubstituted alkyl groups include straight, branched or cyclic ones such as methyl, ethyl, propyl, isopropyl, n-butyl, sec-butyl, tert-butyl, tert-amyl, n-pentyl, n-hexyl, cyclopentyl and cyclohexyl; and substituted forms of the foregoing in which some hydrogen atoms are replaced by hydroxyl, alkoxy, carboxy, alkoxycarbonyl, oxo, amino, alkylamino, cyano, mercapto, alkylthio, sulfo or other groups. Exemplary substituted or unsubstituted aryl groups are phenyl, methylphenyl, naphthyl, anthryl, phenanthryl, and pyrenyl. In formula (L3), m is 0 or 1, n is 0, 1, 2 or 3, and 2 m+n is equal to 2 or 3.

In formula (L4), $R^{L06}$ is a substituted or unsubstituted, $C_1$-$C_8$ straight, branched or cyclic alkyl group or a substituted or unsubstituted $C_6$-$C_{20}$ aryl group. Examples of these groups are the same as exemplified for $R^{L05}$. $R^{L07}$ to $R^{L16}$ independently represent hydrogen or monovalent $C_1$-$C_{15}$ hydrocarbon groups. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of the foregoing in which some hydrogen atoms are replaced by hydroxyl, alkoxy, carboxy, alkoxycarbonyl, oxo, amino, alkylamino, cyano, mercapto, alkylthio, sulfo or other groups. Alternatively, two of $R^{L07}$ to $R^{L16}$ may bond together to form a ring with the carbon atom to which they are attached (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents a divalent $C_1$-$C_{15}$ hydrocarbon group when they form a ring, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or a similar pair).

Of the acid labile groups of formula (L1), the straight and branched ones are exemplified by the following groups.

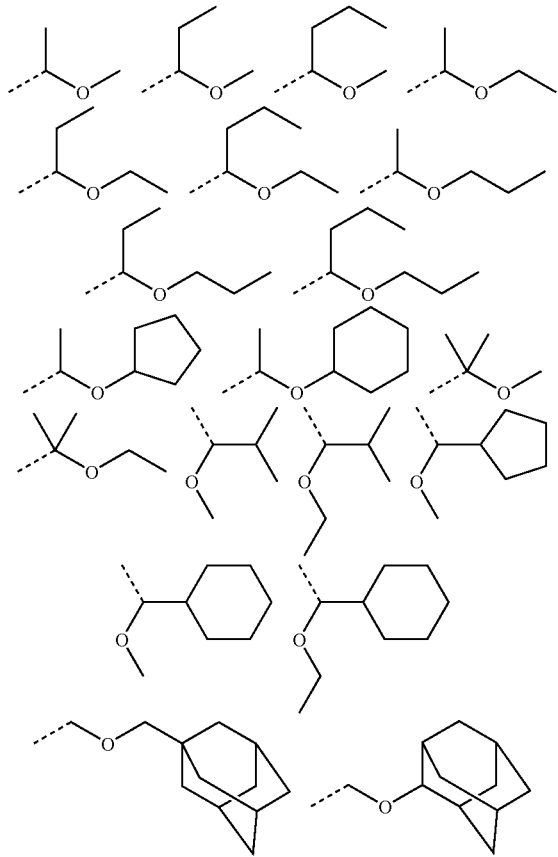

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L2-2) include
9-(tert-butyloxycarbonyl)-5-oxo-4-oxatricyclo[4.2.1.0$^{3,7}$]-nonan-2-yl,
9-(tert-amyloxycarbonyl)-5-oxo-4-oxatricyclo[4.2.1.0$^{3,7}$]nonan-2-yl,
9-(2-(adamantan-1-yl)propan-2-yloxycarbonyl)-5-oxo-4-oxatricyclo[4.2.1.0$^{3,7}$]nonan-2-yl,
9-(1-ethylcyclopentyloxycarbonyl)-5-oxo-4-oxatricyclo-[4.2.1.0$^{3,7}$]nonan-2-yl,
9-(1-butylcyclopentyloxycarbonyl)-5-oxo-4-oxatricyclo-[4.2.1.0$^{3,7}$]nonan-2-yl,
9-(1-ethylcyclohexyloxycarbonyl)-5-oxo-4-oxatricyclo-[4.2.1.0$^{3,7}$]nonan-2-yl,
9-(1-butylcyclohexyloxycarbonyl)-5-oxo-4-oxatricyclo-[4.2.1.0$^{3,7}$]nonan-2-yl,
9-(2-methyl-2-adamantyloxycarbonyl)-5-oxo-4-oxatricyclo-[4.2.1.0$^{3,7}$]nonan-2-yl,
9-(2-ethyl-2-adamantyloxycarbonyl)-5-oxo-4-oxatricyclo-[4.2.1.0$^{3,7}$]nonan-2-yl,
9-(4-ethyltetracyclo[6.2.1.1.0]dodecan-4-yloxycarbonyl)-5-oxo-4-oxatricyclo[4.2.1.0$^{3,7}$]nonan-2-yl,
2-(9-(tert-butyloxycarbonyl)-5-oxo-4-oxatricyclo[4.2.1.0$^{3,7}$]-nonan-2-yloxy)-2-oxoethyl,
2-(9-(tert-amyloxycarbonyl)-5-oxo-4-oxatricyclo[4.2.1.0$^{3,7}$]-nonan-2-yloxy)-2-oxoethyl,
2-(9-(2-(adamantan-1-yl)propan-2-yloxycarbonyl)-5-oxo-4-oxatricyclo[4.2.1.0$^{3,7}$]nonan-2-yloxy)-2-oxoethyl,
2-(9-(1-ethylcyclopentyloxycarbonyl)-5-oxo-4-oxatricyclo-[4.2.1.0$^{3,7}$]nonan-2-yloxy)-2-oxoethyl,
2-(9-(1-butylcyclopentyloxycarbonyl)-5-oxo-4-oxatricyclo-[4.2.1.0$^{3,7}$]nonan-2-yloxy)-2-oxoethyl,
2-(9-(1-ethylcyclohexyloxycarbonyl)-5-oxo-4-oxatricyclo-[4.2.1.0$^{3,7}$]nonan-2-yloxy)-2-oxoethyl,
2-(9-(1-butylcyclohexyloxycarbonyl)-5-oxo-4-oxatricyclo-[4.2.1.0$^{3,7}$]nonan-2-yloxy)-2-oxoethyl,
2-(9-(2-methyl-2-adamantyloxycarbonyl)-5-oxo-4-oxatricyclo-[4.2.1.0$^{3,7}$]nonan-2-yloxy)-2-oxoethyl,
2-(9-(2-ethyl-2-adamantyloxycarbonyl)-5-oxo-4-oxatricyclo-[4.2.1.0$^{3,7}$]nonan-2-yloxy)-2-oxoethyl,
2-(9-(4-ethyltetracyclo[6.2.1.1$^{3,6}$.0$^{2,7}$]dodecan-4-yloxycarbonyl)-5-oxo-4-oxatricyclo[4.2.1.0$^{3,7}$]nonan-2-yloxy)-2-oxoethyl,
4-(9-(tert-butyloxycarbonyl)-5-oxo-4-oxatricyclo[4.2.1.0$^{3,7}$]-nonan-2-yloxy)-4-oxobutyl,
4-(9-(tert-amyloxycarbonyl)-5-oxo-4-oxatricyclo[4.2.1.0$^{3,7}$]-nonan-2-yloxy)-4-oxobutyl,
4-(9-(2-(adamantan-1-yl)propan-2-yloxycarbonyl)-5-oxo-4-oxatricyclo[4.2.1.0$^{3,7}$]nonan-2-yloxy)-4-oxobutyl,
4-(9-(1-ethylcyclopentyloxycarbonyl)-5-oxo-4-oxatricyclo-[4.2.1.0$^{3,7}$]nonan-2-yloxy)-4-oxobutyl,
4-(9-(1-butylcyclopentyloxycarbonyl)-5-oxo-4-oxatricyclo-[4.2.1.0$^{3,7}$]nonan-2-yloxy)-4-oxobutyl,
4-(9-(1-ethylcyclohexyloxycarbonyl)-5-oxo-4-oxatricyclo-[4.2.1.0$^{3,7}$]nonan-2-yloxy)-4-oxobutyl,
4-(9-(1-butylcyclohexyloxycarbonyl)-5-oxo-4-oxatricyclo-[4.2.1.0$^{3,7}$]nonan-2-yloxy)-4-oxobutyl,
4-(9-(2-methyl-2-adamantyloxycarbonyl)-5-oxo-4-oxatricyclo-[4.2.1.0$^{3,7}$]nonan-2-yloxy)-4-oxobutyl,
4-(9-(2-ethyl-2-adamantyloxycarbonyl)-5-oxo-4-oxatricyclo-[4.2.1.0$^{3,7}$]nonan-2-yloxy)-4-oxobutyl,
4-(9-(4-ethyltetracyclo[6.2.1.1$^{3,6}$.0$^{2,7}$]dodecan-4-yloxycarbonyl)-5-oxo-4-oxatricyclo[4.2.1.0$^{3,7}$]nonan-2-yloxy)-4-oxobutyl, etc.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

Of the acid labile groups of formula (L4), those groups of the following formulae (L4-1) to (L4-4) are more preferred.

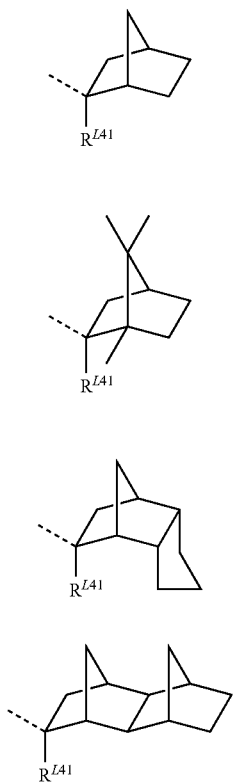

(L4-1)

(L4-2)

(L4-3)

(L4-4)

In formulae (L4-1) to (L4-4), the broken line denotes a bonding site and direction. $R^{L41}$ is each independently selected from monovalent hydrocarbon groups, typically straight, branched or cyclic $C_1$-$C_{10}$ alkyl groups, for example, methyl, ethyl, propyl, isopropyl, n-butyl, sec-butyl, tert-butyl, tert-amyl, n-pentyl, n-hexyl, cyclopentyl, and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-1) and (L4-3-2).

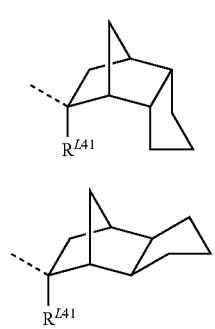

(L4-3-1)

(L4-3-2)

Similarly, the general formula (L4-4) represents one or a mixture of two or more selected from groups having the following general formulas (L4-1) to (L4-4-4).

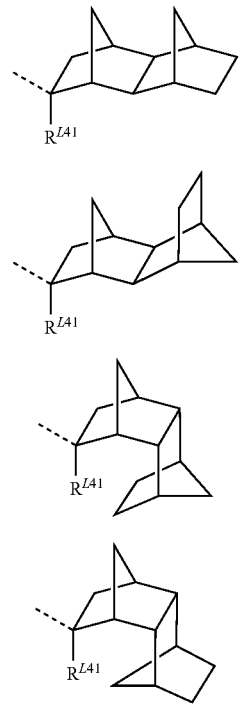

(L4-4-1)

(L4-4-2)

(L4-4-3)

(L4-4-4)

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1] heptane ring, which ensures high reactivity for acid catalyzed elimination reaction (see JP-A 2000-336121). In preparing these monomers having a tertiary exo-alkyl group of bicyclo [2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

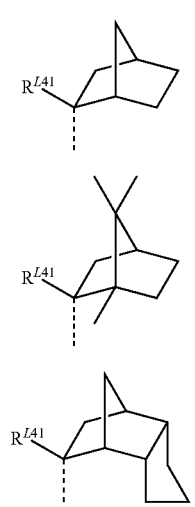

(L4-1-endo)

(L4-2-endo)

(L4-3-endo)

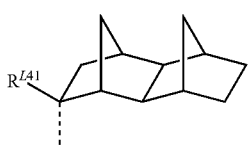

(L4-4-endo)

(See JP-A 2000-336121)

Illustrative examples of the acid labile group of formula (L4) are given below, but not limited thereto.

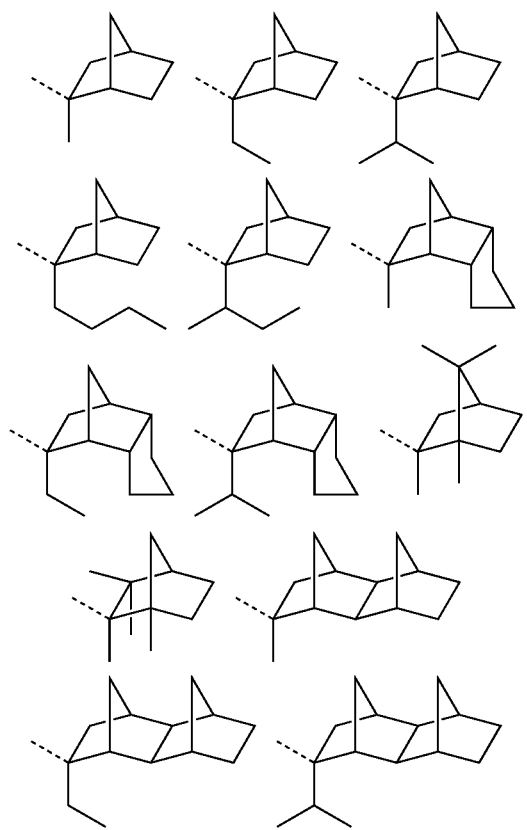

Examples of the tertiary $C_4$-$C_{20}$ alkyl, tri($C_1$-$C_6$-alkyl)silyl and $C_4$-$C_{20}$ oxoalkyl groups are as exemplified above for $R^{L04}$.

Illustrative, non-limiting examples of the recurring units of formula (2) are given below. Although only (meth)acrylates are illustrated, those which are separated by a divalent linking group of formula (L2) or (L2-2) are also useful.

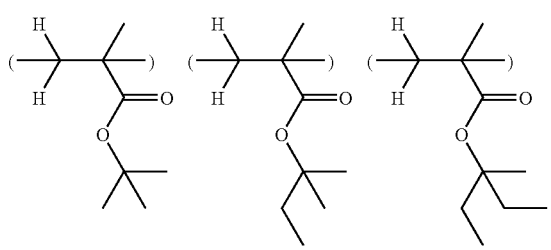

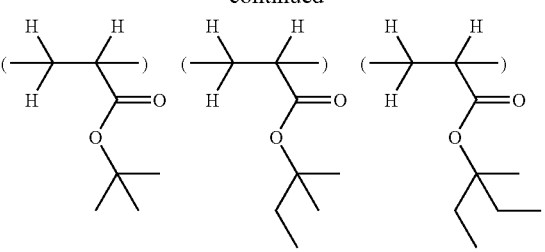

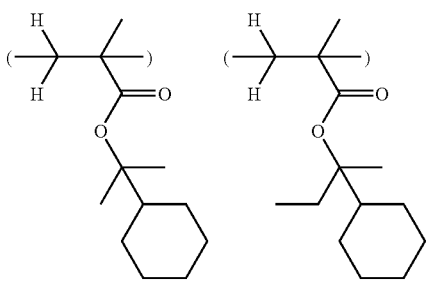

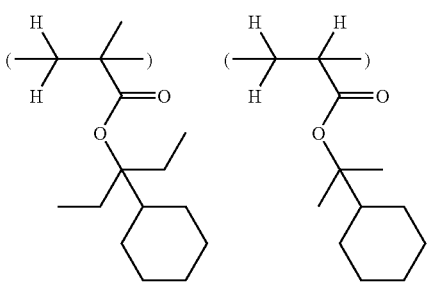

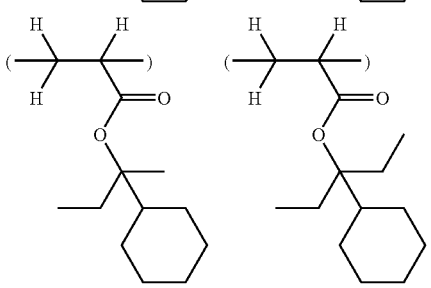

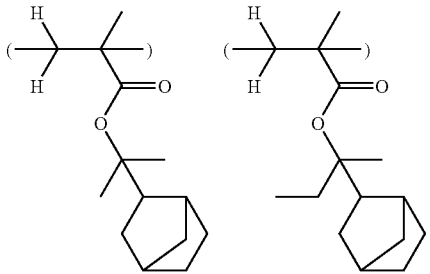

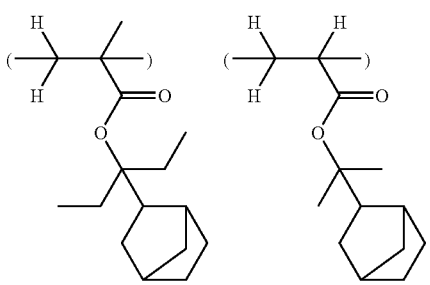

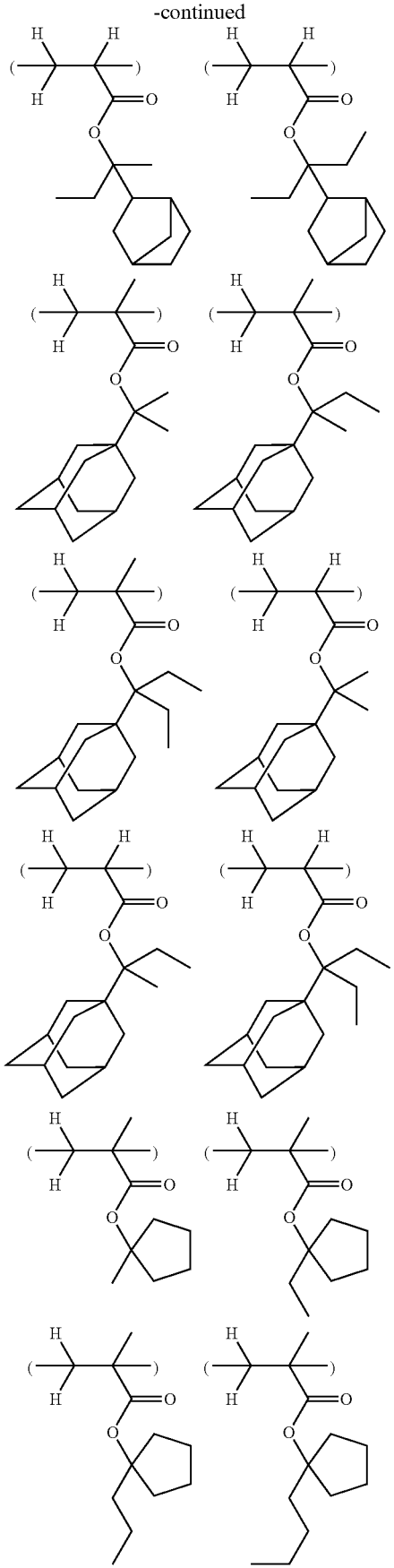
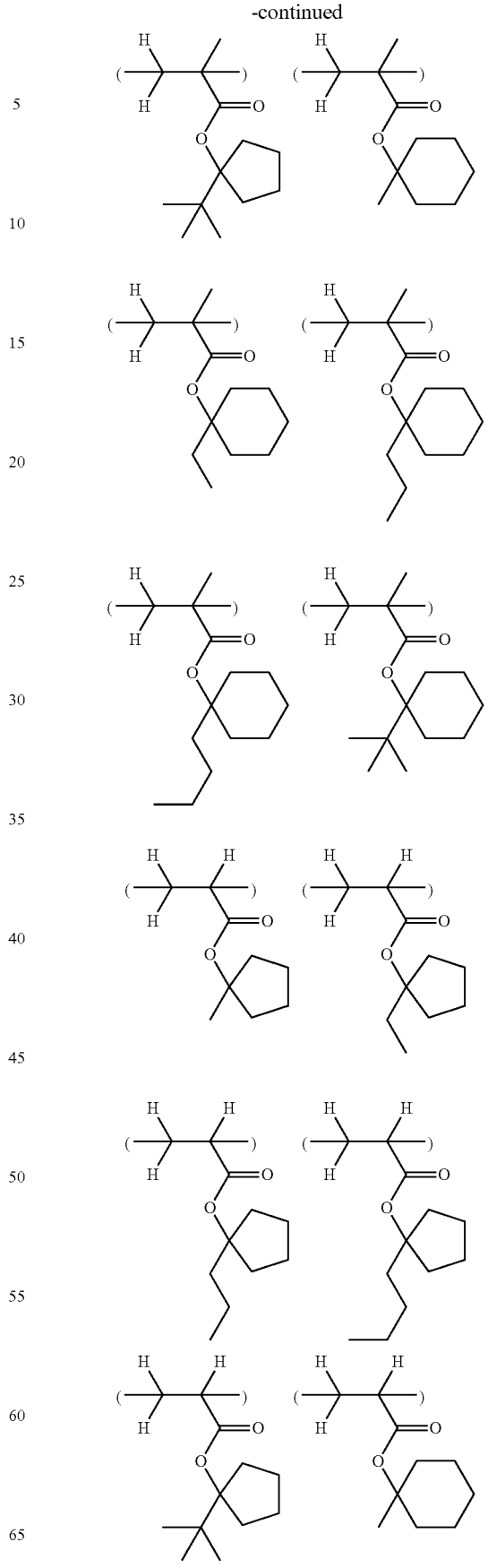

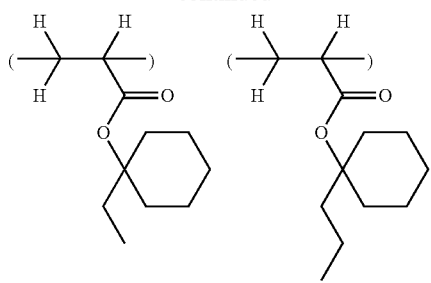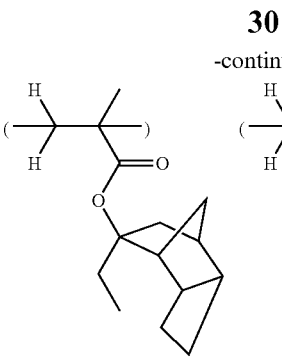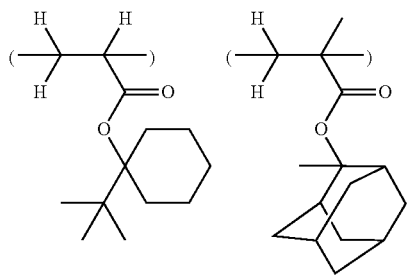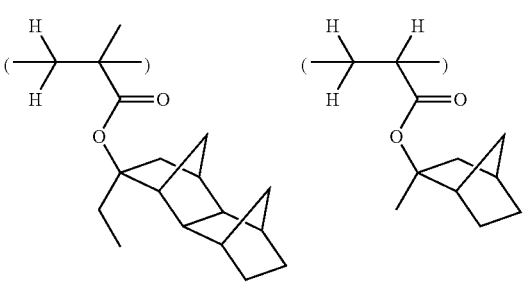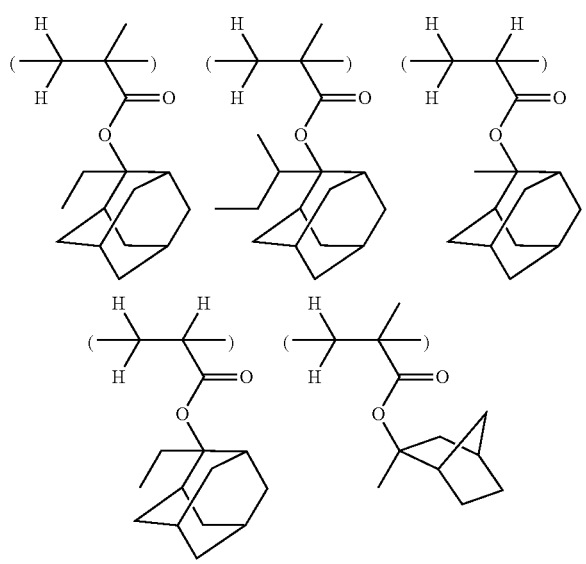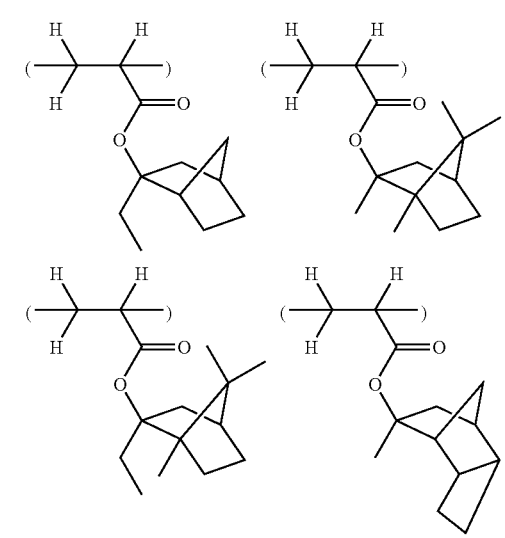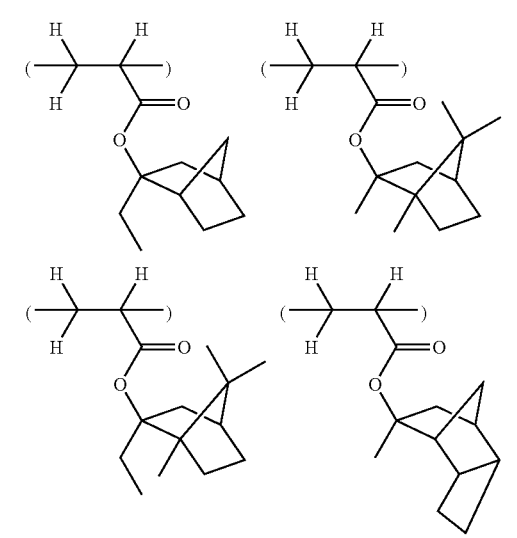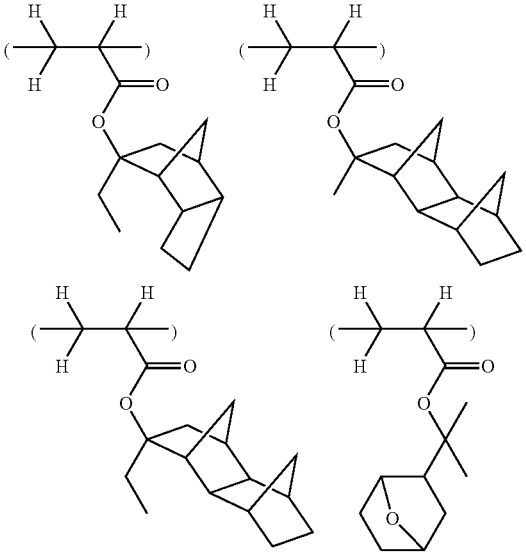

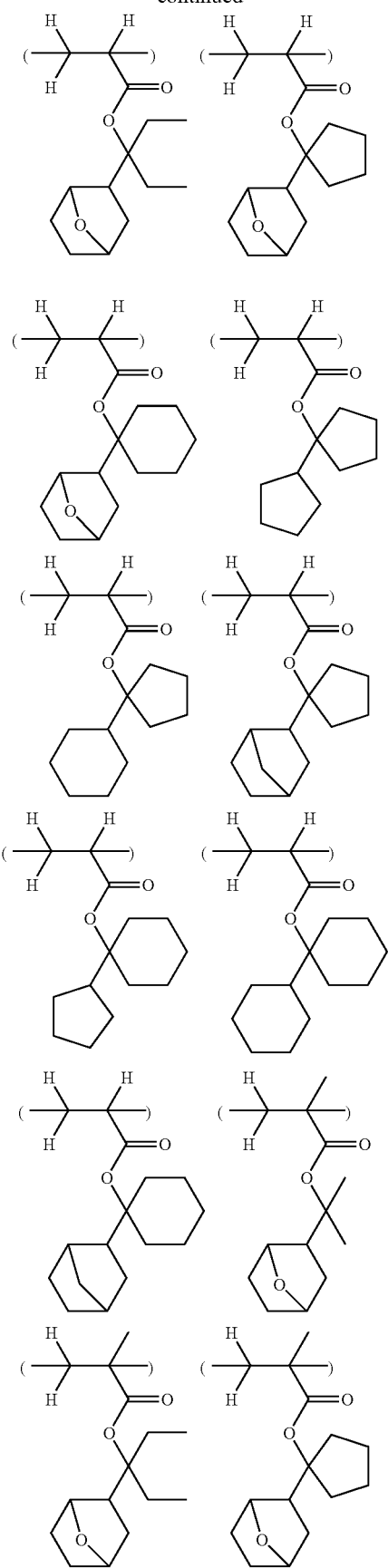
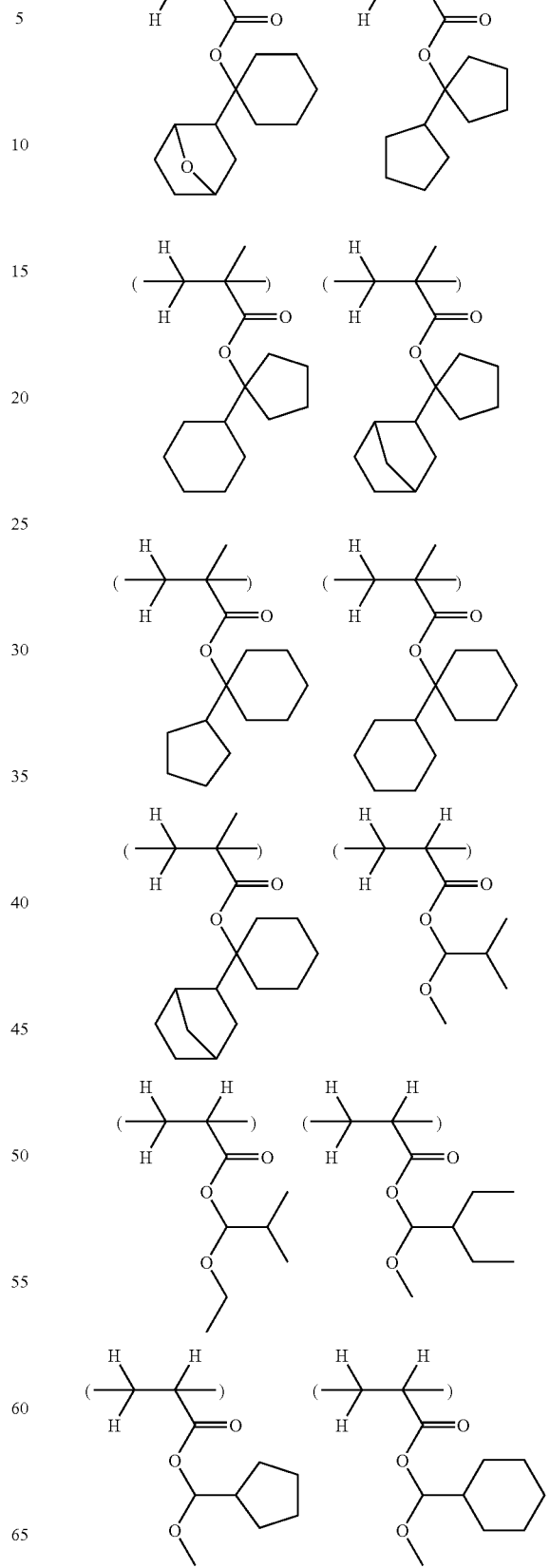

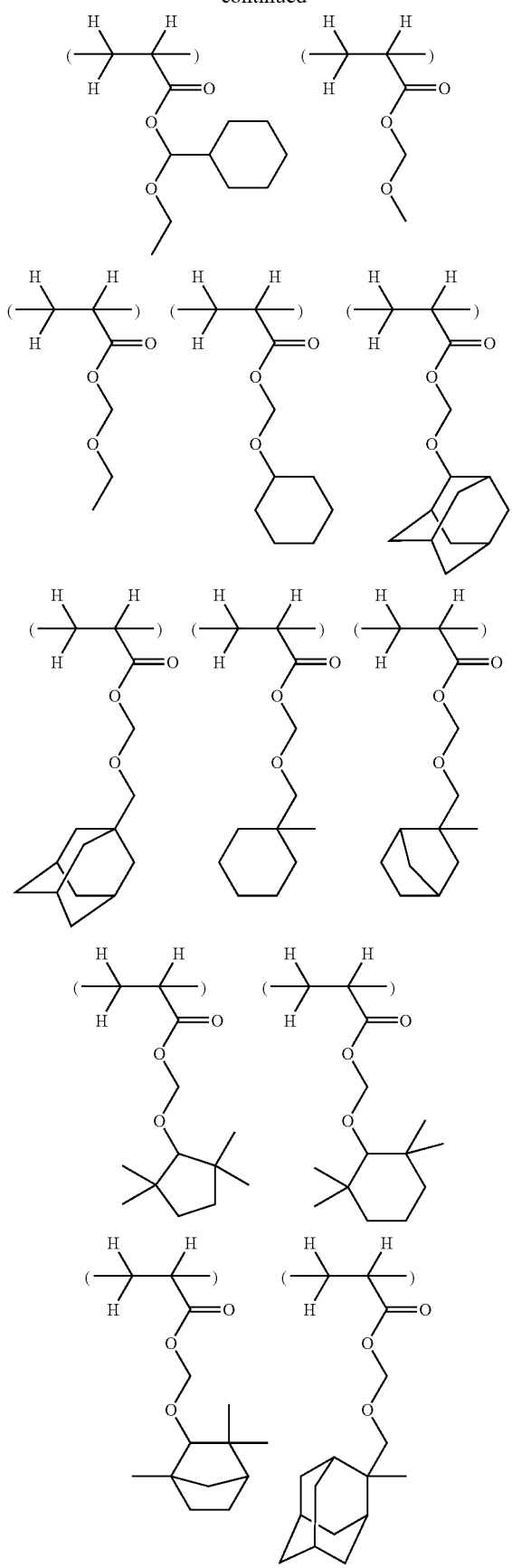
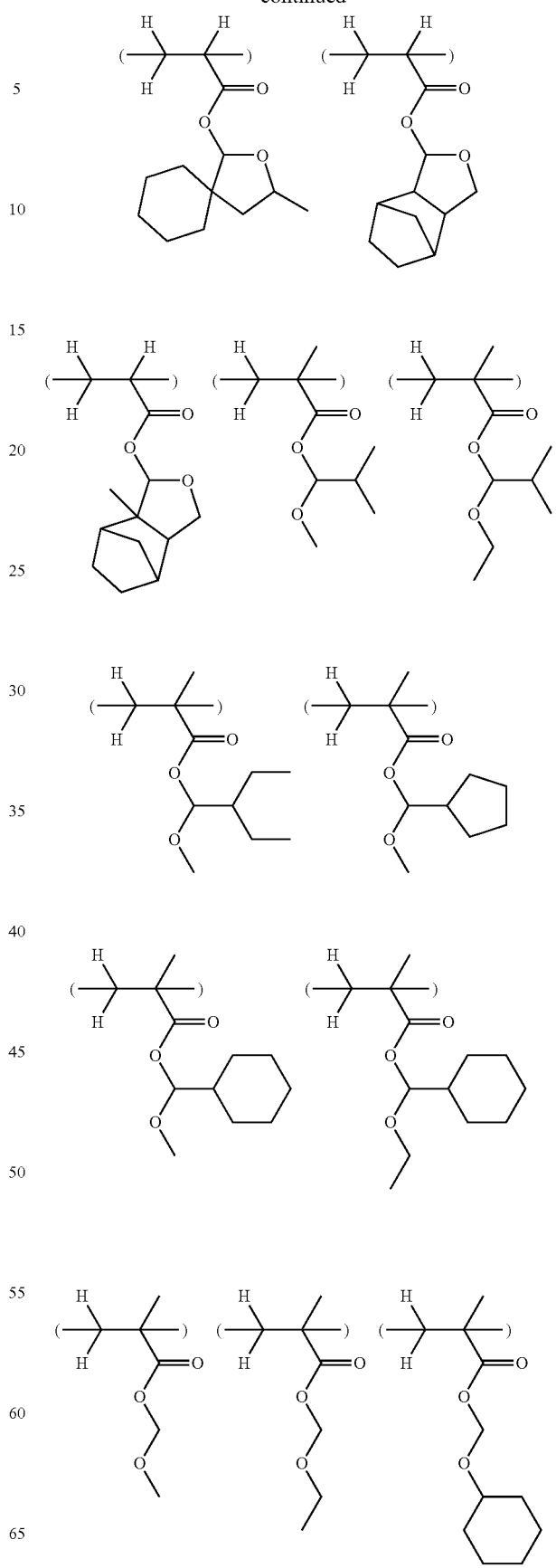

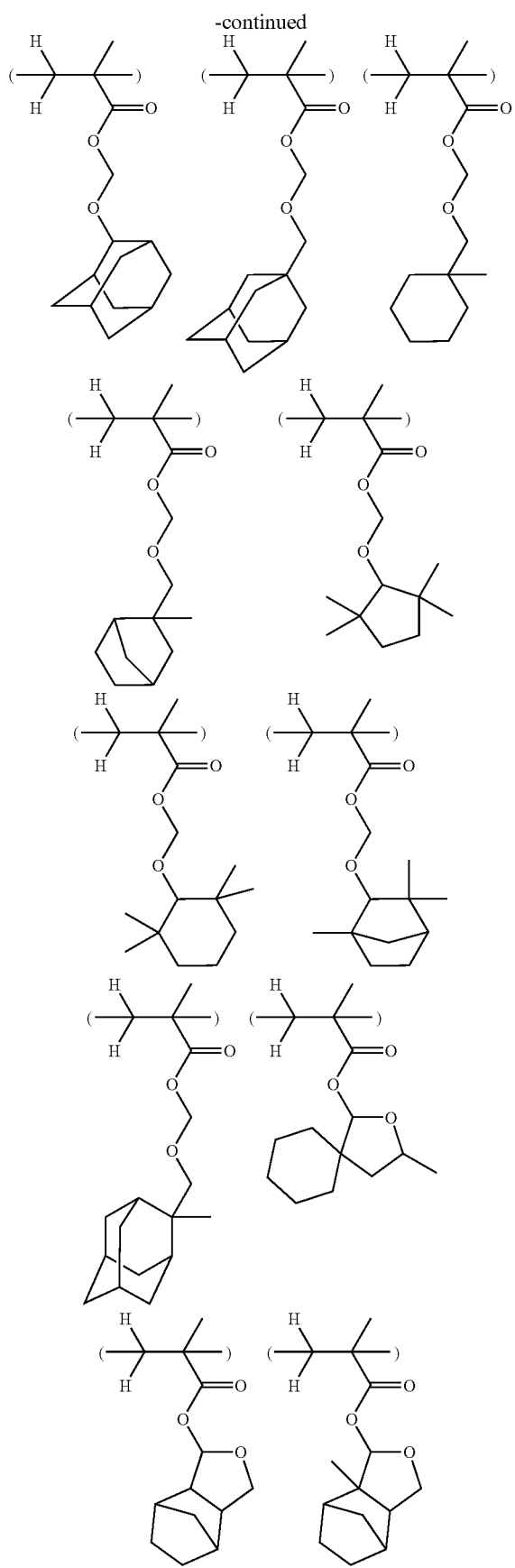

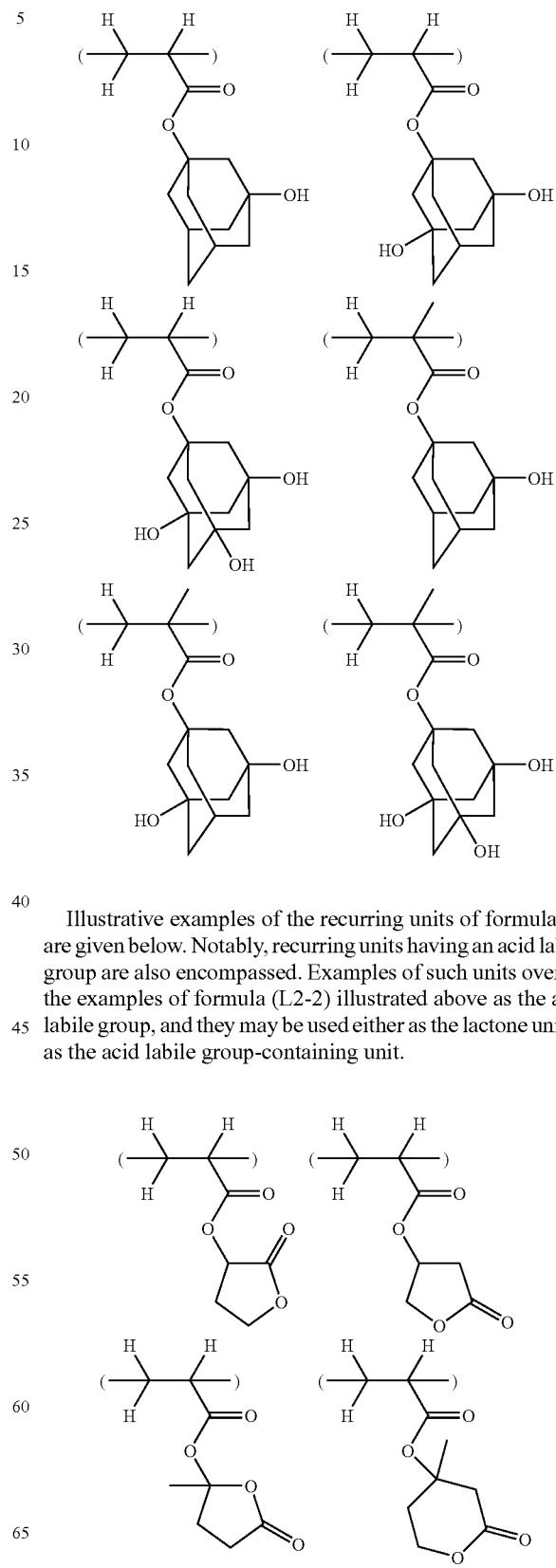

Illustrative, non-limiting examples of the recurring units of formula (3) are given below.

Illustrative examples of the recurring units of formula (4) are given below. Notably, recurring units having an acid labile group are also encompassed. Examples of such units overlap the examples of formula (L2-2) illustrated above as the acid labile group, and they may be used either as the lactone unit or as the acid labile group-containing unit.

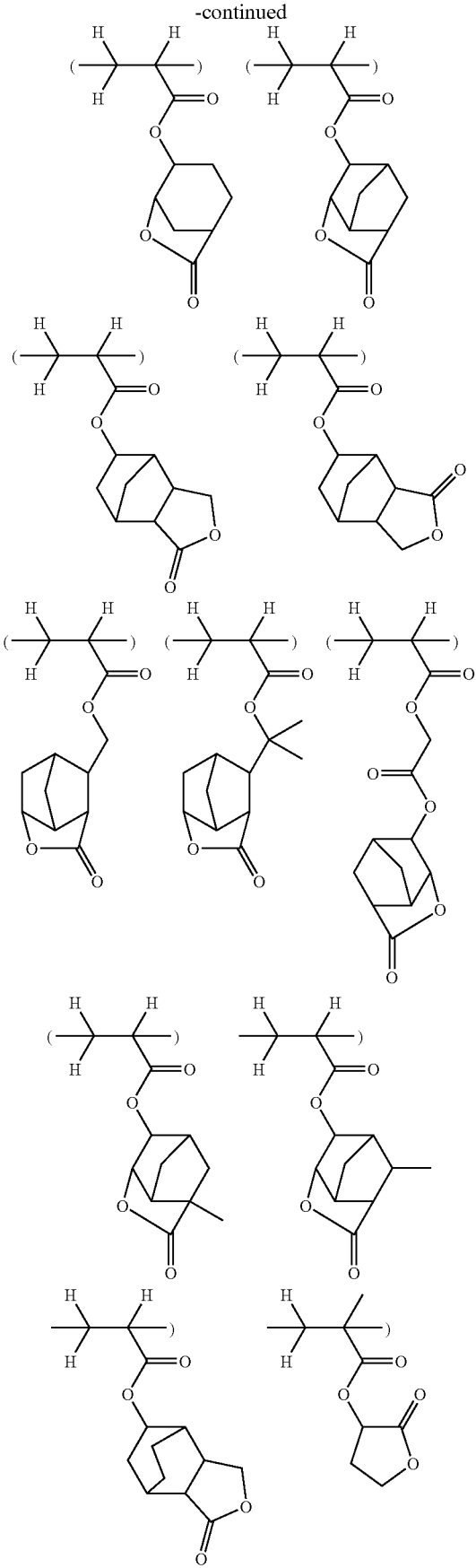
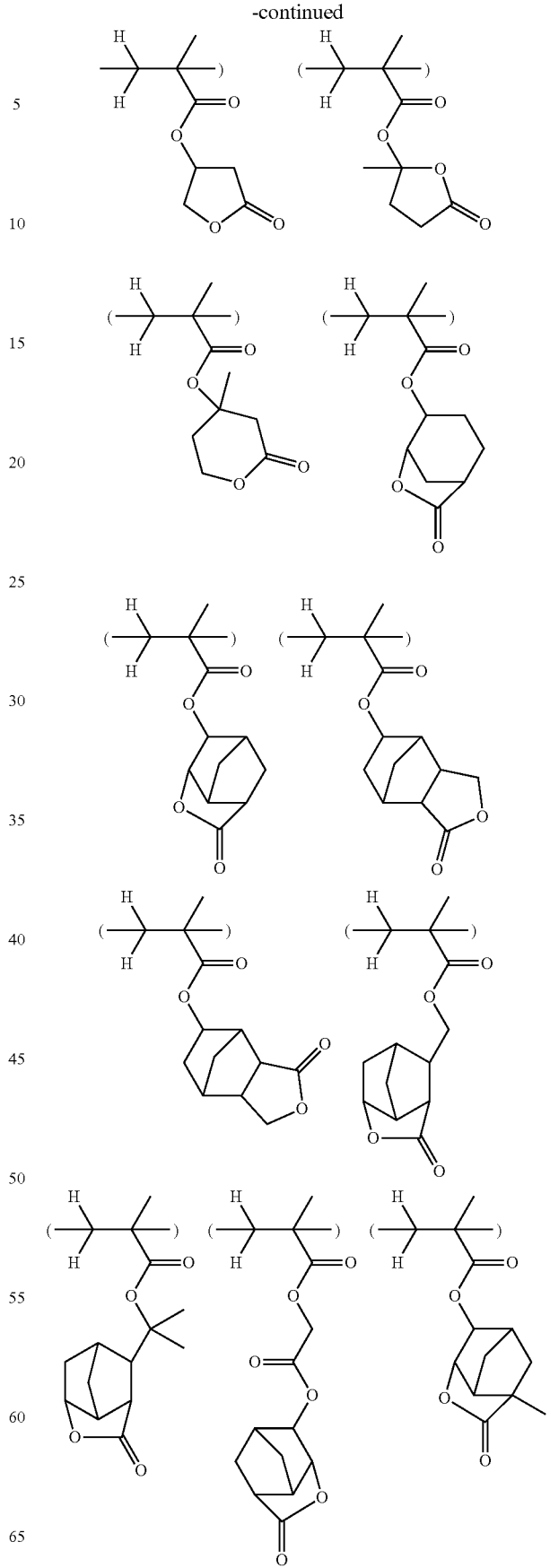

-continued
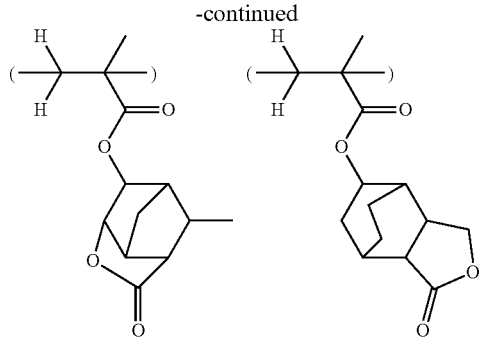
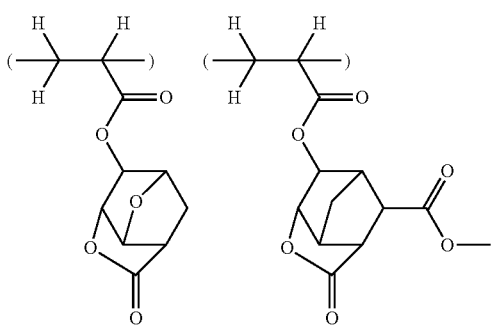
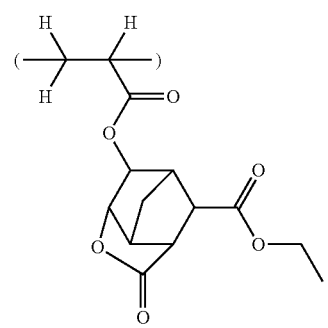
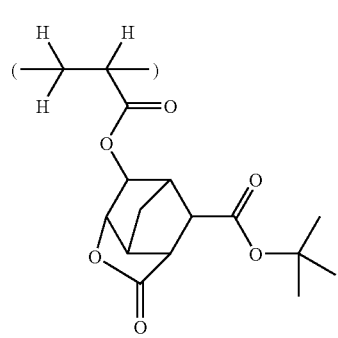
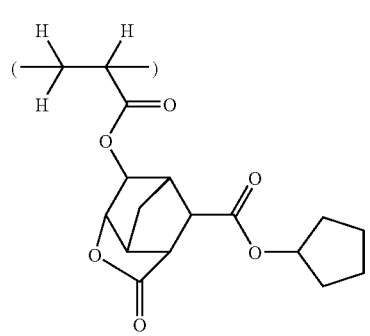
-continued
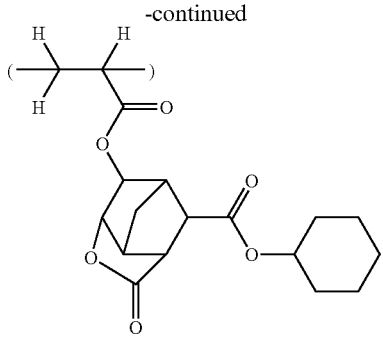
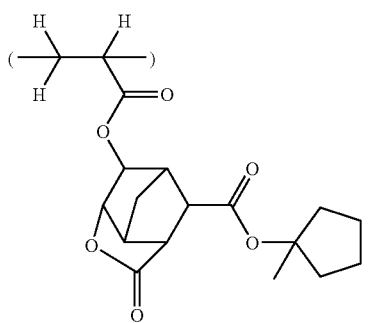
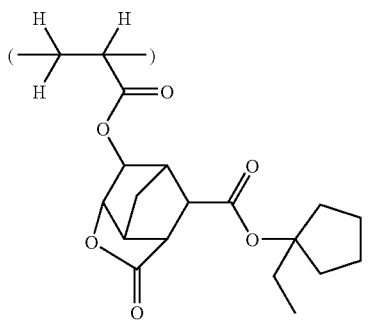
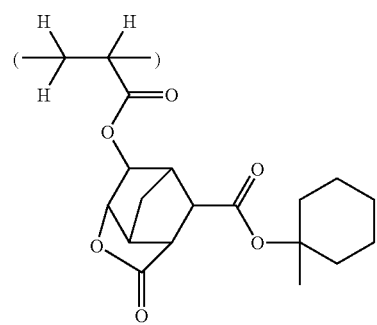
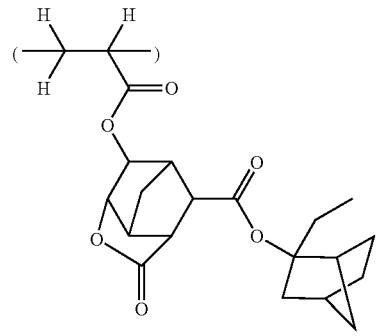

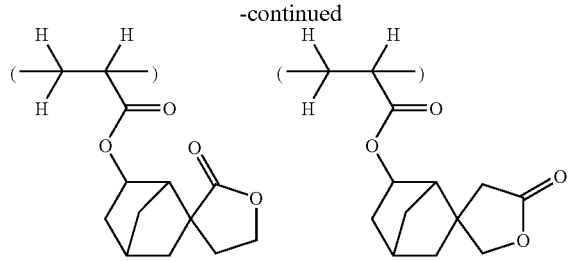
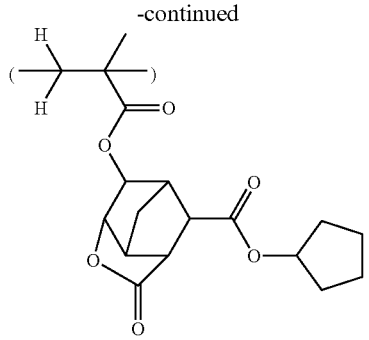
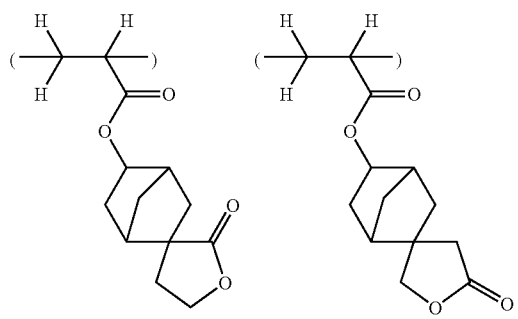
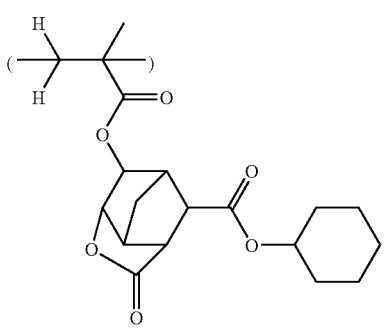
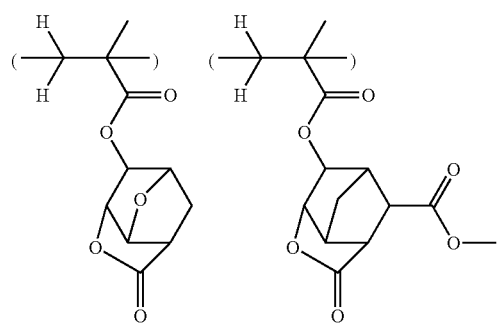
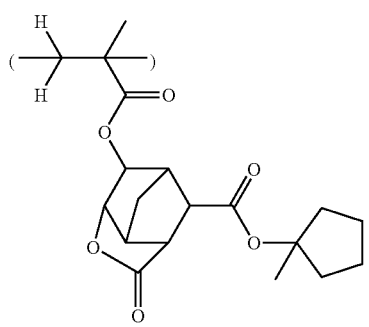
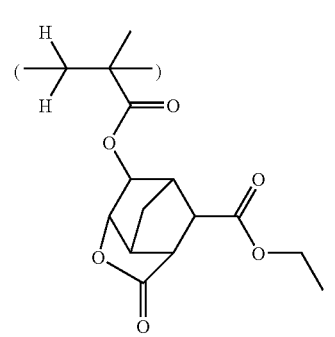
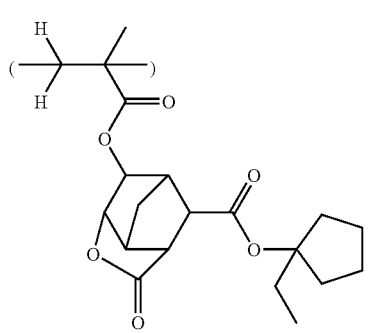
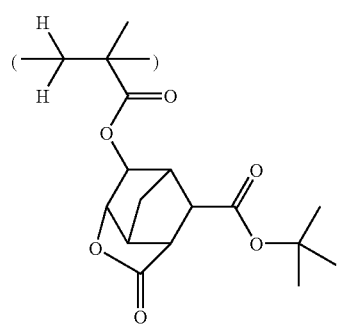
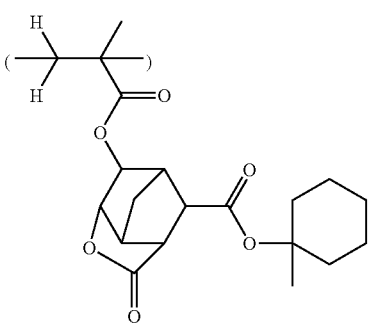

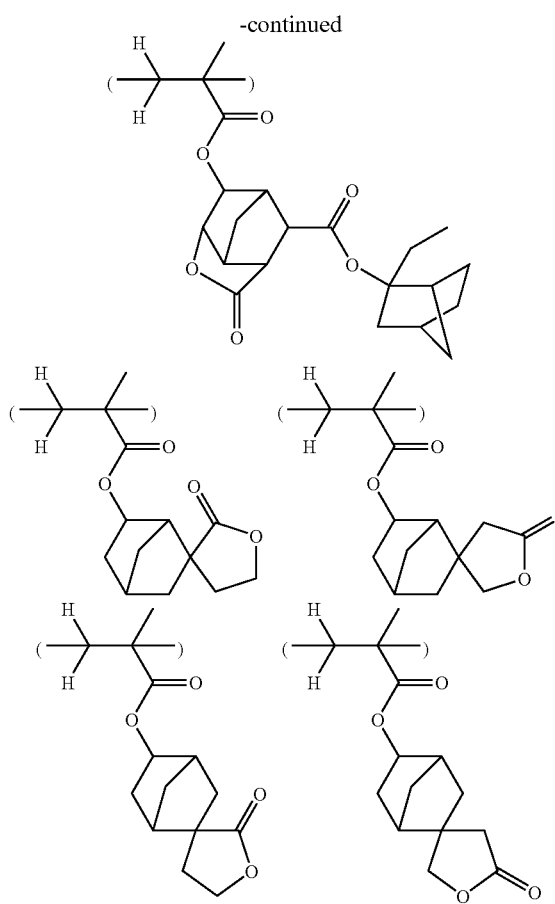

Also, units of the general formula (5L-1) may be advantageously used.

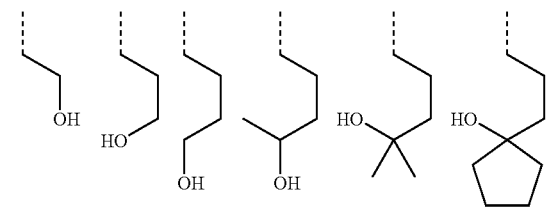

In formula (5L-1), $R^1$ is hydrogen, fluorine, methyl or trifluoromethyl, and preferably methyl. $R^{5'}$ is hydrogen or $CO_2R^{5''}$ wherein $R^{5''}$ is hydrogen, halogen or a straight, branched or cyclic $C_1$-$C_{15}$ monovalent hydrocarbon group which may have oxygen. W' is $CH_2$, O or S. M' is an integer of 1 to 3.

Examples of $R^{5''}$ include hydrogen, methyl, ethyl, n-propyl, isopropyl, n-butyl, sec-butyl, isobutyl, tert-butyl, cyclopentyl, cyclohexyl, 1-methylcyclopentyl, 1-ethylcyclopentyl, 1-methylcyclohexyl, 1-ethylcyclohexyl, 2-ethylhexyl, n-octyl, 2-methylbicyclo[2.2.1]heptan-2-yl, 2-ethylbicyclo[2.2.1]heptan-2-yl, 2-methyladamantan-2-yl, 2-ethyladamantan-2-yl, 8-methyltricyclo[5.2.1.0$^{2,6}$]decan-8-yl, 8-ethyltricyclo[5.2.1.0$^{2,6}$]decan-8-yl, 4-methyltetracyclo[6.2.1.1$^{3,6}$.0$^{2,7}$]dodecan-4-yl, 4-ethyltetracyclo[6.2.1.1$^{3,6}$.0$^{2,7}$]dodecan-4-yl, methoxymethyl, ethoxymethyl, methoxyethyl, ethoxyethyl, and methoxyethoxyethyl, as well as the groups shown below.

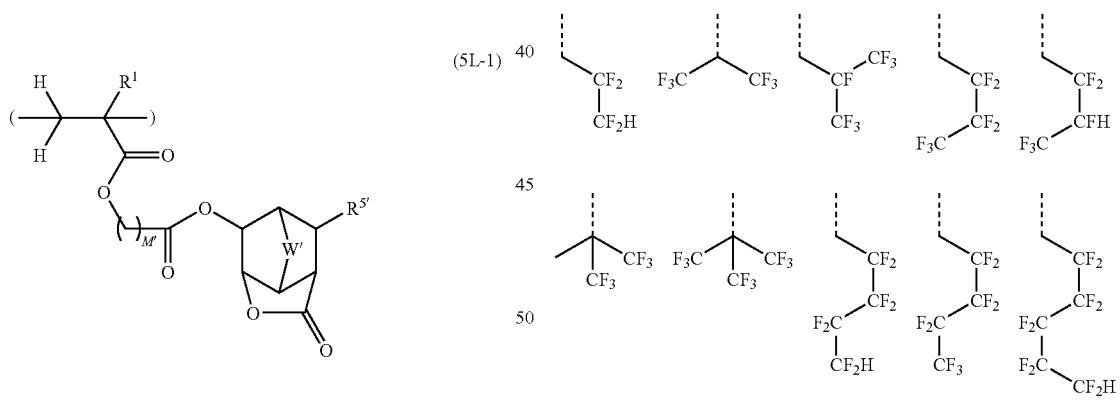

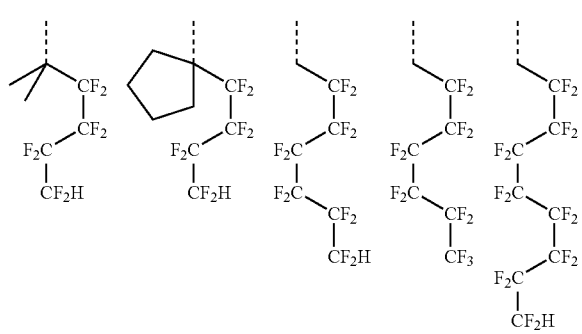

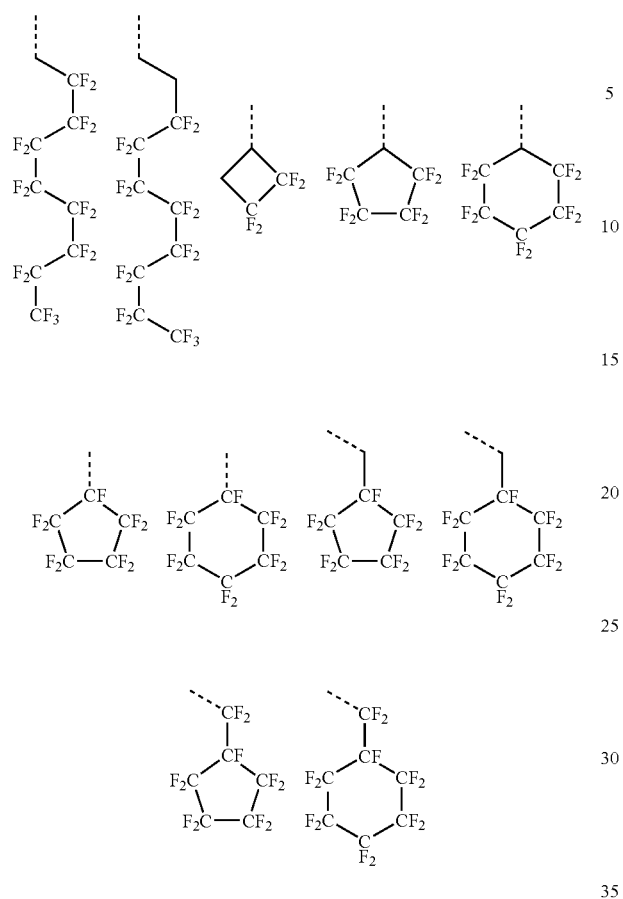

(The broken line denotes a valence bond.)

Preferred examples of $R^{5''}$ include methyl, 1-methylcyclopentyl, 1-ethylcyclopentyl, 1-methylcyclohexyl, 1-ethylcyclohexyl, 2-methyladamantan-2-yl, 2-ethyladamantan-2-yl, 8-methyltricyclo[5.2.1.0$^{2,6}$]decan-8-yl, 8-ethyltricyclo[5.2.1.0$^{2,6}$]decan-8-yl, 4-ethyltetracyclo[6.2.1.1$^{3,6}$.0$^{2,7}$]dodecan-4-yl.

Preferably W' is $CH_2$.

Examples of suitable monomers from which recurring units of formula (5L-1) are derived are given below.

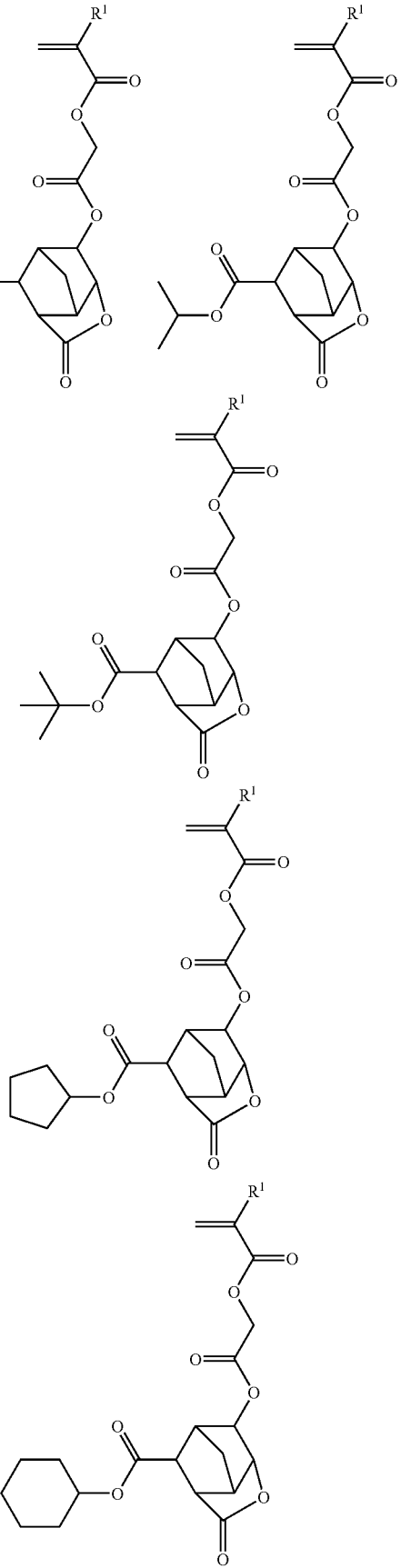

-continued
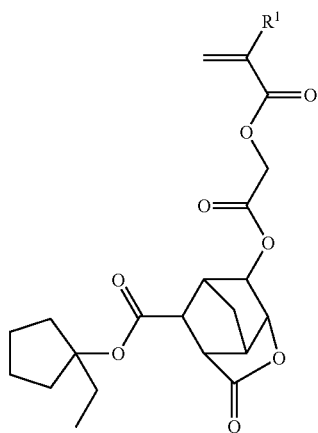
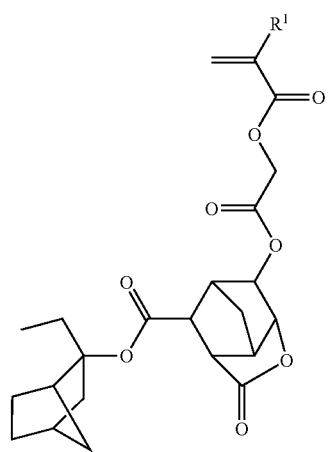
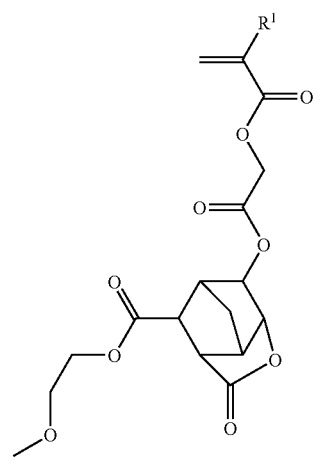
-continued
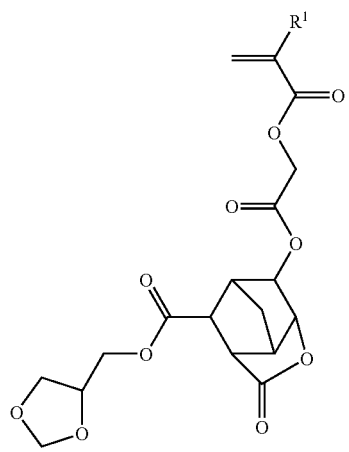
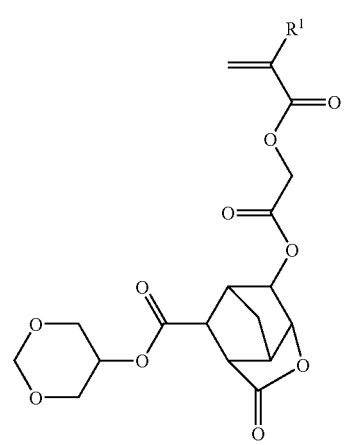
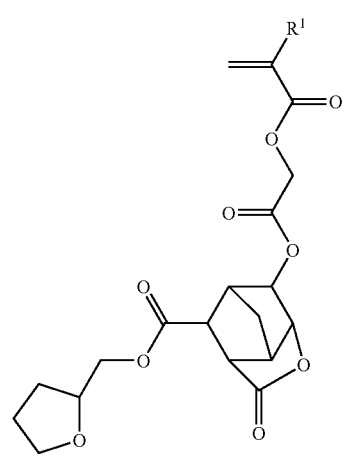

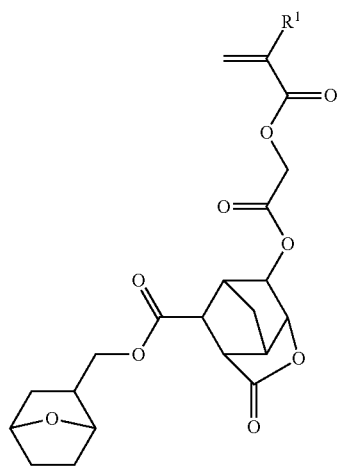
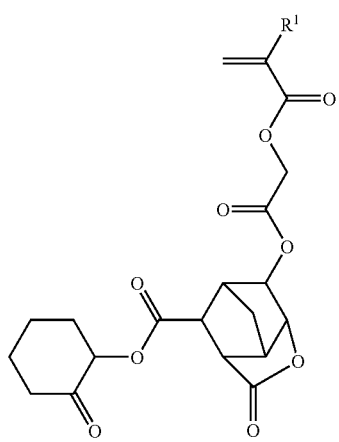
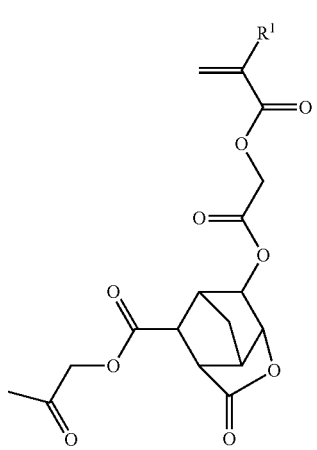
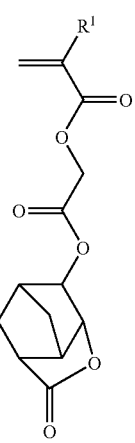
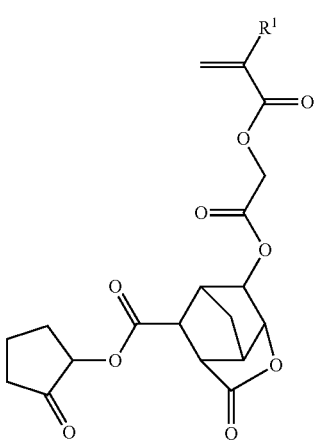
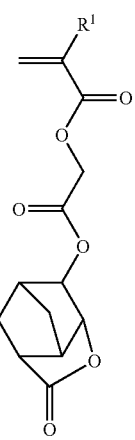

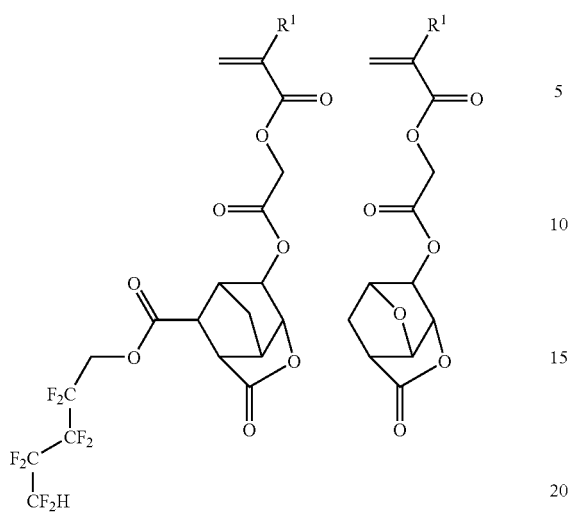
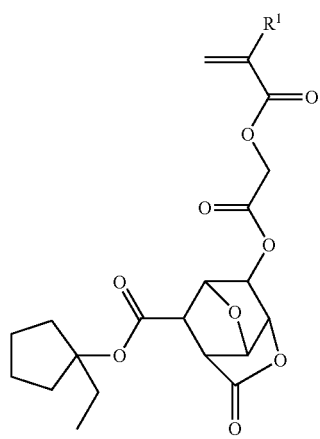
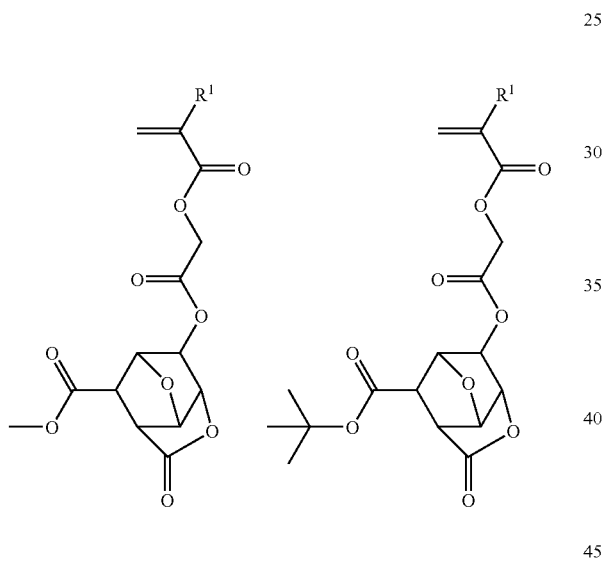
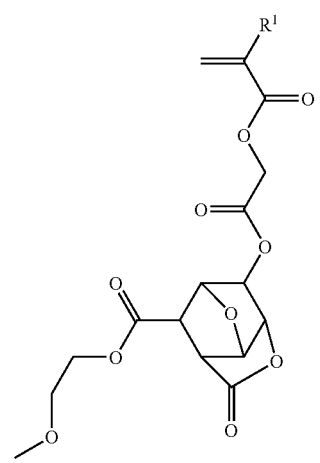
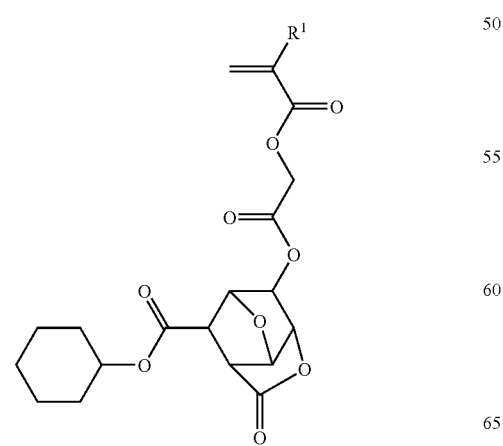
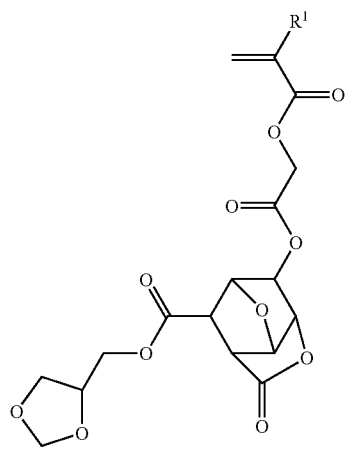

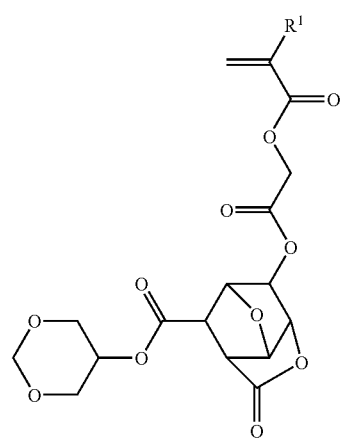
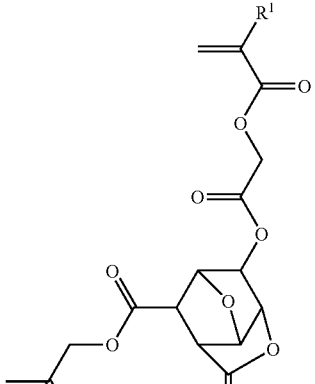
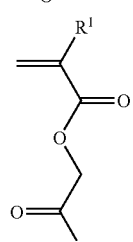
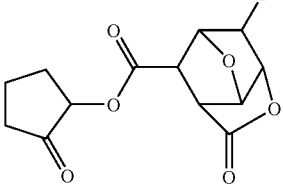
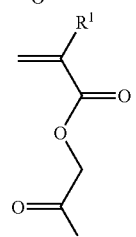
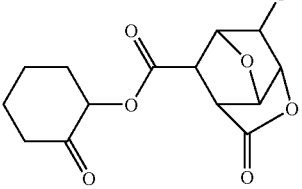
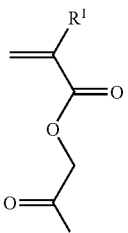
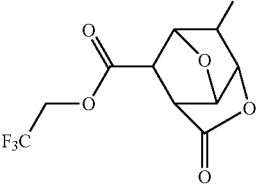

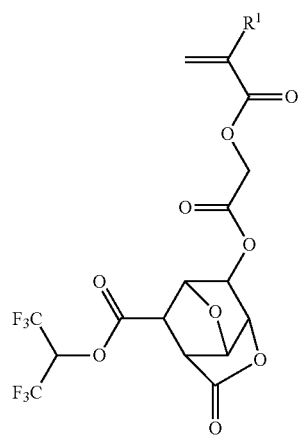

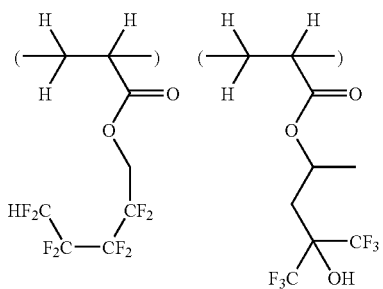

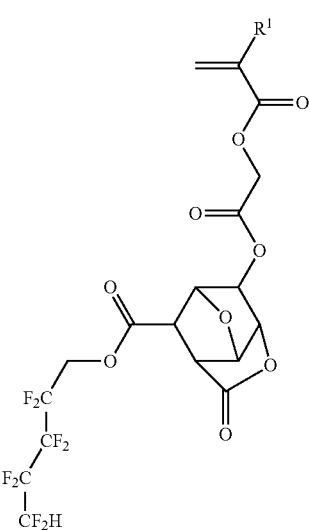

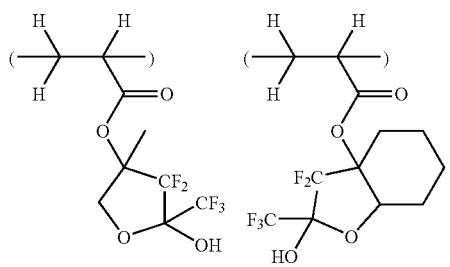

Herein R¹ is as defined above.

Of the monomers from which recurring units of formula (5L-1) are derived, those monomers wherein M'=1 are described in JP-A 2008-031298. Those monomers wherein M'=3 may be similarly synthesized aside from using chlorobutyric chloride instead of chloroacetyl chloride used as the reactant in the synthesis of the compounds wherein M'=1.

Illustrative examples of the recurring units of formula (5) are given below.

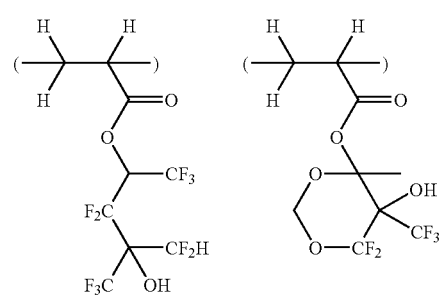

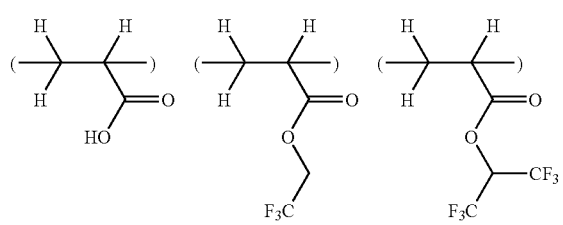

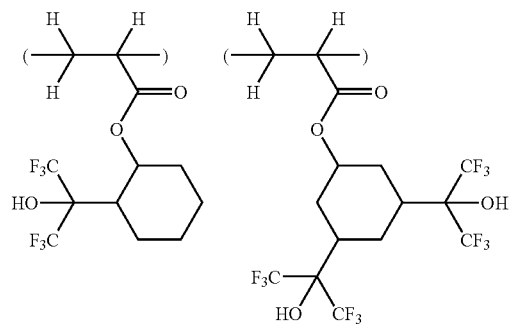

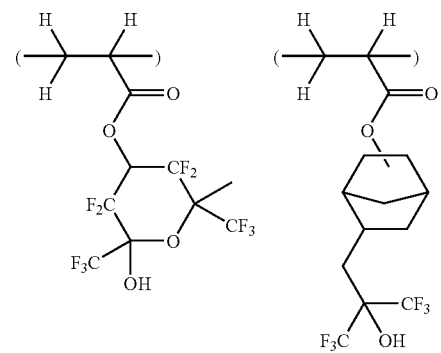

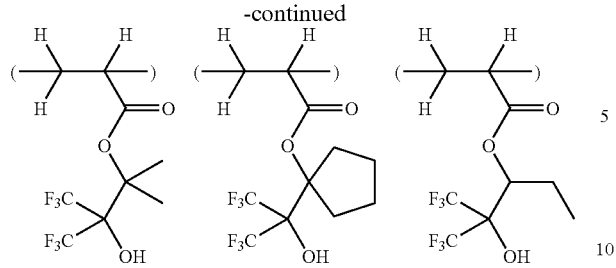
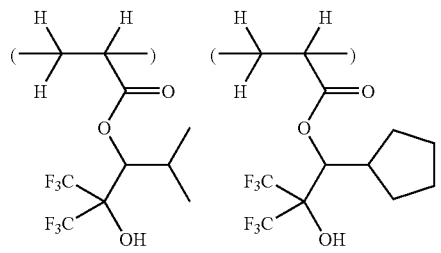
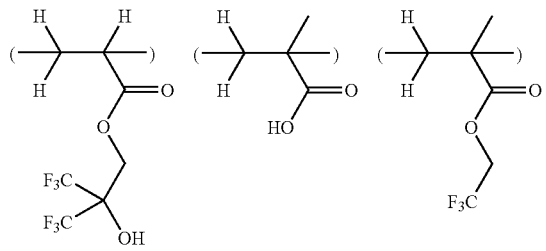
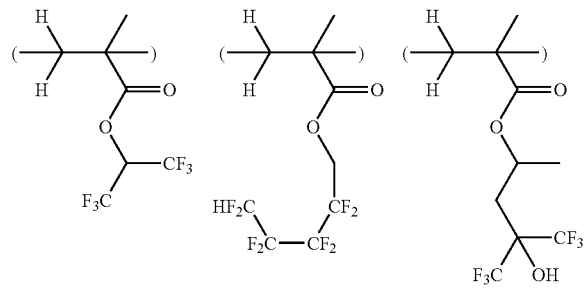
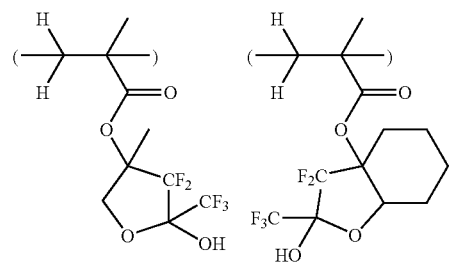
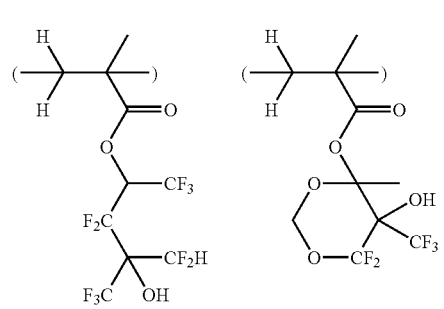
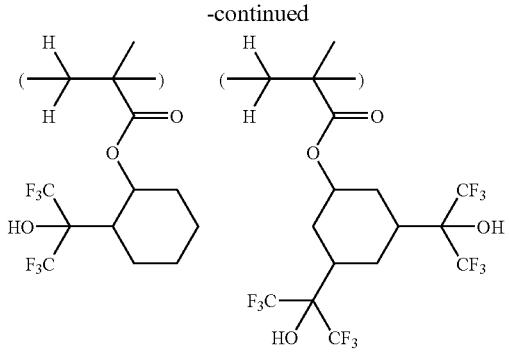
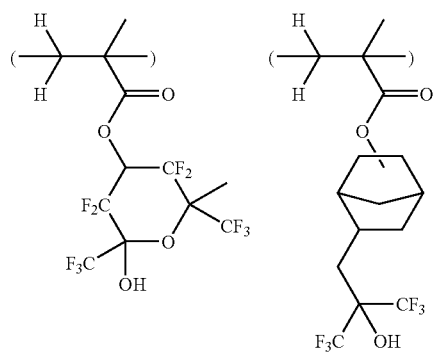
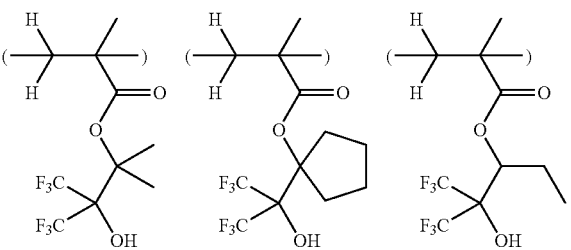
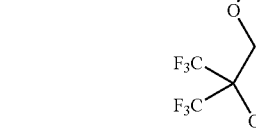

Illustrative examples of the recurring units of formula (6) are given below.

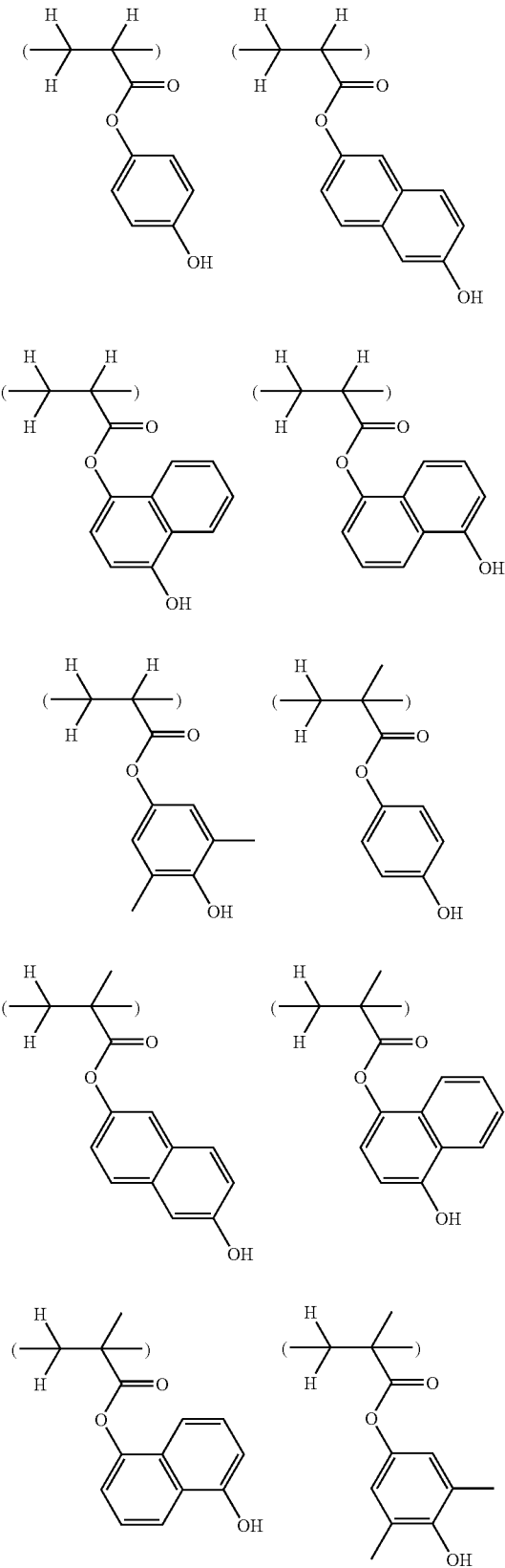
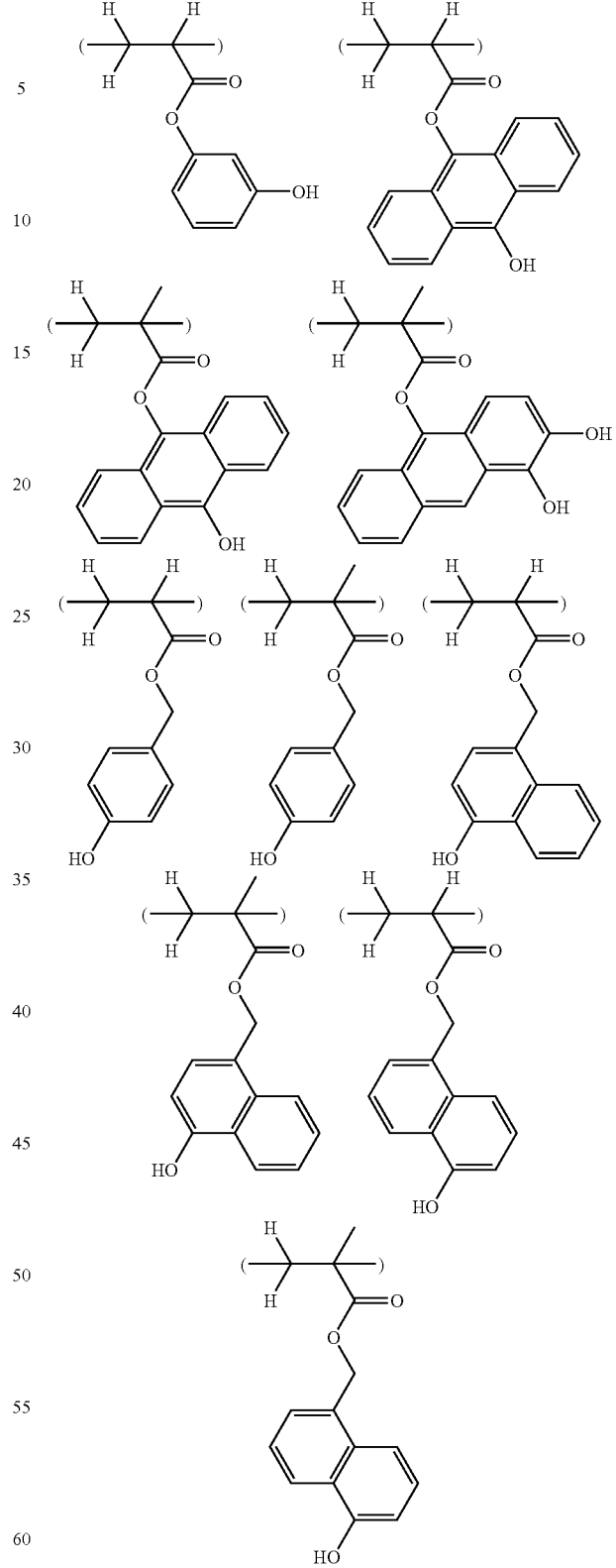

The polymer of the invention may further comprise recurring units derived from another monomer having a carbon-to-carbon double bond other than the foregoing. Examples of the additional monomer include substituted acrylates such as methyl methacrylate, methyl crotonate, dimethyl maleate, and dimethyl itaconate, unsaturated carboxylic acids such as maleic acid, fumaric acid and itaconic acid, cyclic olefins such as norbornene, norbornene derivatives, and tetracyclo [6.2.1.1$^{3,6}$.0$^{2,7}$]dodecene derivatives, unsaturated acid anhydrides such as itaconic anhydride, and other monomers.

The polymers of the invention are applicable not only to the ArF photolithography, but also to another lithography such as KrF, EB or EUV lithography.

In a still further embodiment, the polymer comprising recurring units of formula (1b) may further comprise recurring units of at least one type selected from the general formulae (7) to (11) and optionally, recurring units of at least one type selected from the general formulae (2) to (6).

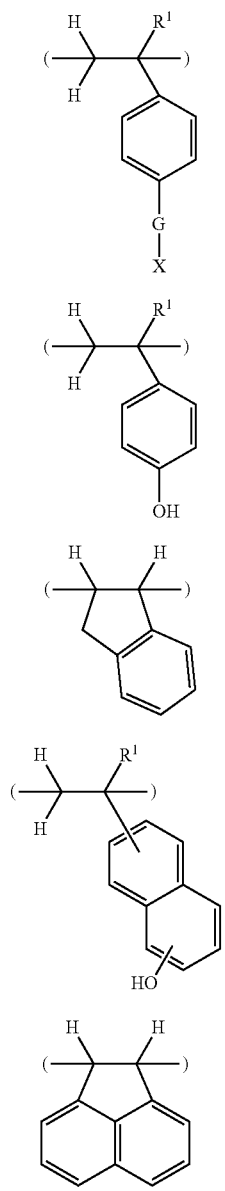

Herein R$^1$ and X are as defined above, and G is an oxygen atom or carbonyloxy group (—C(=O)O—).

Under the action of an acid, a polymer comprising recurring units of formula (7) is decomposed to generate a phenolic hydroxyl group and/or carboxylic acid whereby it becomes alkali soluble. The acid labile group X may be selected from a variety of such groups, for example, groups of formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms, as illustrated previously.

Illustrative non-limiting examples of the recurring units of formula (7) are given below.

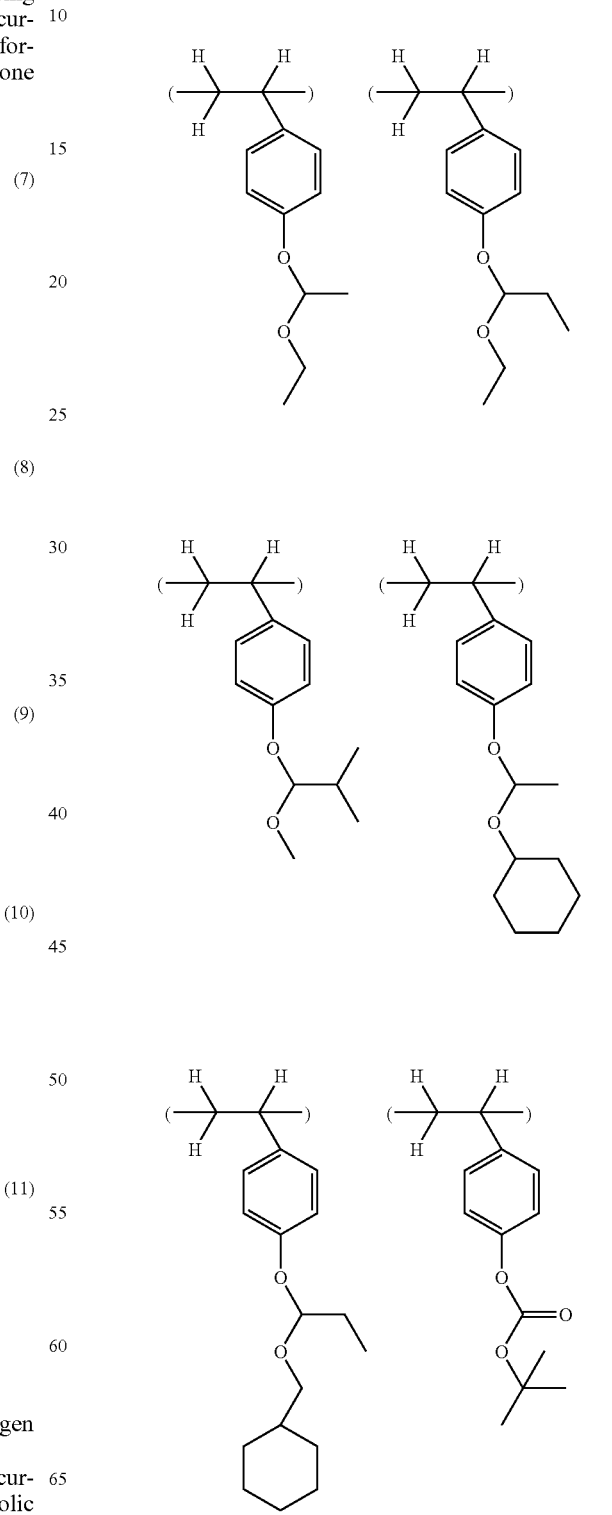

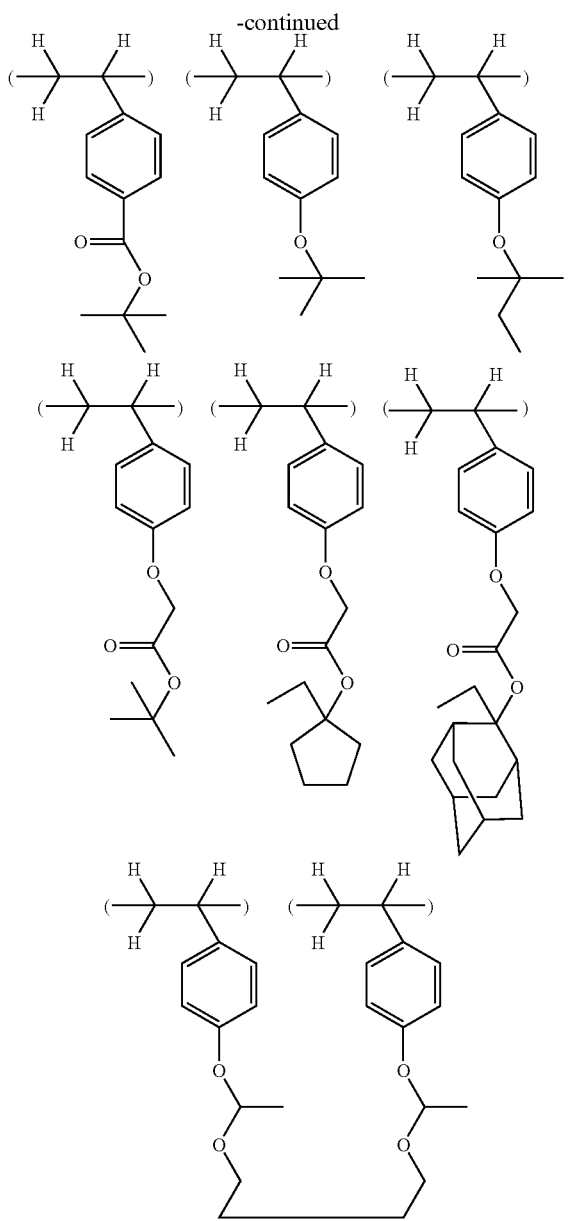

While hydroxyvinylnaphthalene of formula (10) may be substituted at arbitrary positions, typical substituted ones include 6-hydroxy-2-vinylnaphthalene and 4-hydroxy-1-vinylnaphthalene, with 6-hydroxy-2-vinylnaphthalene being preferred.

More preferred are those polymers comprising recurring units of any one type selected from formulae (7) to (11) and recurring units of formula (2) selected from among the recurring units of formulae (2) to (6).

The polymer of the invention comprising recurring units having a sulfonium salt with a polymerizable anion, and recurring units of any one or more type selected from formulae (2) to (6) and/or recurring units of any one or more type selected from formulae (7) to (11) may further comprise recurring units derived from another monomer having a carbon-to-carbon double bond other than the foregoing. Examples of the additional monomer include substituted acrylates such as methyl methacrylate, methyl crotonate, dimethyl maleate, and dimethyl itaconate, unsaturated carboxylic acids such as maleic acid, fumaric acid and itaconic acid, cyclic olefins such as norbornene, norbornene derivatives, tetracyclo[6.2.1.1$^{3,6}$.0$^{2,7}$]dodecene derivatives, and norbornadiens, unsaturated acid anhydrides such as itaconic anhydride, styrene, acenaphthylene, vinylnaphthalene, and other monomers.

The polymers have a weight average molecular weight (Mw) of 1,000 to 500,000, and preferably 3,000 to 100,000. Outside the range, a polymer may suffer an extreme drop of etching resistance or a reduced resolution due to a failure to provide a difference in dissolution rate before and after exposure. The measurement of molecular weight may be performed by gel permeation chromatography (GPC) versus polystyrene standards or a light scattering method.

In the inventive polymer, the preferred proportion of respective recurring units derived from discrete monomers may fall, for example, in the range (mol %) shown below, but is not limited thereto. The polymer may consist essentially of:

(I) from more than 0 mol % to 100 mol %, preferably 1 to 30 mol %, and more preferably 5 to 20 mol % of constituent units of one or more type having formula (1b) derived from monomer of formula (1);

(II) from 0 mol % to less than 100 mol %, preferably 70 to 99 mol %, and more preferably 80 to 95 mol % of constituent units of one or more type having formulae (2) to (6) and/or (7) to (11); and optionally (III) from 0 mol % to 80 mol %, preferably 0 to 70 mol %, and more preferably 0 to 50 mol % of constituent units of one or more type derived from the additional monomer(s).

The polymer may be prepared through copolymerization reaction using the compound of formula (1) as a first monomer and one or more compounds having a polymerizable double bond as second and subsequent monomers. Various modes of copolymerization reaction may be used for the preparation of the inventive polymer. The preferred modes are radical polymerization, anionic polymerization and coordination polymerization.

For radical polymerization, preferred reaction conditions include (a) a solvent selected from hydrocarbon solvents such as benzene, ether solvents such as tetrahydrofuran, alcohol solvents such as ethanol, and ketones such as methyl isobutyl ketone; (b) a polymerization initiator selected from azo compounds such as 2,2'-azobisisobutyronitrile and peroxides such as benzoyl peroxide and lauroyl peroxide; (c) a reaction temperature in the range of about 0° C. to about 100° C.; and (d) a reaction time in the range of about 0.5 to about 48 hours. Reaction parameters outside these ranges need not be excluded.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyllithium and sec-butyllithium, ketyl, and Grignard reagents, (c) a temperature of about −78° C. to about 0° C., (d) a time of about 0.5 to about 48 hours, and (e) a stopper selected from among proton-donative compounds such as methanol, halides such as methyl iodide, and electrophilic compounds. Reaction conditions outside the described range may be employed if desired.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about 0.5 hour to about 48 hours. Reaction conditions outside the described range may be employed if desired.

Once a polymer is prepared by any of the above-described procedures, it may be modified by deprotecting some or all acid labile groups so that the polymer may be used in negative resist compositions as will be described later. Into the polymer in which acid labile groups have been deprotected, different acid labile groups may be introduced again. This indicates that acid labile groups different from the acid labile groups initially introduced during polymerization are introduced into the polymer.

For example, once a polymer is formed through radical polymerization of 4-ethoxyethoxystyrene with a polymerizable anion-containing sulfonium salt of formula (1), the polymer may be tailored into a copolymer with hydroxystyrene by eliminating ethoxyethoxy groups from the polymer using acetic acid, pyridinium tosylate or the like. The tailored copolymer may be used as a base resin in negative resist compositions. By further reacting hydroxystyrene units of the copolymer with di-tert-butyl dicarbonate, tert-butyl chloroacetate, vinyl ether or the like, acid labile groups different from the acid labile groups (ethoxyethoxy) initially introduced during polymerization may be introduced into the copolymer.

It is also possible to synthesize a polymer of formula (1b) utilizing the above-mentioned method. Specifically, a polymer of formula (1b) may be synthesized by preparing a polymer by the above polymerization method, deprotecting some or all acid labile groups, then reacting the deprotected polymer with a sulfonium salt having a functional group reactive with the deprotected polymer.

For example, it is possible to introduce a polymerizable anion-containing sulfonium salt of formula (1) into a polymer by reacting under basic conditions triphenylsulfonium 2-(chloroacetoxy)-1,1,3,3,3-pentafluoro-2-hydroxypropanesulfonate with a polymer from which some or all acid labile groups have been deprotected. Notably, triphenylsulfonium 2-(chloroacetoxy)-1,1,3,3,3-pentafluoro-2-hydroxypropanesulfonate may be synthesized, as mentioned above, from triphenylsulfonium 1,1,3,3,3-pentafluoro-2-hydroxypropanesulfonate which has been synthesized by the inventors.

Reaction of chloroacetate with a phenolic polymer may be carried out in accordance with the teachings of JP 3796560, JP 3238465, and JP 3865048.

Resist Composition

The polymer of the invention is advantageously used as a base resin in a resist composition, and specifically a chemically amplified positive resist composition. Thus the invention provides a resist composition comprising the polymer, and especially a positive resist composition comprising the polymer. The positive resist composition preferably comprises:

(A) a base resin comprising the inventive polymer,
(B) an organic solvent, and optionally,
(C) an acid generator,
(D) a quencher, and
(E) a surfactant.

Also the polymer of the invention may be used as a base resin in a chemically amplified negative resist composition. The negative resist composition preferably comprises:

(A) a base resin comprising the inventive polymer,
(B) an organic solvent,
(F) a crosslinker for inducing crosslinkage under the action of an acid, and optionally,
(C) an acid generator,
(D) a quencher, and
(E) a surfactant.

For the positive resist composition, the base resin as component (A) may comprise another resin, specifically another polymer free of recurring units of formula (1b), having a dissolution rate in an alkaline developer that increases under the action of an acid, if desired, as well as the inventive polymer. Exemplary other resins include, but are not limited to, (i) poly(meth)acrylic acid derivatives, (ii) norbornene derivative/maleic anhydride copolymers, (iii) hydrogenated products of ring-opening metathesis polymerization (ROMP) polymers, (iv) vinyl ether/maleic anhydride/(meth)acrylic acid derivative copolymers, and (v) polyhydroxystyrene derivatives.

Of these, the poly(meth)acrylic acid derivatives (i) are polymers comprising units of formulae (2) to (6) and other units in combination. The polyhydroxystyrene derivatives (v) include polymers comprising units of formulae (7) to (11) in combination and polymers comprising units of formulae (2) to (11) in combination. In these polymers, a proportion of those units having acid labile groups, for example, monomer units of one or more types selected from among formulae (2) and (7) and a combination thereof is from more than 0 mole % to 80 mole %, preferably 1 to 50 mole %, and more preferably 10 to 40 mole %.

The hydrogenated products of ROMP (iii) are synthesized by the method illustrated in Examples of JP-A 2003-66612. Illustrative examples of such hydrogenated polymers include those polymers having the recurring units shown below, but are not limited thereto.

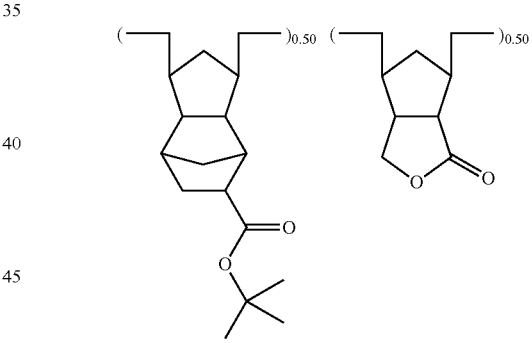

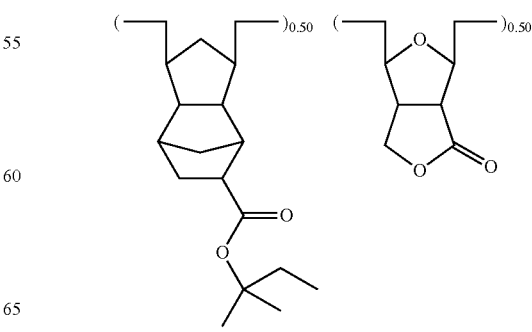

-continued
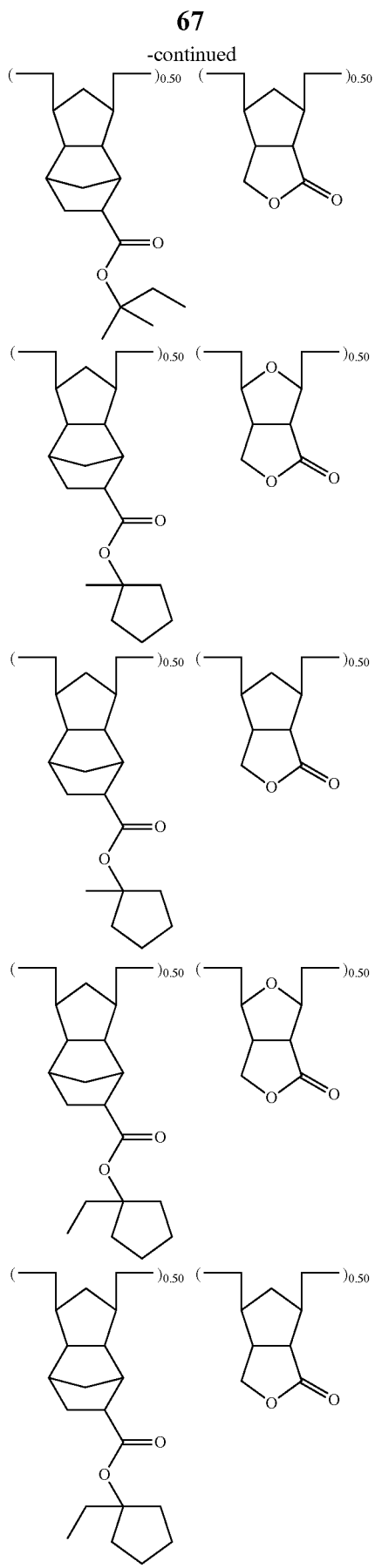
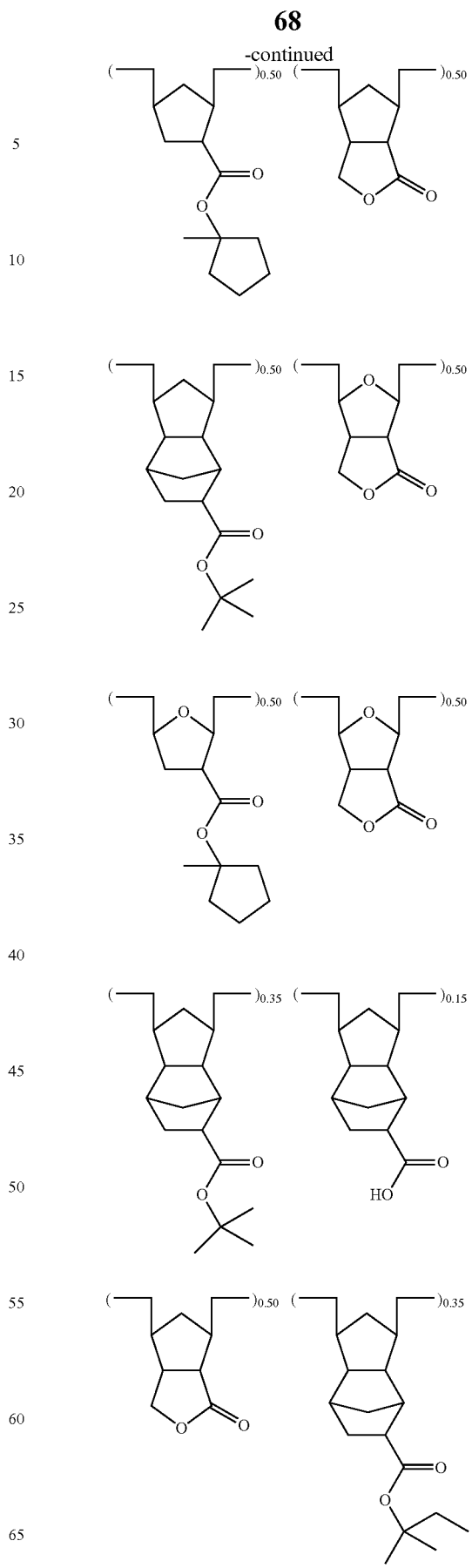

-continued
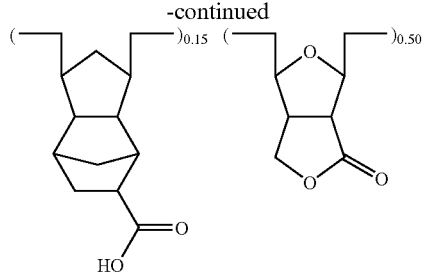
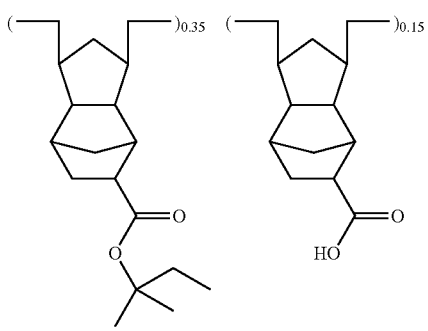
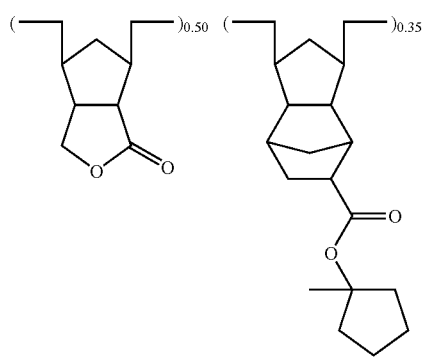
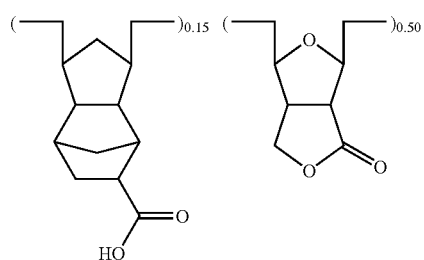
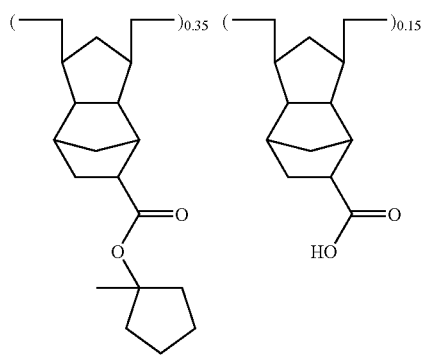
-continued
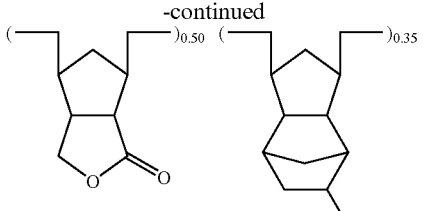
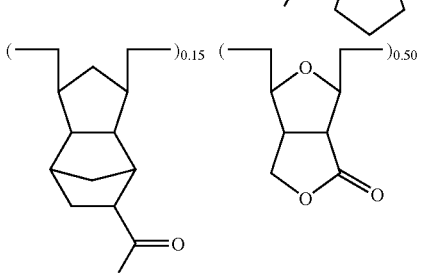
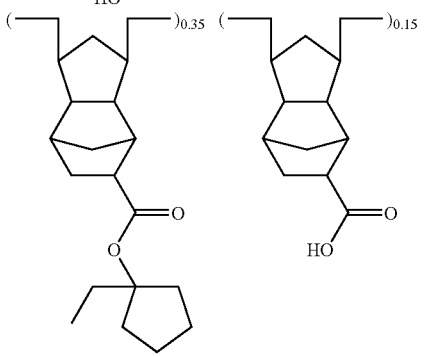
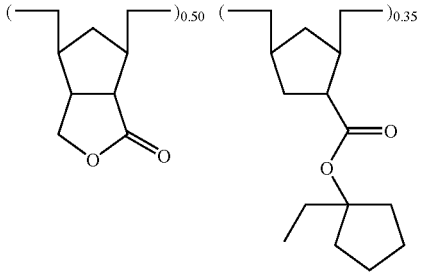
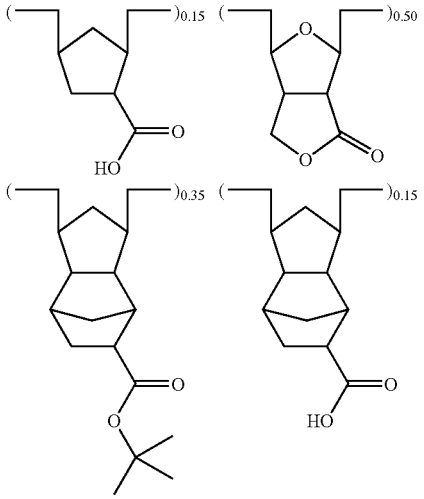

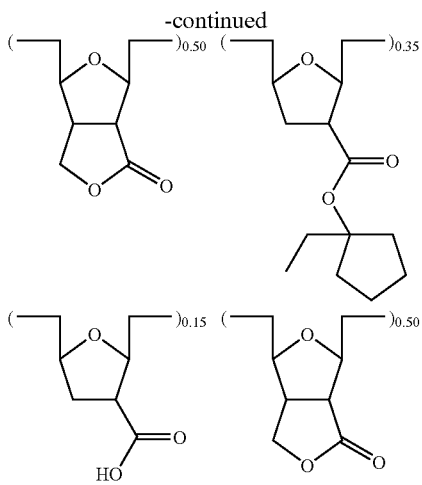

The inventive polymer and the other polymer are preferably blended in a weight ratio from 100:0 to 10:90, more preferably from 100:0 to 20:80. If the blend ratio of the inventive polymer is below this range, the resist composition would become poor in some of the desired properties. The properties of the resist composition can be adjusted by properly changing the blend ratio of the inventive polymer. The polymer is not limited to one type and a mixture of two or more polymers may be added. The use of plural polymers allows for easy adjustment of resist properties.

Organic Solvent

The organic solvent (B) used herein may be any organic solvent in which the base resin, acid generator, and other components are soluble. Illustrative, non-limiting, examples of the organic solvent include ketones such as cyclohexanone and methyl amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof. Of the above organic solvents, it is recommended to use diethylene glycol dimethyl ether, 1-ethoxy-2-propanol, propylene glycol monomethyl ether acetate, and mixtures thereof because the acid generator is most soluble therein.

An appropriate amount of the organic solvent used is to 1,000 parts, especially 400 to 800 parts by weight per parts by weight of the base resin.

Photoacid Generator

In the practice of the invention, an acid generator is optionally used as component (C). Where a photoacid generator is added as the acid generator, it may be any compound capable of generating an acid upon exposure to high-energy radiation. Suitable photoacid generators include sulfonium salts, iodonium salts, sulfonyldiazomethane, N-sulfonyloxyimide, and oxime-O-sulfonate acid generators. Exemplary acid generators are given below while they may be used alone or in admixture of two or more.

Sulfonium salts are salts of sulfonium cations with sulfonates, bis(substituted alkylsulfonyl)imides and tris (substituted alkylsulfonyl)methods. Exemplary sulfonium cations include triphenylsulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris (3-tert-butoxyphenyl)sulfonium, (3,4-di-tert-butoxyphenyl) diphenylsulfonium, bis(3,4-di-tert-butoxyphenyl) phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 4-methylphenyldiphenylsulfonium, 4-tert-butylphenyldiphenylsulfonium, bis(4-methylphenyl)phenylsulfonium, bis(4-tert-butylphenyl)phenylsulfonium, tris(4-methylphenyl)sulfonium, tris(4-tert-butylphenyl)sulfonium, tris(phenylmethyl)sulfonium, 2-naphthyldiphenylsulfonium, dimethyl(2-naphthyl)sulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxopropylthiacyclopentanium, 2-oxobutylthiacyclopentanium, 2-oxo-3,3-dimethylbutylthiacyclopentanium, 2-oxo-2-phenylethylthiacyclopentanium, 4-n-butoxynaphthyl-1-thiacyclopentanium, and 2-n-butoxynaphthyl-1-thiacyclopentanium.

Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, 1,1,2,2-tetrafluoro-2-(tetracyclo[6.2.1.1$^{3,6}$.0$^{2,7}$]dodec-3-en-8-yl) ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yloxycarbonyl)

difluoromethanesulfonate, and 4-oxo-1-adamantyloxycarbonyldifluoromethanesulfonate.

Exemplary bis(substituted alkylsulfonyl)imides include bis(trifluoromethylsulfonyl)imide, bis(pentafluoroethylsulfonyl)imide, bis(heptafluoropropylsulfonyl)imide, and perfluoro(1,3-propylenebissulfonyl)imide. A typical tris(substituted alkylsulfonyl)methide is tris(trifluoromethylsulfonyl)methide. Sulfonium salts based on combination of the foregoing examples are included.

Iodonium salts are salts of iodonium cations with sulfonates, bis(substituted alkylsulfonyl)imides and tris(substituted alkylsulfonyl)methods. Exemplary iodonium cations include diphenyliodinium, bis(4-tert-butylphenyl)iodonium, 4-tert-butoxyphenylphenyliodonium, and 4-methoxyphenylphenyliodonium. Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, 1,1,2,2-tetrafluoro-2-(tetracyclo[6.2.1.1$^{3,6}$.0$^{2,7}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yloxycarbonyl)difluoromethanesulfonate, and 4-oxo-1-adamantyloxycarbonyldifluoromethanesulfonate.

Exemplary bis(substituted alkylsulfonyl)imides include bis(trifluoromethylsulfonyl)imide, bis(pentafluoroethylsulfonyl)imide, bis(heptafluoropropylsulfonyl)imide, and perfluoro(1,3-propylenebissulfonyl)imide.

A typical tris(substituted alkylsulfonyl)methide is tris(trifluoromethylsulfonyl)methide. Iodonium salts based on combination of the foregoing examples are included.

N-sulfonyloxydicarboxylmide photoacid generators include combinations of imide skeletons with sulfonates. Exemplary imide skeletons are succinimide, naphthalenedicarboxylmide, phthalimide, cyclohexyldicarboxylmide, 5-norbornene-2,3-dicarboxylmide, and 7-oxabicyclo[2.2.1]-5-heptene-2,3-dicarboxylmide. Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, 1,1,2,2-tetrafluoro-2-(tetracyclo[6.2.1.1$^{3,7}$.0$^{2,7}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yloxycarbonyl)difluoromethanesulfonate, and 4-oxo-1-adamantyloxycarbonyldifluoromethanesulfonate.

Also useful are O-arylsulfonyl oxime and O-alkylsulfonyl oxime (oxime sulfonate) photoacid generators.

They include oxime sulfonate compounds having an electron-withdrawing group (e.g., trifluoromethyl) for increased stability, as represented by the formula (Ox-1):

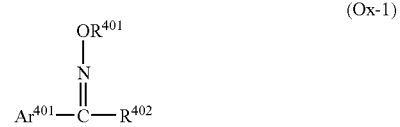

(Ox-1)

wherein $R^{401}$ is a substituted or unsubstituted $C_1$-$C_{10}$ haloalkylsulfonyl or halobenzenesulfonyl group, $R^{402}$ is a $C_1$-$C_{11}$ haloalkyl group, and $Ar^{401}$ is a substituted or unsubstituted aromatic or hetero-aromatic group.

Examples include 2-[2,2,3,3,4,4,5,5-octafluoro-1-(nonafluorobutylsulfonyloxyimino)pentyl]fluorene, 2-[2,2,3,3,4,4-pentafluoro-1-(nonafluorobutylsulfonyloxyimino)butyl] fluorene, 2-[2,2,3,3,4,4,5,5,6,6-decafluoro-1-(nonafluorobutylsulfonyloxyimino)hexyl]fluorene, 2-[2,2,3,3,4,4,5,5-octafluoro-1-(nonafluorobutylsulfonyloxyimino)pentyl]-4-biphenyl, 2-[2,2,3,3,4,4-pentafluoro-1-(nonafluorobutylsulfonyloxyimino)butyl]-4-biphenyl, and 2-[2,2,3,3,4,4,5,5,6,6-decafluoro-1-(nonafluorobutylsulfonyloxyimino)hexyl]-4-biphenyl. Also included are modified forms of the foregoing compounds having substituted on their skeleton 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yloxycarbonyl)difluoromethanesulfonate, and 4-oxo-1-adamantyloxycarbonyldifluoromethanesulfonate.

Among others, acid generators having the general formula (C)-1 are preferred.

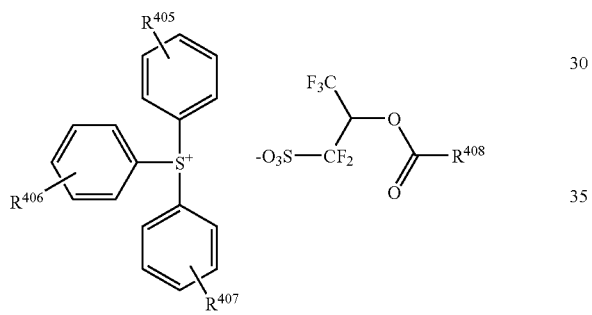

(C)-1

Herein $R^{405}$, $R^{406}$, and $R^{407}$ are each independently hydrogen or a straight, branched or cyclic, monovalent $C_1$-$C_{20}$ hydrocarbon group, typically an alkyl or alkoxy group, which may contain a heteroatom. Examples of hydrocarbon groups optionally containing a heteroatom include methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, butyladamantyl, and modified forms of the foregoing in which any carbon-to-carbon bond is separated by a hetero-atomic grouping such as —O—, —S—, —SO—, —SO$_2$—, —NH—, —C(=O)—, —C(=O)O—, or —C(=O)NH—, or any hydrogen atom is replaced by a functional group such as —OH, —NH$_2$, —CHO, or —CO$_2$H. $R^{408}$ is a straight, branched or cyclic, monovalent $C_7$-$C_{30}$ hydrocarbon group which may contain a heteroatom, examples of which are exemplified below, but are not limited thereto.

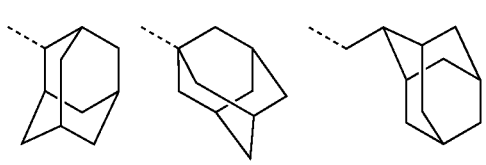

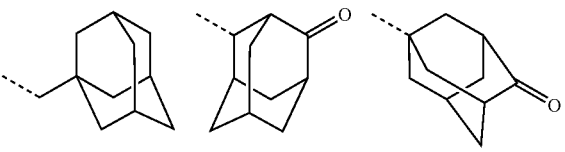

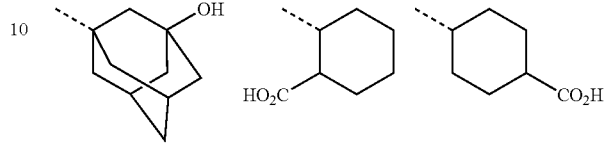

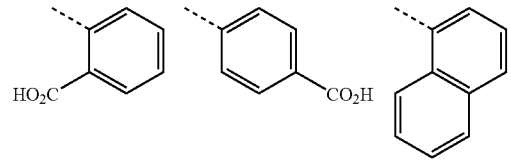

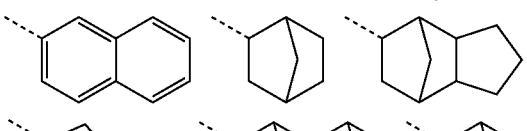

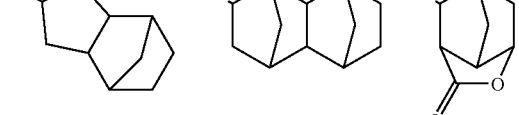

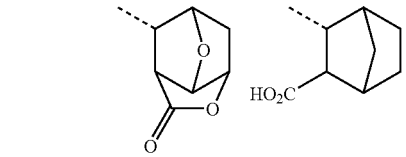

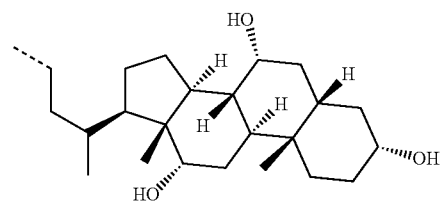

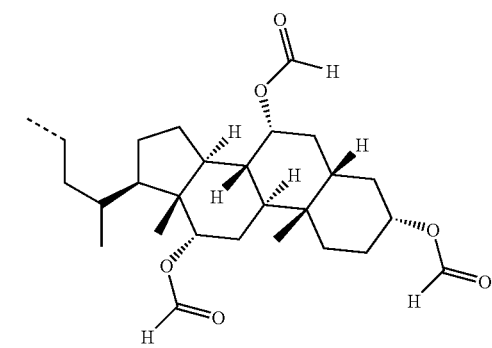

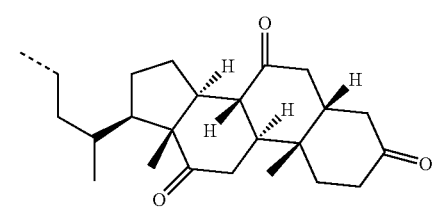

Illustrative examples of acid generators (C)-1 are shown below.
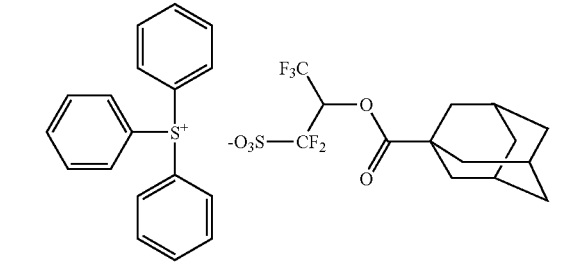
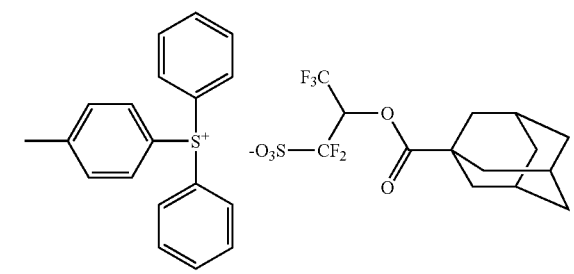
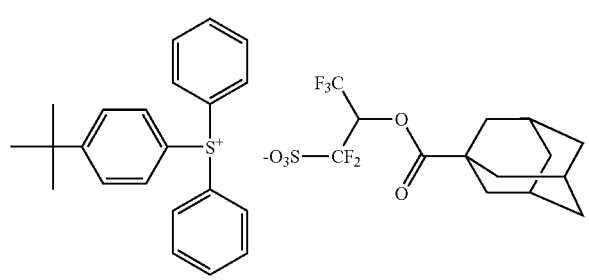
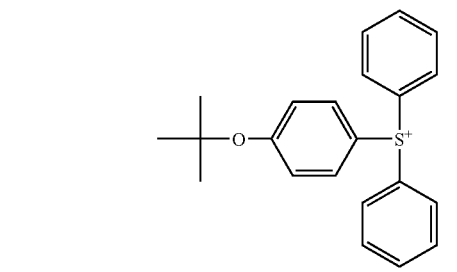
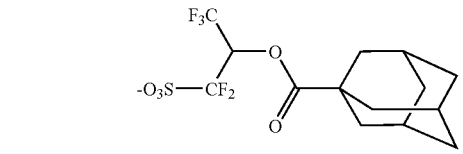
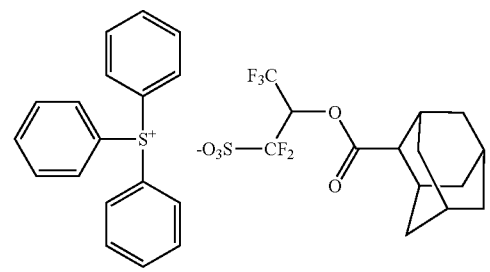
-continued
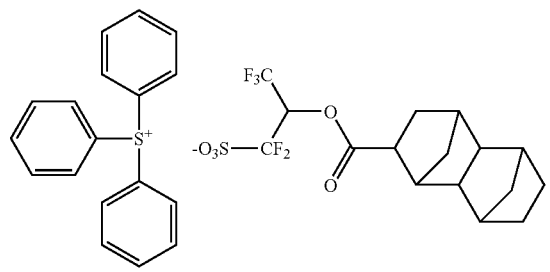
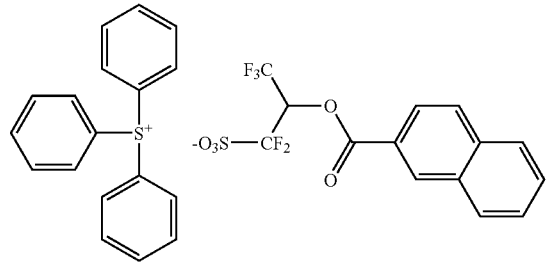
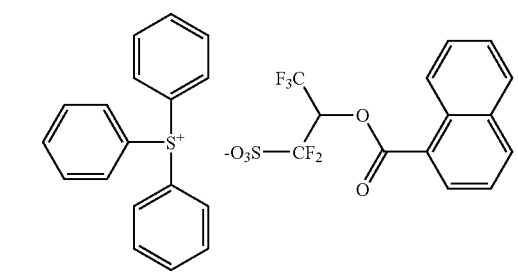
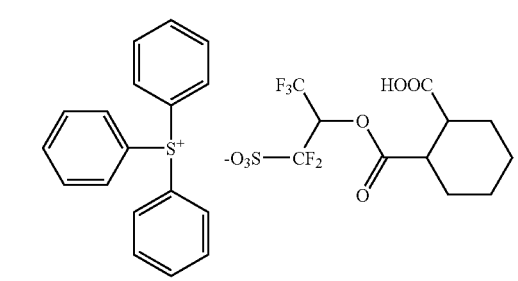
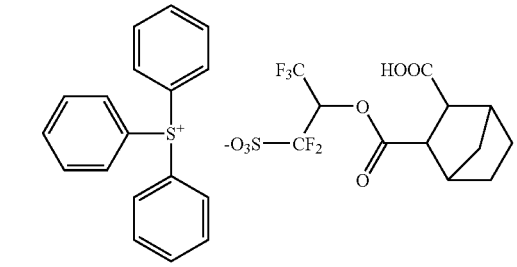
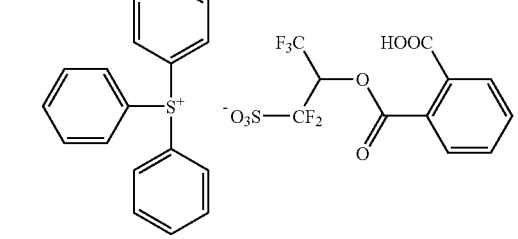

-continued

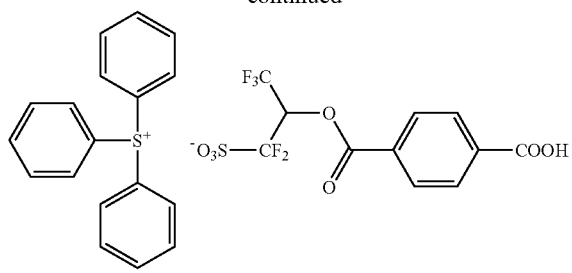
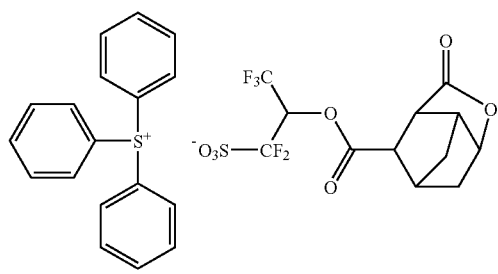
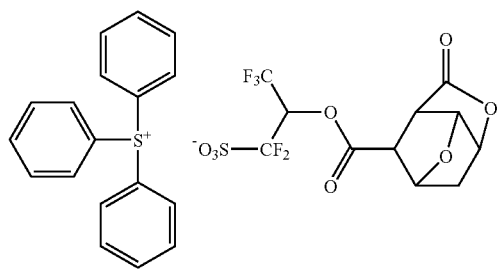
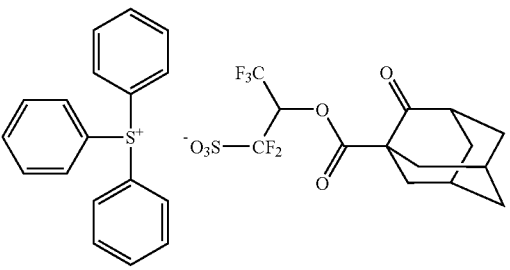
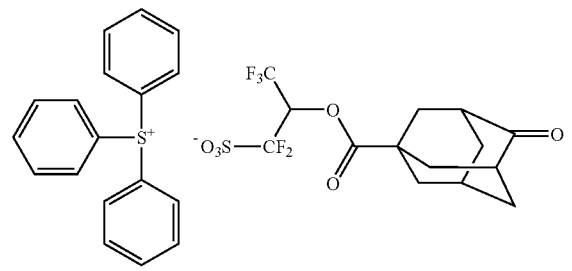
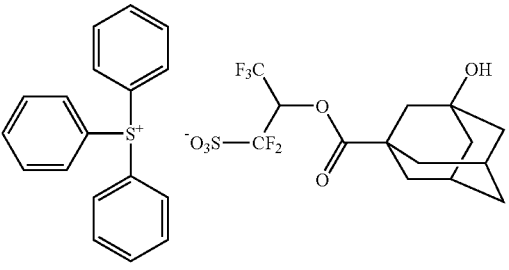

-continued

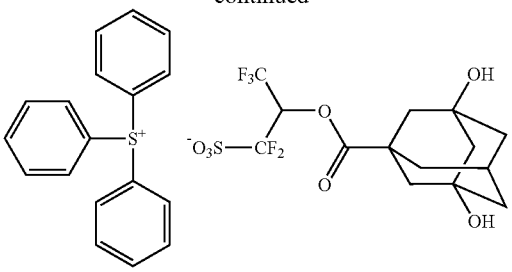
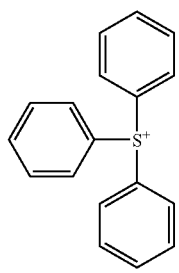
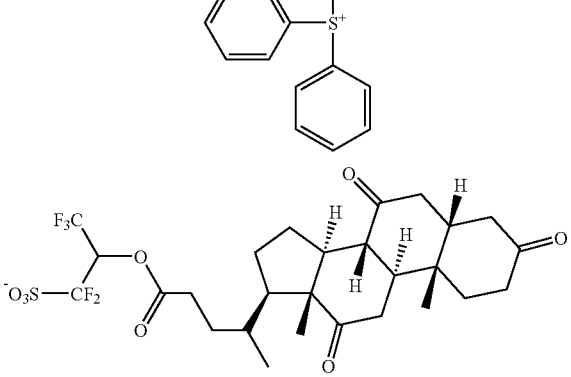

In the chemically amplified resist composition, the photoacid generator (C) may be added in any desired amount as long as the objects of the invention are not compromised. An appropriate amount of the photoacid generator (C), when added, is 0.1 to 10 parts, and more preferably 0.1 to 5 parts by weight per 100 parts by weight of the base resin in the composition. Too high a proportion of the photoacid generator (C) may give rise to problems of degraded resolution and foreign matter upon development and resist film peeling. The photoacid generators (C) may be used alone or in admixture of two or more. The transmittance of the resist film can be controlled by using a photoacid generator having a low transmittance at the exposure wavelength and adjusting the amount of the photoacid generator added.

It is noted that an acid diffusion controlling function may be provided when two or more photoacid generators are used in admixture provided that one photoacid generator is an onium salt capable of generating a weak acid. Specifically, in a system using a mixture of a photoacid generator capable of generating a strong acid (e.g., fluorinated sulfonic acid) and an onium salt capable of generating a weak acid (e.g., non-fluorinated sulfonic acid or carboxylic acid), if the strong acid generated from the photoacid generator upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If the photoacid generator capable of generating a strong acid is also an onium salt, an exchange from the strong acid (generated upon exposure to high-energy radiation) to a weak acid as above can take place, but it never happens that the weak acid (generated upon exposure to high-energy radiation) collides with the unreacted onium salt capable of generating a strong acid to induce a salt exchange. This is because of a likelihood of an onium cation forming an ion pair with a stronger acid anion.

In the resist composition of the invention, there may be added a compound which is decomposed with an acid to generate another acid, that is, acid amplifier compound. For these compounds, reference should be made to J. Photopolym. Sci. and Tech., 8, 43-44, 45-46 (1995), and ibid., 9, 29-30 (1996).

Examples of the acid amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior.

In the resist composition of the invention, an appropriate amount of the acid amplifier compound is up to 2 parts, and especially up to 1 part by weight per 100 parts by weight of the base resin. Excessive amounts of the acid amplifier compound make diffusion control difficult, leading to degradation of resolution and pattern profile.

Quencher

A quencher (D) may be optionally used in the resist composition of the invention. The term "quencher" as used herein has a meaning generally known in the art and refers to a compound capable of suppressing the rate of diffusion when the acid generated by the acid generator diffuses within the resist film. The inclusion of quencher facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile.

Examples of suitable quenchers include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, carbamate derivatives, and ammonium salts.

Also included are amine compounds of the following general formula (D)-1.

$$N(X)_n(Y)_{3-n} \quad (D)\text{-}1$$

$$-[R^{300}-O-R^{301}] \quad (X)\text{-}1$$

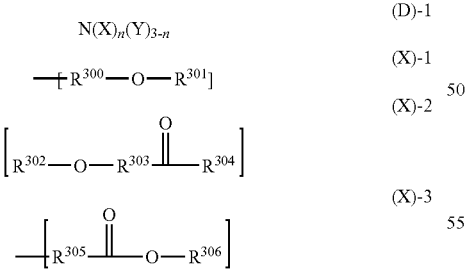

$$-[R^{305}\overset{O}{\underset{\|}{C}}-O-R^{306}] \quad (X)\text{-}3$$

In formula (D)-1, n is equal to 1, 2 or 3. The side chain X is independently selected from groups of the general formulas (X)-1 to (X)-3. The side chain Y is independently hydrogen or a straight, branched or cyclic $C_1$-$C_{20}$ alkyl group in which some or all hydrogen atoms may be substituted by fluorine atoms and which may contain an ether or hydroxyl group. Two or three X may bond together to form a ring.

In the formulas, $R^{300}$, $R^{302}$ and $R^{305}$ are independently straight or branched $C_1$-$C_4$ alkylene groups; $R^{301}$ and $R^{304}$ are independently hydrogen or straight, branched or cyclic $C_1$-$C_{50}$ alkyl groups in which some or all hydrogen atoms may be substituted by fluorine atoms and which may contain one or more hydroxyl, ether, ester groups or lactone rings; $R^{303}$ is a single bond or a straight or branched $C_1$-$C_4$ alkylene group; $R^{306}$ is a straight, branched or cyclic $C_1$-$C_{50}$ alkyl group in which some or all hydrogen atoms may be substituted by fluorine atoms and which may contain one or more hydroxyl, ether, ester groups or lactone rings.

Also useful are cyclic structure-bearing amine compounds having the following general formula (D)-2.

Herein X is as defined above, and $R^{307}$ is a straight or branched $C_2$-$C_{20}$ alkylene group in which some or all hydrogen atoms may be substituted by fluorine atoms and which may contain one or more carbonyl, ether, ester or sulfide groups.

Also included are cyano-bearing amine compounds having the following general formulae (D)-3 to (D)-6.

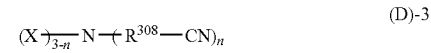

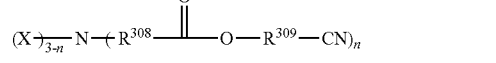

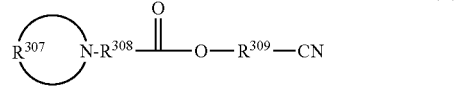

Herein X, $R^{307}$ and n are as defined in formula (B)-1, and $R^{308}$ and $R^{309}$ are each independently a straight or branched $C_1$-$C_4$ alkylene group.

Also included are amine compounds of imidazole structure having a polar functional group, represented by the general formula (D)-7.

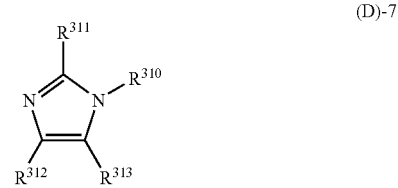

Herein $R^{310}$ is a straight, branched or cyclic $C_2$-$C_{50}$ alkyl group in which some or all hydrogen atoms may be substituted by fluorine atoms and which has one or more polar functional groups selected from among ester, acetal, cyano, hydroxyl, carbonyl, ether, sulfide, and carbonate groups and mixtures thereof. $R^{311}$, $R^{312}$ and $R^{313}$ are each independently hydrogen, a straight, branched or cyclic $C_1$-$C_{10}$ alkyl group, aryl group or aralkyl group.

Further included are amine compounds of benzimidazole structure having polar functional group, represented by the general formula (D)-8.

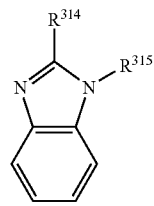
(D)-8

Herein $R^{314}$ is hydrogen, a straight, branched or cyclic $C_1$-$C_{50}$ alkyl group, aryl group or aralkyl group. $R^{315}$ is a straight, branched or cyclic $C_1$-$C_{50}$ alkyl group in which some or all hydrogen atoms may be substituted by fluorine atoms and which may have one or more polar functional groups selected from ester, acetal, cyano, hydroxyl, carbonyl, ether, sulfide, and carbonate groups and mixtures thereof.

Further included are heterocyclic nitrogen-containing compounds having a polar functional group, represented by the general formulae (D)-9 and (D)-10.

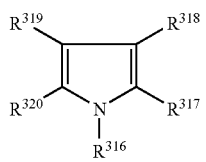
(D)-9

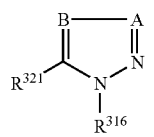
(D)-10

Herein A is a nitrogen atom or =C—$R^{322}$. B is a nitrogen atom or =C—$R^{323}$. $R^{316}$ is a straight, branched or cyclic $C_2$-$C_{50}$ alkyl group in which some or all hydrogen atoms may be substituted by fluorine atoms and which has one or more polar functional groups selected from among ester, acetal, cyano, hydroxyl, carbonyl, ether, sulfide, and carbonate groups and mixtures thereof. $R^{317}$, $R^{318}$, $R^{319}$ and $R^{320}$ are each independently hydrogen, a straight, branched or cyclic $C_1$-$C_{10}$ alkyl group or aryl group, or a pair of $R^{317}$ and $R^{318}$ and a pair of $R^{319}$ and $R^{321}$ taken together, may form a benzene, naphthalene or pyridine ring with the carbon atoms to which they are attached. $R^{321}$ is hydrogen, a straight, branched or cyclic $C_1$-$C_{10}$ alkyl group or aryl group. $R^{322}$ and $R^{323}$ each are hydrogen, a straight, branched or cyclic $C_1$-$C_{10}$ alkyl group or aryl group, or a pair of $R^{321}$ and $R^{323}$, taken together, may form a benzene or naphthalene ring with the carbon atoms to which they are attached.

Also included are amine compounds having an aromatic carboxylic acid ester structure, represented by the general formulae (D)-11 to (D)-14.

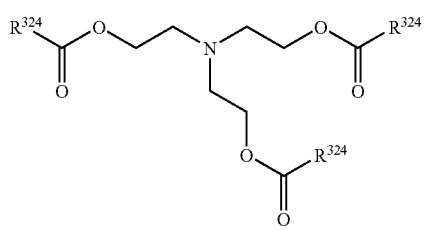
(D)-11

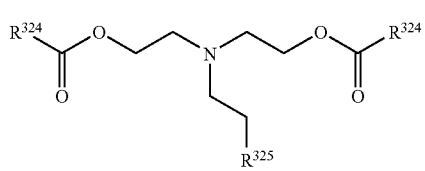
(D)-12

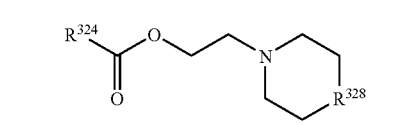
(D)-13

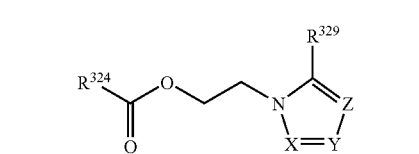
(D)-14

Herein $R^{324}$ is a $C_6$-$C_{20}$ aryl group or $C_4$-$C_{20}$ hetero-aromatic group, in which some or all hydrogen atoms may be replaced by halogen atoms, straight, branched or cyclic $C_1$-$C_{20}$ alkyl groups, $C_6$-$C_{20}$ aryl groups, $C_7$-$C_{20}$ aralkyl groups, $C_1$-$C_{10}$ alkoxy groups, $C_1$-$C_{10}$ acyloxy groups or $C_1$-$C_{10}$ alkylthio groups. $R^{325}$ is $CO_2R^{326}$, $OR^{327}$ or cyano group. $R^{326}$ is a $C_1$-$C_{10}$ alkyl group, in which some methylene groups may be replaced by oxygen atoms. $R^{327}$ is a $C_1$-$C_{10}$ alkyl or acyl group, in which some methylene groups may be replaced by oxygen atoms. $R^{328}$ is a single bond, methylene, ethylene, sulfur atom or —O(CH$_2$CH$_2$O)$_n$— group wherein n is 0, 1, 2, 3 or 4. $R^{329}$ is hydrogen, methyl, ethyl or phenyl. X is a nitrogen atom or $CR^{330}$. Y is a nitrogen atom or $CR^{331}$. Z is a nitrogen atom or $CR^{332}$. $R^{330}$, $R^{331}$ and $R^{332}$ are each independently hydrogen, methyl or phenyl. Alternatively, a pair of $R^{330}$ and $R^{331}$ or a pair of $R^{331}$ and $R^{332}$ may bond together to form a $C_6$-$C_{20}$ aromatic ring or $C_2$-$C_{20}$ hetero-aromatic ring with the carbon atoms to which they are attached.

Further included are amine compounds of 7-oxanorbornane-2-carboxylic ester structure, represented by the general formula (D)-15.

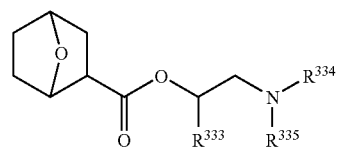
(D)-15

Herein $R^{333}$ is hydrogen or a straight, branched or cyclic $C_1$-$C_{10}$ alkyl group. $R^{334}$ and $R^{335}$ are each independently a $C_1$-$C_{20}$ alkyl group, $C_6$-$C_{20}$ aryl group or $C_7$-$C_{20}$ aralkyl group, which may contain one or more polar functional groups selected from among ether, carbonyl, ester, alcohol, sulfide, nitrile, amine, imine, and amide and in which some hydrogen atoms may be replaced by halogen atoms. $R^{334}$ and $R^{335}$, taken together, may form a heterocyclic or hetero-aromatic ring of 2 to 20 carbon atoms with the nitrogen atom to which they are attached.

Illustrative examples of the quencher used herein are given below, but not limited thereto.

Examples of suitable primary aliphatic amines include methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, N,N-bis(hydroxyethyl)aniline, 2-methylaniline, 3-methylaniline, 4-methylaniline, ethylaniline, propylaniline, dimethylaniline, 2,6-diisopropylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazane derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable nitrogen-containing compounds with carboxyl group include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). A typical nitrogen-containing compound with sulfonyl group is 3-pyridinesulfonic acid. Examples of suitable nitrogen-containing compounds with hydroxyl group, nitrogen-containing compounds with hydroxyphenyl group, and alcoholic nitrogen-containing compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, benzamide, and 1-cyclohexylpyrrolidone. Suitable imide derivatives include phthalimide, succinimide, and maleimide. Suitable carbamate derivatives include N-tert-butoxycarbonyl-N,N-dicyclohexylamine, N-tert-butoxycarbonylbenzimidazole, and oxazolidinone.

Suitable ammonium salts include pyridinium p-toluenesulfonate, triethylammonium p-toluenesulfonate, trioctylammonium p-toluenesulfonate, triethylammonium 2,4,6-triisopropylbenzenesulfonate, trioctylammonium 2,4,6-triisopropylbenzenesulfonate, triethylammonium camphorsulfonate, trioctylammonium camphorsulfonate, tetramethylammonium hydroxide, tetraethylammonium hydroxide, tetrabutylammonium hydroxide, benzyltrimethylammonium hydroxide, tetramethylammonium p-toluenesulfonate, tetrabutylammonium p-toluenesulfonate, benzyltrimethylammonium p-toluenesulfonate, tetramethylammonium camphorsulfonate, tetrabutylammonium camphorsulfonate, benzyltrimethylammonium camphorsulfonate, tetramethylammonium 2,4,6-triisopropylbenzenesulfonate, tetrabutylammonium 2,4,6-triisopropylbenzenesulfonate, benzyltrimethylammonium 2,4,6-triisopropylbenzenesulfonate, tetramethylammonium acetate, tetrabutylammonium acetate, benzyltrimethylammonium acetate, tetramethylammonium benzoate, tetrabutylammonium benzoate, and benzyltrimethylammonium benzoate.

Further examples of the tertiary amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris (2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, tris(2-benzoyloxyethyl)amine, tris[2-(4-methoxybenzoyloxy)ethyl]amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, 5 N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]-ethylamine, N,N-bis(2-acetoxyethyl)-2-[(methoxycarbonyl)methoxycarbonyl]-ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)-ethylamine, N,N-bis(2-acetoxyethyl)-2-(tetrahydrofurfuryloxycarbonyl)-ethylamine, N,N-bis(2-hydroxyethyl)-2-[(2-oxotetrahydrofuran-3-yl)oxycarbonyl]ethylamine, N,N-bis(2-acetoxyethyl)-2-[(2-oxotetrahydrofuran-3-yl)oxycarbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)-ethylamine, N,N-bis(2-formyloxyethyl)-2-(2-formyloxyethoxycarbonyl)-ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl]amine, N-(2-methoxyethyl)-bis[2-(methoxycarbonyl)ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxycarbonyloxy)ethyl]amine, tris(methoxycarbonylmethyl)amine, tris(ethoxycarbonylmethyl)amine, N-butyl-bis(methoxycarbonylmethyl)amine, N-hexyl-bis(methoxycarbonylmethyl)amine, and β-(diethylamino)-δ-valerolactone.

Illustrative examples of the amine compounds include 1-[2-(methoxymethoxy)ethyl]pyrrolidine, 1-[2-(methoxymethoxy)ethyl]piperidine, 4-[2-(methoxymethoxy)ethyl]morpholine, 1-[2-(methoxymethoxy)ethyl]imidazole, 1-[2-(methoxymethoxy)ethyl]benzimidazole, 1-[2-(methoxymethoxy)ethyl]-2-phenylbenzimidazole, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 1-[2-[(2-methoxyethoxy)methoxy]ethyl]imidazole, 1-[2-[(2-methoxyethoxy)methoxy]ethyl]benzimidazole, 1-[2-[(2-methoxyethoxy)methoxy]ethyl]-2-phenylbenzimidazole, 1-[2-[2-(2-methoxyethoxy)ethoxy]ethyl]pyrrolidine, 1-[2-[2-(2-methoxyethoxy)ethoxy]ethyl]piperidine, 4-[2-[2-(2-methoxyethoxy)ethoxy]ethyl]morpholine, 1-[2-[2-(2-methoxyethoxy)ethoxy]ethyl]imidazole, 1-[2-[2-(2-methoxyethoxy)ethoxy]ethyl]benzimidazole, 1-[2-[2-(2-methoxyethoxy)ethoxy]ethyl]-2-phenylbenzimidazole, 1-[2-[2-(2-butoxyethoxy)ethoxy]ethyl]pyrrolidine, 1-[2-[2-(2-butoxyethoxy)ethoxy]ethyl]piperidine, 4-[2-[2-(2-butoxyethoxy)ethoxy]ethyl]morpholine, 1-[2-[2-(2-butoxyethoxy)ethoxy]ethyl]imidazole, 1-[2-[2-(2-butoxyethoxy)ethoxy]ethyl]benzimidazole, 1-[2-[2-(2-butoxyethoxy)ethoxy]ethyl]-2-phenylbenzimidazole, 1-[2-[2-[2-(2-methoxyethoxy)ethoxy]ethoxy]ethyl]pyrrolidine, 1-[2-[2-[2-(2-methoxyethoxy)ethoxy]ethoxy]ethyl]piperidine, 4-[2-[2-[2-(2-methoxyethoxy)ethoxy]ethoxy]ethyl]morpholine, 1-[2-[2-[2-(2-methoxyethoxy)ethoxy]ethoxy]ethyl]imidazole, 1-[2-[2-[2-(2-methoxyethoxy)ethoxy]ethoxy]ethyl]benzimidazole, 1-[2-[2-[2-(2-methoxyethoxy)ethoxy]ethoxy]ethyl]-2-phenylbenzimidazole, 4-[2-{2-[2-(2-butoxyethoxy)ethoxy]ethoxy}ethyl]morpholine, 2-(1-pyrrolidinyl)ethyl acetate, 2-piperidinoethyl acetate, 2-morpholinoethyl acetate, 2-(1-imidazolyl)ethyl acetate, 2-(1-benzimidazolyl)ethyl acetate, 2-(2-phenyl-1-benzimidazolyl)ethyl acetate, 2-methoxyethyl morpholinoacetate, 2-(1-pyrrolidinyl)ethyl 2-methoxyacetate, 2-piperidinoethyl 2-methoxyacetate, 2-morpholinoethyl 2-methoxyacetate, 2-(1-imidazolyl)ethyl 2-methoxyacetate, 2-(1-benzimidazolyl)ethyl 2-methoxyacetate, 2-(2-phenyl-1-benzimidazolyl)ethyl 2-methoxyacetate, 2-(1-pyrrolidinyl)ethyl 2-(2-methoxyethoxy)acetate, 2-piperidinoethyl 2-(2-methoxyethoxy)acetate, 2-morpholinoethyl 2-(2-methoxyethoxy)acetate, 2-(1-imidazolyl)ethyl 2-(2-methoxyethoxy)acetate, 2-(1-benzimidazolyl)ethyl 2-(2-methoxyethoxy)acetate, 2-(2-phenyl-1-benzimidazolyl) ethyl 2-(2-methoxyethoxy)acetate, 2-(1-pyrrolidinyl)ethyl 2-[2-(2-methoxyethoxy)ethoxy]acetate, 2-piperidinoethyl 2-[2-(2-methoxyethoxy)ethoxy]acetate, 2-morpholinoethyl 2-[2-(2-methoxyethoxy)ethoxy]acetate, 2-(1-imidazolyl) ethyl 2-[2-(2-methoxyethoxy)ethoxy]acetate, 2-(1-benzimidazolyl)ethyl 2-[2-(2-methoxyethoxy)ethoxy]acetate, 2-(2-phenyl-1-benzimidazolyl)ethyl 2-[2-(2-methoxyethoxy)ethoxy]acetate, 2-morpholinoethyl butyrate, 2-morpholinoethyl hexanoate, 2-morpholinoethyl octanoate, 2-morpholinoethyl decanoate, 2-morpholinoethyl laurate, 2-morpholinoethyl myristate, 2-morpholinoethyl palmitate, 2-morpholinoethyl stearate, 2-morpholinoethyl behenate, 2-morpholinoethyl cholate, 2-morpholinoethyl tris(O-acetyl) cholate, 2-morpholinoethyl tris(O-formyl)cholate, 2-morpholinoethyl dehydrocholate, 2-morpholinoethyl cyclopentanecarboxylate, 2-morpholinoethyl cyclohexanecarboxylate, 2-(1-pyrrolidinyl)ethyl 7-oxanorbornane-2-carboxylate, 2-piperidinoethyl 7-oxanorbornane-2-carboxylate, 2-morpholinoethyl 7-oxanorbornane-2-carboxylate, 2-(1-imidazolyl)ethyl 7-oxanorbornane-2-carboxylate, 2-(1-benzimidazolyl)ethyl 7-oxanorbornane-2-carboxylate, 2-(2-phenyl-1-benzimidazolyl)ethyl 7-oxanorbornane-2-carboxylate, 2-morpholinoethyl adamantanecarboxylate, 2-(1-pyrrolidinyl)ethyl formate, 2-piperidinoethyl propionate, 2-morpholinoethyl acetoxyacetate, 2-(1-pyrrolidinyl)ethyl methoxyacetate, 2-(1-pyrrolidinyl) ethyl benzoate, 2-piperidinoethyl benzoate, 2-morpholinoethyl benzoate, 2-(1-imidazolyl)ethyl benzoate, 2-(1-benzimidazolyl)ethyl benzoate, 2-(2-phenyl-1-benzimidazolyl)ethyl benzoate, 2-(1-pyrrolidinyl)ethyl 4-methoxybenzoate, 2-piperidinoethyl 4-methoxybenzoate, 2-morpholinoethyl 4-methoxybenzoate, 2-(1-imidazolyl)ethyl 4-methoxybenzoate, 2-(1-benzimidazolyl)ethyl 4-methoxybenzoate, 2-(2- phenyl-1-benzimidazolyl)ethyl 4-methoxybenzoate, 2-(1-pyrrolidinyl)ethyl 4-phenylbenzoate, 2-piperidinoethyl 4-phenylbenzoate, 2-morpholinoethyl 4-phenylbenzoate, 2-(1-imidazolyl)ethyl 4-phenylbenzoate, 2-(1-benzimidazolyl)ethyl 4-phenylbenzoate, 2-(2-phenyl-1-benzimidazolyl)ethyl 4-phenylbenzoate, 2-(1-pyrrolidinyl)ethyl 1-naphthalenecarboxylate, 2-piperidinoethyl 1-naphthalenecarboxylate, 2-morpholinoethyl 1-naphthalenecarboxylate, 2-(1-imidazolyl)ethyl 1-naphthalenecarboxylate, 2-(1-benzimidazolyl)ethyl 1-naphthalenecarboxylate, 2-(2-phenyl-1-benzimidazolyl)ethyl 1-naphthalenecarboxylate, 2-(1-pyrrolidinyl)ethyl 2-naphthalenecarboxylate, 2-piperidinoethyl 2-naphthalenecarboxylate, 2-morpholinoethyl 2-naphthalenecarboxylate, 2-(1-imidazolyl)ethyl 2-naphthalenecarboxylate, 2-(1-benzimidazolyl)ethyl 2-naphthalenecarboxylate, 2-(2-phenyl-1-benzimidazolyl)ethyl 2-naphthalenecarboxylate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino)propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl)propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, etc.

Further illustrative examples of amine compounds include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiononitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiononitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy)ethyl]aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl]aminoacetonitrile, N-cyanomethyl-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl)aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-aminopropionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

The quenchers may be used alone or in admixture of two or more. The quencher is preferably formulated in an amount of 0.001 to 5 parts, and especially 0.01 to 3 parts by weight, per 100 parts by weight of the total base resin. Less than 0.001 phr of the quencher may achieve no addition effect whereas more than 5 phr may lead to too low a sensitivity.

Surfactant

Optionally, the resist composition of the invention may further comprise (E) a surfactant which is commonly used for facilitating the coating operation. The surfactant may be added in conventional amounts so long as this does not compromise the objects of the invention.

Illustrative, non-limiting examples of the surfactant include nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene polyoxypropylene block copolymers, sorbitan fatty acid esters such as sorbitan monolaurate, sorbitan monopalmitate, and sorbitan monostearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants such as EFTOP EF301, EF303 and EF352 (JEMCO Inc.), Megaface F171, F172, F173, $R^{08}$, $R^{30}$, $R^{90}$ and R94 (DIC Corp.), Fluorad FC-430, FC-431, FC-4430 and FC-4432 (Sumitomo 3M Co., Ltd.), Asahiguard AG710, Surflon S-381, S-382, S-386, SC101, SC102, SC103, SC104, SC105, SC106, KH-10, KH-20, KH-30 and KH-40 (Asahi Glass Co., Ltd.), and Surfynol E1004 (Nisshin Chemical Industry Co., Ltd.); organosiloxane polymers KP341, X-70-092 and X-70-093 (Shin-Etsu Chemical Co., Ltd.), acrylic acid or methacrylic acid Polyflow No. 75 and No. 95 (Kyoeisha Ushi Kagaku Kogyo Co., Ltd.). Additional useful surfactants include partially fluorinated oxetane ring-opened polymers having the structural formula (surf-1).

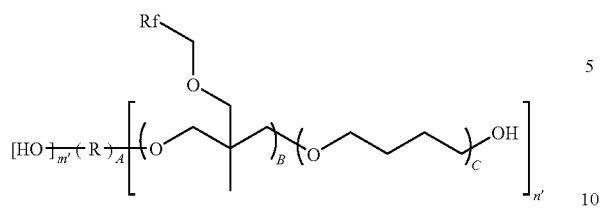

(surf-1)

It is provided herein that R, Rf, A, B, C, m', and n' are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

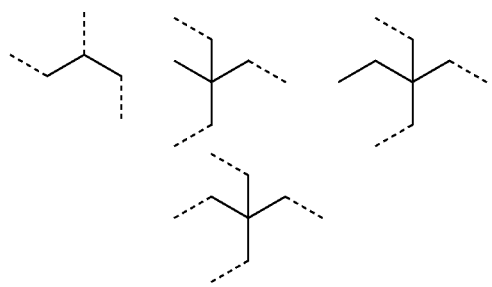

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m' is an integer of 0 to 3, n' is an integer of 1 to 4, and the sum of m' and n', which represents the valence of R, is an integer of 2 to 4. A is equal to 1, B is an integer of 2 to 25, and C is an integer of 0 to 10. Preferably, B is an integer of 4 to 20, and C is 0 or 1. Note that the above structural formula does not prescribe the arrangement of respective constituent units while they may be arranged either in blocks or randomly. For the preparation of surfactants in the form of partially fluorinated oxetane ring-opened polymers, reference should be made to U.S. Pat. No. 5,650,483, for example.

Of the foregoing surfactants, FC-4430, Surflon S-381, Surfynol E1004, KH-20, KH-30, and oxetane ring-opened polymers of formula (surf-1) are preferred. These surfactants may be used alone or in admixture.

In the resist composition, the surfactant is preferably compounded in an amount of up to 2 parts, and especially up to 1 part by weight, per 100 parts by weight of the base resin. The amount of the surfactant, if added, is preferably at least 0.01 phr.

In one embodiment wherein the immersion lithography using water is applied to the resist composition of the invention, particularly in the absence of a resist protective film, the resist composition may have added thereto another surfactant having a propensity to segregate at the resist surface after spin coating for achieving a function of minimizing water penetration or leaching. The preferred other surfactant is a polymeric surfactant which is insoluble in water, but soluble in alkaline developer, and especially which is water repellent and enhances water slippage. Suitable polymeric surfactants are shown below.

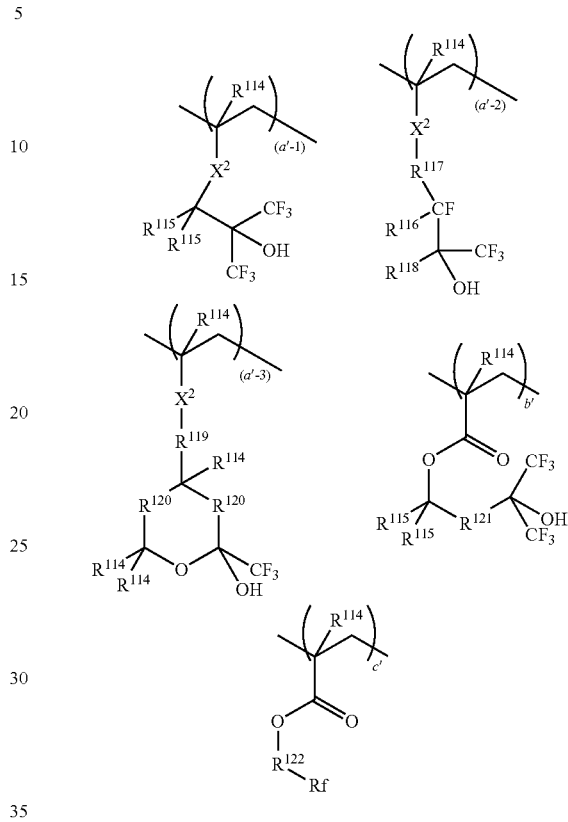

Herein $R^{114}$ is each independently hydrogen, fluorine, methyl or trifluoromethyl. $R^{115}$ is each independently hydrogen or a straight, branched or cyclic $C_1$-$C_{20}$ alkyl or fluoroalkyl group, or two $R^{115}$ in a common monomer may bond together to form a ring with the carbon atom to which they are attached, and in this event, they together represent a straight, branched or cyclic $C_2$-$C_{20}$ alkylene or fluoroalkylene group. $R^{116}$ is fluorine or hydrogen, or $R^{116}$ may bond with $R^{117}$ to form a non-aromatic ring of 3 to 10 carbon atoms in total with the carbon atom to which they are attached. $R^{117}$ is a straight, branched or cyclic $C_1$-$C_6$ alkylene group in which at least one hydrogen atom may be substituted by a fluorine atom. $R^{118}$ is a straight or branched $C_1$-$C_{10}$ alkyl group in which at least one hydrogen atom is substituted by a fluorine atom. Alternatively, $R^{117}$ and $R^{118}$ may bond together to form a non-aromatic ring with the carbon atoms to which they are attached. In this event, $R^{117}$, $R^{118}$ and the carbon atoms to which they are attached together represent a trivalent organic group of 2 to 12 carbon atoms in total. $R^{119}$ is a single bond or a $C_1$-$C_4$ alkylene. $R^{120}$ is each independently a single bond, —O—, or —$CR^{114}R^{114}$—. $R^{121}$ is a straight or branched $C_1$-$C_4$ alkylene group, or may bond with $R^{115}$ within a common monomer to form a $C_3$-$C_6$ non-aromatic ring with the carbon atom to which they are attached. $R^{122}$ is 1,2-ethylene, 1,3-propylene, or 1,4-butylene. Rf is a linear perfluoroalkyl group of 3 to 6 carbon atoms, typically 3H-perfluoropropyl, 4H-perfluorobutyl, 5H-perfluoropentyl, or 6H-perfluorohexyl. $X^2$ is each independently —C(=O)—O—, —O—, or —C(=O)—$R^{123}$—C(=O)—O—. $R^{123}$ is a straight, branched or cyclic $C_1$-$C_{10}$ alkylene group. The subscripts are in the range: $0 \leqq (a'\text{-}1) < 1$, $0 \leqq (a'\text{-}2) < 1$, $0 \leqq (a'\text{-}3) < 1$, $0 < (a'\text{-}1)+(a'\text{-}2)+(a'\text{-}3) < 1$, $0 \leqq b' < 1$, $0 \leqq c' < 1$, and $0 < (a'\text{-}1)+(a'\text{-}2)+(a'\text{-}3)+b'+c' \leqq 1$.

In the chemically amplified resist composition of the invention, the polymeric surfactant is preferably formulated in an amount of 0.001 to 20 parts, and more preferably 0.01 to 10 parts by weight, per 100 parts by weight of the base resin. Reference should also be made to JP-A 2007-297590.

A further embodiment is a chemically amplified negative working resist composition comprising the inventive polymer. When used in this embodiment, the inventive polymer should contain recurring units having a substituent group capable of forming a crosslinked structure with an acid crosslinker, in addition to recurring units of formula (2). Examples of additional recurring units include, but are not limited to, those units derived from acrylic acid, methacrylic acid, hydroxystyrene (which may be substituted at any positions), and hydroxyvinylnaphthalene (which may be substituted at any positions).

Besides the inventive polymer, any alkali-soluble resins may be added. Examples of the alkali-soluble resin include poly(p-hydroxystyrene), poly(m-hydroxystyrene), poly(4-hydroxy-2-methylstyrene), poly(4-hydroxy-3-methylstyrene), poly(α-methyl-p-hydroxystyrene), partially hydrogenated p-hydroxystyrene copolymers, p-hydroxystyrene-α-methyl-p-hydroxystyrene copolymers, p-hydroxystyrene-α-methylstyrene copolymers, p-hydroxystyrene-styrene copolymers, p-hydroxystyrene-m-hydroxystyrene copolymers, p-hydroxystyrene-styrene copolymers, p-hydroxystyrene-acrylic acid copolymers, p-hydroxystyrene-methacrylic acid copolymers, p-hydroxystyrene-methyl methacrylate copolymers, p-hydroxystyrene-acrylic acid-methyl methacrylate copolymers, p-hydroxystyrene-methyl acrylate copolymers, p-hydroxystyrene-methacrylic acid-methyl methacrylate copolymers, poly(methacrylic acid), poly(acrylic acid), acrylic acid-methyl acrylate copolymers, methacrylic acid-methyl methacrylate copolymers, acrylic acid-maleimide copolymers, methacrylic acid-maleimide copolymers, p-hydroxystyrene-acrylic acid-maleimide copolymers, and p-hydroxystyrene-methacrylic acid-maleimide copolymers, but are not limited to these combinations.

The inventive polymer and the other alkali-soluble resin are preferably blended in a weight ratio from 100:0 to 10:90, more preferably from 100:0 to 20:80. If the blend ratio of the inventive polymer is below this range, the resist composition would become poor in some of the desired properties. The properties of the resist composition can be adjusted by properly changing the blend ratio of the inventive polymer.

Notably, the alkali-soluble resin is not limited to one type and a mixture of two or more resins may be added. The use of plural resins allows for easy adjustment of resist properties.

Crosslinker

Formulated in the negative resist composition is an acid crosslinker (F) which forms a crosslinked structure under the action of acid. Typical crosslinkers are compounds having at least two hydroxymethyl, alkoxymethyl, epoxy or vinyl ether groups within a molecule. Substituted glycoluril derivatives, urea derivatives, and hexa(methoxymethyl)melamine compounds are suitable as the acid crosslinker. Examples include N,N,N',N'-tetramethoxymethylurea, hexamethoxymethylmelamine, tetraalkoxymethyl-substituted glycoluril compounds such as tetrahydroxymethyl-substituted glycoluril and tetramethoxymethylglycoluril, and condensates of phenolic compounds such as substituted or unsubstituted bis(hydroxymethylphenol) compounds and bisphenol A with epichlorohydrin. Especially preferred crosslinkers are 1,3,5,7-tetraalkoxymethylglycolurils such as 1,3,5,7-tetramethoxymethylglycoluril, 1,3,5,7-tetrahydroxymethylglycoluril, 2,6-dihydroxymethyl-p-cresol, 2,6-dihydroxymethylphenol, 2,2',6,6'-tetrahydroxymethyl-bisphenol A, 1,4-bis[2-(2-hydroxypropyl)]benzene, N,N,N',N'-tetramethoxymethylurea, and hexamethoxymethylmelamine.

In the chemically amplified resist composition, an appropriate amount of the acid crosslinker (F) is, though not limited thereto, 1 to 20 parts, and especially 5 to 15 parts by weight per 100 parts by weight of the base resin. The crosslinkers may be used alone or in admixture of two or more.

While the resist composition of the invention typically comprises a polymer or base resin, acid generator, organic solvent and quencher as described above, there may be added optional other ingredients such as surfactants and crosslinkers, as well as dissolution inhibitors, acidic compounds, stabilizers, and dyes. Optional ingredients may be added in conventional amounts so long as this does not compromise the objects of the invention.

In forming a pattern from the resist composition of the invention, any well-known lithography may be employed. For example, the composition is applied onto a substrate for integrated circuitry fabrication (e.g., Si, $SiO_2$, SiN, SiON, TiN, WSi, BPSG, SOG, organic antireflective coating, etc.) or a substrate for mask circuitry fabrication (e.g., Cr, CrO, CrON, MoSi, etc.) by a suitable coating technique such as spin coating. The coating is prebaked on a hot plate at a temperature of 60 to 150° C. for about 1 to 10 minutes, preferably 80 to 140° C. for 1 to 5 minutes, to form a resist film of 0.05 to 2.0 µm thick. A patterning mask having the desired pattern is then placed over the resist film, and the film exposed through the mask to an electron beam or to high-energy radiation such as deep-UV, excimer laser or x-ray in a dose of about 1 to 200 $mJ/cm^2$, and preferably about 10 to 100 $mJ/cm^2$. Alternatively, pattern formation may be performed by writing with an electron beam directly (not through a mask). Light exposure may be done by a conventional exposure process or in some cases, by an immersion process of providing liquid impregnation between the mask and the resist. In the case of immersion lithography, a protective coating which is insoluble in water may be used. The resist film is then post-exposure baked (PEB) on a hot plate at 60 to 150° C. for 1 to 5 minutes, and preferably at 80 to 140° C. for 1 to 3 minutes. Finally, development is carried out using as the developer an aqueous alkali solution, such as a 0.1 to 5 wt %, preferably 2 to 3 wt %, aqueous solution of tetramethylammonium hydroxide (TMAH), this being done by a conventional method such as dip, puddle, or spray development for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with, in particular, deep-UV having a wavelength of 250 to 190 nm, excimer laser, x-ray, or electron beam. The desired pattern may not be obtainable outside the upper and lower limits of the above range.

The water-insoluble protective coating which is used in the immersion lithography is to prevent the resist coating from being leached and to improve water slippage at the coating surface and is generally divided into two types. The first type is an organic solvent-strippable protective coating which must be stripped, prior to alkaline development, with an organic solvent in which the resist coating is not dissolvable. The second type is an alkali-soluble protective coating which is soluble in an alkaline developer so that it can be removed simultaneously with the removal of solubilized areas of the resist coating. The protective coating of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective coating of the second type is formed.

Any desired step may be added to the pattern forming process. For example, after a photoresist coating is formed, a step of rinsing with pure water (post-soaking) may be introduced to extract the acid generator or the like from the coating surface or wash away particles. After exposure, a step of rinsing (post-soaking) may be introduced to remove any water remaining on the coating after exposure.

EXAMPLE

Examples and Comparative Examples are given below by way of illustration and not by way of limitation.

Sulfonium salts having a polymerizable anion within the scope of the invention were synthesized according to the following formulation.

Synthesis Example 1-1

Synthesis of Triphenylsulfonium Chloride

Diphenyl sulfoxide, 40 g (0.2 mole), was dissolved in 400 g of dichloromethane, which was stirred under ice cooling. At a temperature below 20° C., 65 g (0.6 mole) of trimethylsilyl chloride was added dropwise to the solution, which was allowed to mature for 30 minutes at the temperature. Then, a Grignard reagent which had been prepared from 14.6 g (0.6 mole) of metallic magnesium, 67.5 g (0.6 mole) of chlorobenzene and 168 g of tetrahydrofuran (THF) was added dropwise at a temperature below 20° C. The reaction solution was allowed to mature for one hour, after which 50 g of water at a temperature below 20° C. was added to quench the reaction. To this solution, 150 g of water, 10 g of 12N hydrochloric acid, and 200 g of diethyl ether were further added. The water layer was separated and washed with 100 g of diethyl ether, yielding an aqueous solution of triphenylsulfonium chloride. The compound in aqueous solution form was used in the subsequent reaction without further isolation.

Synthesis Example 1-2

Synthesis of 4-tert-butylphenyldiphenylsulfonium bromide

The target compound was obtained by following the procedure of Synthesis Example 1-1 aside from using 4-tert-butylbromobenzene instead of the chlorobenzene in Synthesis Example 1 and increasing the amount of water for extraction.

Synthesis Example 1-3

Synthesis of 4-tert-butoxyphenyldiphenylsulfonium chloride

The target compound was obtained by following the procedure of Synthesis Example 1-1 aside from using 4-tert-butoxychlorobenzene instead of the chlorobenzene in Synthesis Example 1-1, using dichloromethane containing 5 wt % of triethylamine as the solvent, and increasing the amount of water for extraction.

Synthesis Example 1-4

Synthesis of tris(4-methylphenyl)sulfonium chloride

The target compound was obtained by following the procedure of Synthesis Example 1-1 aside from using bis(4-methylphenyl) sulfoxide instead of the diphenyl sulfoxide and 4-chlorotoluene instead of the chlorobenzene in Synthesis Example 1-1, and increasing the amount of water for extraction.

Synthesis Example 1-5

Synthesis of tris(4-tert-butylphenyl)sulfonium bromide

The target compound was obtained by following the procedure of Synthesis Example 1-1 aside from using bis(4-tert-butylphenyl) sulfoxide instead of the diphenyl sulfoxide and 4-tert-butylbromobenzene instead of the chlorobenzene in Synthesis Example 1-1, and increasing the amount of water for extraction.

Synthesis Example 1-6

Synthesis of bis(4-tert-butylphenyl)iodonium hydrogen sulfate

A mixture of 84 g (0.5 mole) of tert-butylbenzene, 53 g (0.25 mole) of potassium iodate and 50 g of acetic anhydride was stirred under ice cooling. A mixture of 35 g of acetic anhydride and 95 g of conc. sulfuric acid was added dropwise thereto at a temperature below 30° C. The resulting solution was allowed to mature for 3 hours at room temperature and ice cooled again, after which 250 g of water was added dropwise to quench the reaction. The reaction solution was extracted with 400 g of dichloromethane. The organic layer was discolored by adding 6 g of sodium hydrogen sulfite. The organic layer was washed with 250 g of water three times. The washed organic layer was concentrated in vacuum, obtaining a crude target product. The product was used in the subsequent reaction without further purification.

Synthesis Example 1-7

Synthesis of Phenacyltetrahydrothiophenium Bromide 88.2 g (0.44 mole) of phenacyl bromide and 39.1 g (0.44 mole) of tetrahydrothiophene were dissolved in 220 g of nitromethane, which was stirred for 4 hours at room temperature. 800 g of water and 400 g of diethyl ether were added to the reaction solution whereupon the mixture separated into two layers. The aqueous layer was taken out, which was an aqueous solution of the target compound, phenacyltetrahydrothiophenium bromide.

Synthesis Example 1-8

Synthesis of Dimethylphenylsulfonium Hydrogen Sulfate 6.2 g (0.05 mole) of thioanisole and 6.9 g (0.055 mole) of dimethyl sulfate were stirred for 12 hours at room temperature. 100 g of water and 50 ml of diethyl ether were added to the reaction solution whereupon the mixture separated into two layers. The aqueous layer was taken out, which was an aqueous solution of the target compound, dimethylphenylsulfonium hydrogen sulfate.

Synthesis Example 1-9

Synthesis of sodium 2-benzoyloxy-1,1,3,3,3-pentafluoropropane-1-sulfonate 10.0 g of 1,1,3,3,3-pentafluoro-2-propan-2-yl benzoate, which had been synthesized by a conventional technique, was dispersed in 72 g of water, after which 12.0 g of sodium hydrogen sulfite and 1.24 g of benzoyl peroxide were added. The mixture was allowed to react at 85° C. for 65 hours. It was allowed to cool and combined with toluene, followed by separatory operation to separate a water layer. A saturated sodium chloride aqueous solution was added to the water layer whereupon white crystals settled out. The crystals were collected by filtration, washed with a small volume of saturated sodium chloride aqueous solution and then dried in vacuum, obtaining the target compound, sodium 2-benzoyloxy-1,1,3,3,3-pantafluoropropane-1-sulfonate. White crystals, 5.85 g (yield 43%).

Synthesis Example 1-10

Synthesis of triphenylsulfonium 2-benzoyloxy-1,1,3,3,3-pentafluoropropane-1-sulfonate To 50 g of dichloromethane were added an amount (corresponding to 0.011 mole) of the triphenylsulfonium chloride aqueous solution of Synthesis Example 1-1 and 3.6 g (0.01 mole) of sodium 2-benzoyloxy-1,1,3,3,3-pantafluoropropane-1-sulfonate synthesized in Synthesis Example 1-9, followed by stirring. The organic layer was separated and washed with 50 g of water three times. The organic layer was concentrated and 25 g of diethyl ether was added to the concentrate for crystallization. The crystals were filtered and dried, obtaining the target compound. White crystals, 4.5 g (yield 75%).

Synthesis Example 1-11

Synthesis of triphenylsulfonium 2-hydroxy-1,1,3,3,3-pentafluoropropane-1-sulfonate (PAG1)

In 72 g of methanol was dissolved 34.4 g of triphenylsulfonium 2-benzoyloxy-1,1,3,3,3-pentafluoropropane-1-sulfonate synthesized in Synthesis Example 1-10. While the solution was stirred under ice cooling, 54.0 g of 5% sodium hydroxide solution was added dropwise at a temperature below 10° C. It was allowed to mature at the temperature for 4 hours. At a temperature below 10° C., 6.8 g of 12N hydrochloric acid was added to quench the reaction. The methanol was distilled off in vacuum, after which 270 g of dichloromethane was added to the residue. The organic layer was washed with 40 g of water three times. The organic layer was concentrated, and 60 g of diethyl ether was added to the concentrate for crystallization. The crystals were filtered and dried, obtaining the target compound. White crystals, 24.3 g (yield 85%).

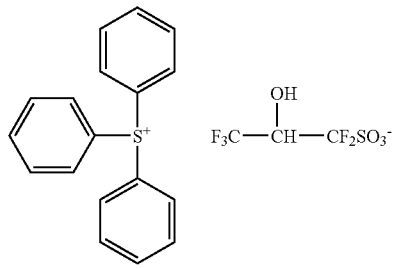

PAG 1

Synthesis Examples 1-12 to 1-18

Target compounds were synthesized as in Synthesis Examples 1-10 and 1-11 except that the onium salts prepared in Synthesis Examples 1-2 to 1-8 were used. The resulting onium salts PAG2 to PAG8 are shown below.

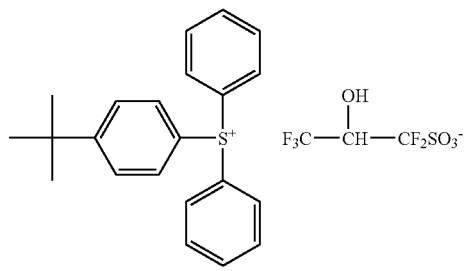

PAG 2

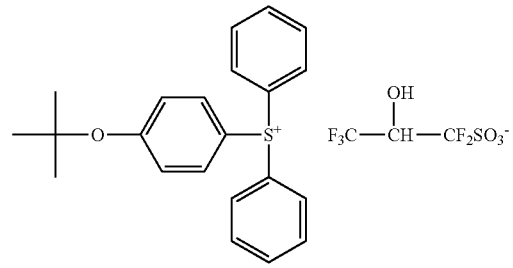

PAG 3

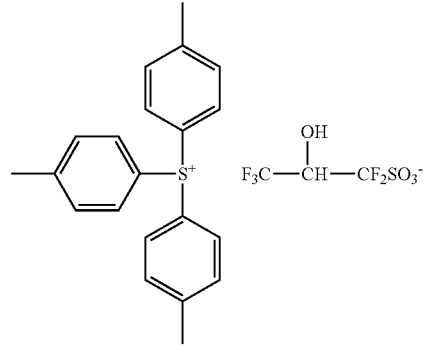

PAG 4

-continued

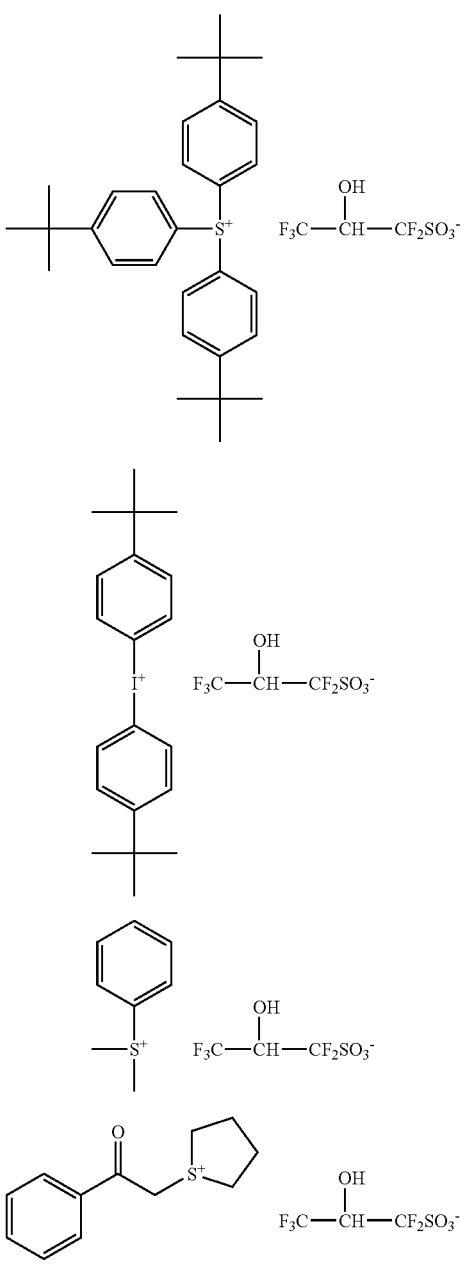

PAG 5

PAG 6

PAG 7

PAG 8

Synthesis Example 1-19

Synthesis of triphenylsulfonium 2-(2-chloroacetoxy)-1,1,3,3,3-pentafluoropropane-1-sulfonate (PAG9)

To a mixture of 148 g (0.30 mole) of triphenylsulfonium 2-hydroxy-1,1,3,3,3-pentafluoropropane-1-sulfonate synthesized in Synthesis Example 1-11, 37.3 g (0.33 mole) of chloroacetyl chloride, and 600 g of acetonitrile, 28.5 g (0.36 mole) of pyridine was added dropwise, followed by stirring at room temperature for 3 hours. The reaction solution was then concentrated and combined with 300 g of 5% dilute hydrochloric acid and 600 g of dichloromethane whereupon the organic layer was separated. The organic layer was washed with 300 g of water, from which dichloromethane was distilled off under vacuum. To the residue was added 600 g of methyl isobutyl ketone. This was washed with 300 g of water, with 300 g of dilute aqueous ammonia, and three times with 300 g of water whereupon methyl isobutyl ketone was distilled off under vacuum. The residue was purified by adding ether for recrystallization, filtered and dried. The target compound was obtained as white crystals (158 g, yield 92%).

Synthesis Example 1-20

Synthesis of triphenylsulfonium 2-(4-chlorobutyryloxy)-1,1,3,3,3-pentafluoropropane-1-sulfonate (PAG10)

To a mixture of 7.39 g (0.015 mole) of triphenylsulfonium 2-hydroxy-1,1,3,3,3-pentafluoropropane-1-sulfonate, 2.33 g (0.017 mole) of chlorobutyric chloride, and 37 g of acetonitrile, 1.42 g (0.018 mole) of pyridine was added dropwise, followed by stirring at room temperature for 3 hours. Then 18 g of 5% dilute hydrochloric acid was added to the reaction solution whereupon acetonitrile was distilled off under vacuum. The residue was combined with 40 g of dichloromethane whereupon the organic layer was separated. The organic layer was washed with 30 g of water, from which dichloromethane was distilled off under vacuum. To the residue was added 40 g of methyl isobutyl ketone. This was washed with 30 g of water, with 30 g of dilute aqueous ammonia, and three times with 30 g of water whereupon methyl isobutyl ketone was distilled off under vacuum. Ether was added to the residue, followed by decantation and vacuum drying. The target compound was obtained as brown oil (7.94 g, yield 87%).

Synthesis Example 1-21

Synthesis of phenoxathiin-S-oxide 100 g (0.5 mole) of phenoxathiin was dissolved in 1,600 g of acetic acid, after which 48.5 g (0.5 mole) of 35% hydrogen peroxide was added dropwise to the solution. The solution was further stirred for seven days at room temperature. Then, 3,000 g of water was added to the reaction solution to settle out white crystals. The crystals were collected by filtration and dried in vacuum, obtaining the target compound. White crystals, 90 g (yield 83%).

Synthesis Example 1-22

Synthesis of 10-phenylphenoxathiinum chloride

Synthesis Example 1-1 was repeated except that phenoxathiin-S-oxide of Synthesis Example 1-21 was used instead of diphenyl sulfoxide of Synthesis Example 1-1 to synthesize 10-phenylphenoxathiinum chloride. The compound in aqueous solution form was used in the subsequent reaction without further isolation, as in Synthesis Example 1-1.

Synthesis Example 2-1

Synthesis of triphenylsulfonium 1,1,3,3,3-pentafluoro-2-(2-methacryloyloxy-acetoxy)-propane-1-sulfonate (Monomer 1)

To 250 g of dimethylformamide were added 50.0 g (0.09 mole) of triphenylsulfonium 2-(2-chloroacetoxy)-1,1,3,3,3-pentafluoropropane-1-sulfonate synthesized in Synthesis Example 1-19, 11.4 g (0.11 mole) of sodium methacrylate, 2.6 g (0.02 mole) of sodium iodide, and 50 mg of 2,2'-methylenebis(6-t-butyl-p-cresol). The mixture was heated and stirred at 80° C. for 13 hours. The reaction solution was allowed to resume room temperature, after which 500 g of water and 1 kg of dichloromethane were added. The organic layer was separated and washed with water whereupon dichloromethane was distilled off under vacuum. The residue was combined with 300 g of methyl isobutyl ketone, washed with dilute aqueous ammonia and then with water, whereupon methyl isobutyl ketone was distilled off under vacuum. The residue was purified by silica gel chromatography. Diisopropyl ether was added to the residue, followed by decantation. The target compound, triphenylsulfonium 1,1,3,3,3-pentafluoro-2-(2-methacryloyloxy-acetoxy)-propane-1-sulfonate was obtained as brown oil (39.3 g, yield 66%). The compound has the following structure.

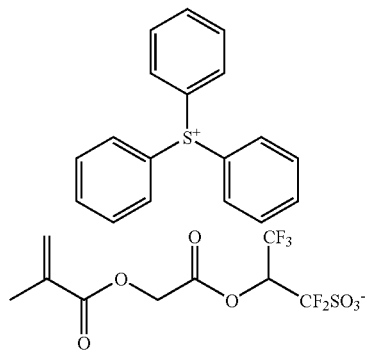

Figure 2:
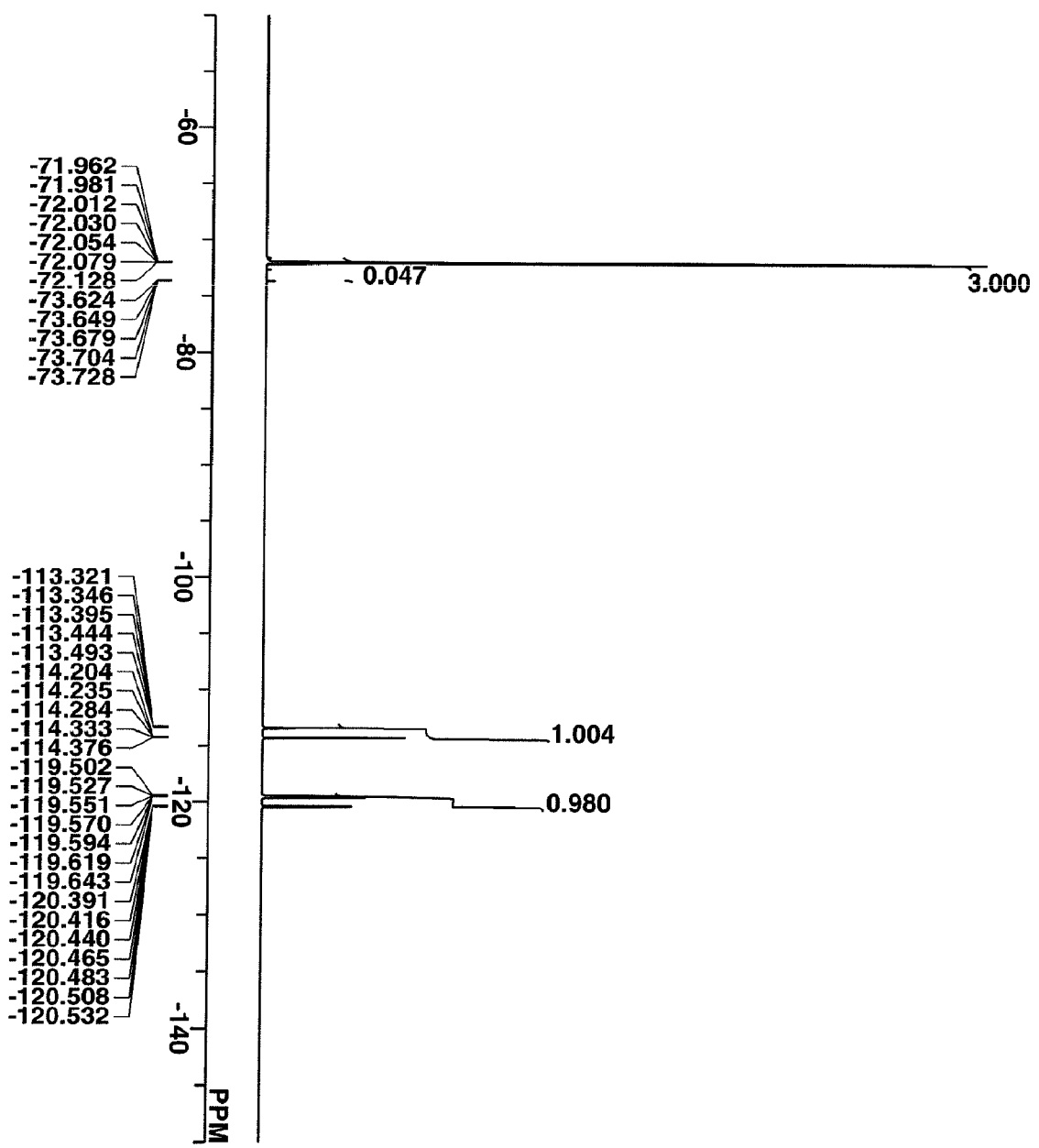
FIG. 2 is a diagram showing the $^{19}$F-NMR spectrum of Monomer 1 in Synthesis Example 2-1.

The compound was analyzed by spectroscopy. The nuclear magnetic resonance spectra, $^1$H-NMR and $^{19}$F-NMR/DMSO-$d_6$ are shown in FIGS. 1 and 2. Note that in $^1$H-NMR, traces of residual solvents (diisopropyl ether, methyl isobutyl ketone, water) were observed. The data of time-of-flight mass spectrometry (TOFMS) are shown below.
TOFMS (MALDI)
 Positive M$^+$263 (corresponding to $(C_6H_5)_3S^+$)
 Negative M$^-$355 (corresponding to $CF_3CH(OCO-C_5H_7O_2)CF_2SO_3^-$)

Analogous compounds were synthesized by following the successive procedures of Synthesis Example 1-19 and Synthesis Example 2-1 aside from using one of PAG2 to PAG8 instead of PAG1, i.e., triphenylsulfonium 2-hydroxy-1,1,3,3,3-pentafluoropropane-1-sulfonate. The compounds correspond to Monomer 1 wherein the cation is replaced by 4-tert-butylphenyldiphenylsulfonium, 4-tert-butoxyphenyldiphenylsulfonium, tris(4-methylphenyl)sulfonium, tris(4-tert-butylphenyl)sulfonium, bis(4-tert-butylphenyl)iodonium, dimethylphenylsulfonium, and phenacyltetrahydrothiophenium.

Synthesis Example 2-2

Synthesis of triphenylsulfonium 1,1,3,3,3-pentafluoro-2-(4-methacryloyloxy-butyryloxy)-propane-1-sulfonate (Monomer 2)

To 20 g of dimethylformamide were added 5.4 g (9.0 mmol) of triphenylsulfonium 2-(4-chlorobutyryloxy)-1,1,3,3,3-pentafluoropropane-1-sulfonate synthesized in Synthesis Example 1-20, 1.2 g (11 mmol) of sodium methacrylate, 0.20 g (1.4 mmol) of sodium iodide, and 1 mg of 2,2'-methylenebis(6-t-butyl-p-cresol). The mixture was heated and stirred at 90° C. for 12 hours. The reaction solution was allowed to resume room temperature, after which 50 g of water and 80 g of dichloromethane were added. The organic layer was separated and washed with water whereupon dichloromethane was distilled off under vacuum. The residue was combined with 30 g of methyl isobutyl ketone and washed with water whereupon methyl isobutyl ketone was distilled off under vacuum. The residue was purified by silica gel chromatography. The target compound, triphenylsulfonium 1,1,3,3,3-pentafluoro-2-(4-methacryloyloxy-butyryloxy)-propane-1-sulfonate was obtained as brown oil (4.2 g, yield 72%). The compound has the following structure.

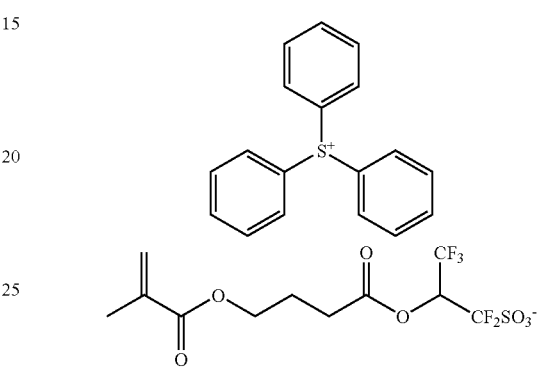

Figure 3:
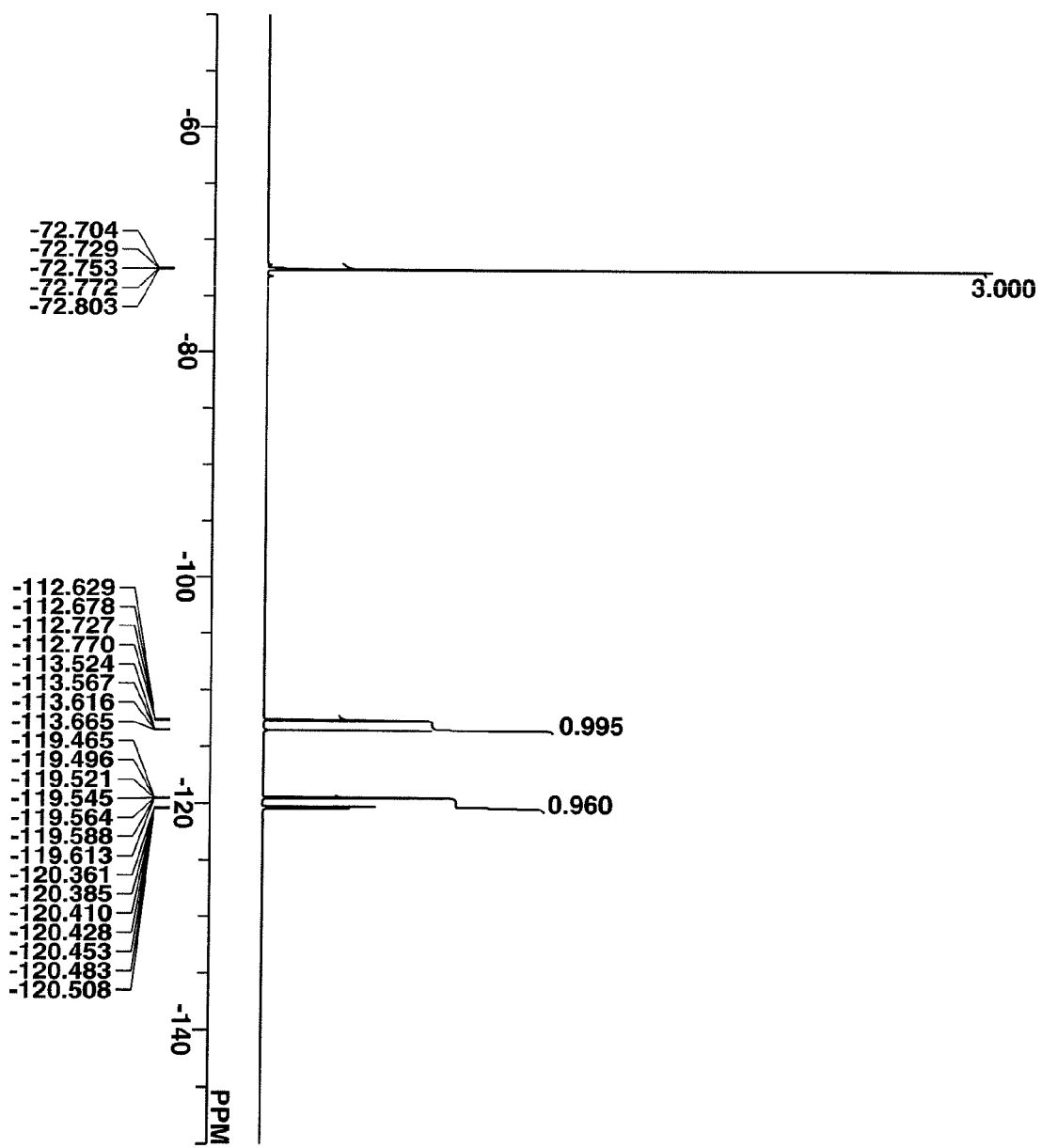
FIG. 3 is a diagram showing the $^{19}$F-NMR spectrum of Monomer 2 in Synthesis Example 2-2.

The compound was analyzed by spectroscopy. The nuclear magnetic resonance spectrum, $^{19}$F-NMR/CDCl$_3$ is shown in FIG. 3. The data of time-of-flight mass spectrometry (TOFMS) are shown below.
TOFMS (MALDI)
 Positive M$^-$263 (corresponding to $(C_6H_5)_3S^+$)
 Negative M$^-$383 (corresponding to $CF_3CH(OCO-C_7H_{11}O_2)CF_2SO_3^-$)

Analogous compounds were synthesized by following the successive procedures of Synthesis Example 1-20 and Synthesis Example 2-2 aside from using one of PAG2 to PAG8 instead of PAG1, i.e., triphenylsulfonium 2-hydroxy-1,1,3,3,3-pentafluoropropane-1-sulfonate. The compounds correspond to Monomer 2 wherein the cation is replaced by 4-tert-butylphenyldiphenylsulfonium, 4-tert-butoxyphenyldiphenylsulfonium, tris(4-methylphenyl)sulfonium, tris(4-tert-butylphenyl)sulfonium, bis(4-tert-butylphenyl)iodonium, dimethylphenylsulfonium, and phenacyltetrahydrothiophenium.

Synthesis Example 2-3

Synthesis of triphenylsulfonium 1,1,3,3,3-pentafluoro-2-(3-methacryloyloxy-adamantane-1-carbonyloxy)-propane-1-sulfonate (Monomer 3)

3-methacryloyloxyadamantanecarboxylic acid was reacted with oxalyl chloride in toluene medium, thus converting to a corresponding carboxylic acid chloride.

To 28.4 g (0.10 mole) of the resulting 3-methacryloyloxyadamantanecarbonyl chloride were added 44.9 g (0.09 mole) of triphenylsulfonium 2-hydroxy-1,1,3,3,3-pentafluoropropane-1-sulfonate in Synthesis Example 1-11 and 20 g of methylene chloride, which was ice cooled. To the solution, a solution of 10.1 g (0.10 mole) of triethylamine and 2.2 g (0.02 mole) of N,N-dimethylaminopyridiene in 45 g of methylene chloride was added such that the temperature might not exceed 5° C., followed by stirring at room temperature for 7 hours. Thereafter, 105 g of 5% dilute hydrochloric acid was added. The organic layer was separated and washed with water whereupon methylene chloride was distilled off under vacuum. The residue was combined with 250 g of methyl isobutyl ketone and washed with dilute aqueous ammonia and then with water, whereupon the methyl isobutyl ketone was distilled off under vacuum. Diisopropyl ether was added to the residue, followed by decantation. The target compound, triphenylsulfonium 1,1,3,3,3-pentafluoro-2-(3-methacryloyloxy-adamantane-1-carbonyloxy)-propane-1-sulfonate was obtained as brown oil (61.7 g, yield 92%). The compound has the following structure.

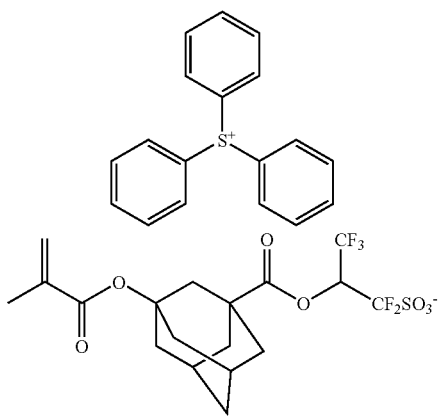

Figure 4:
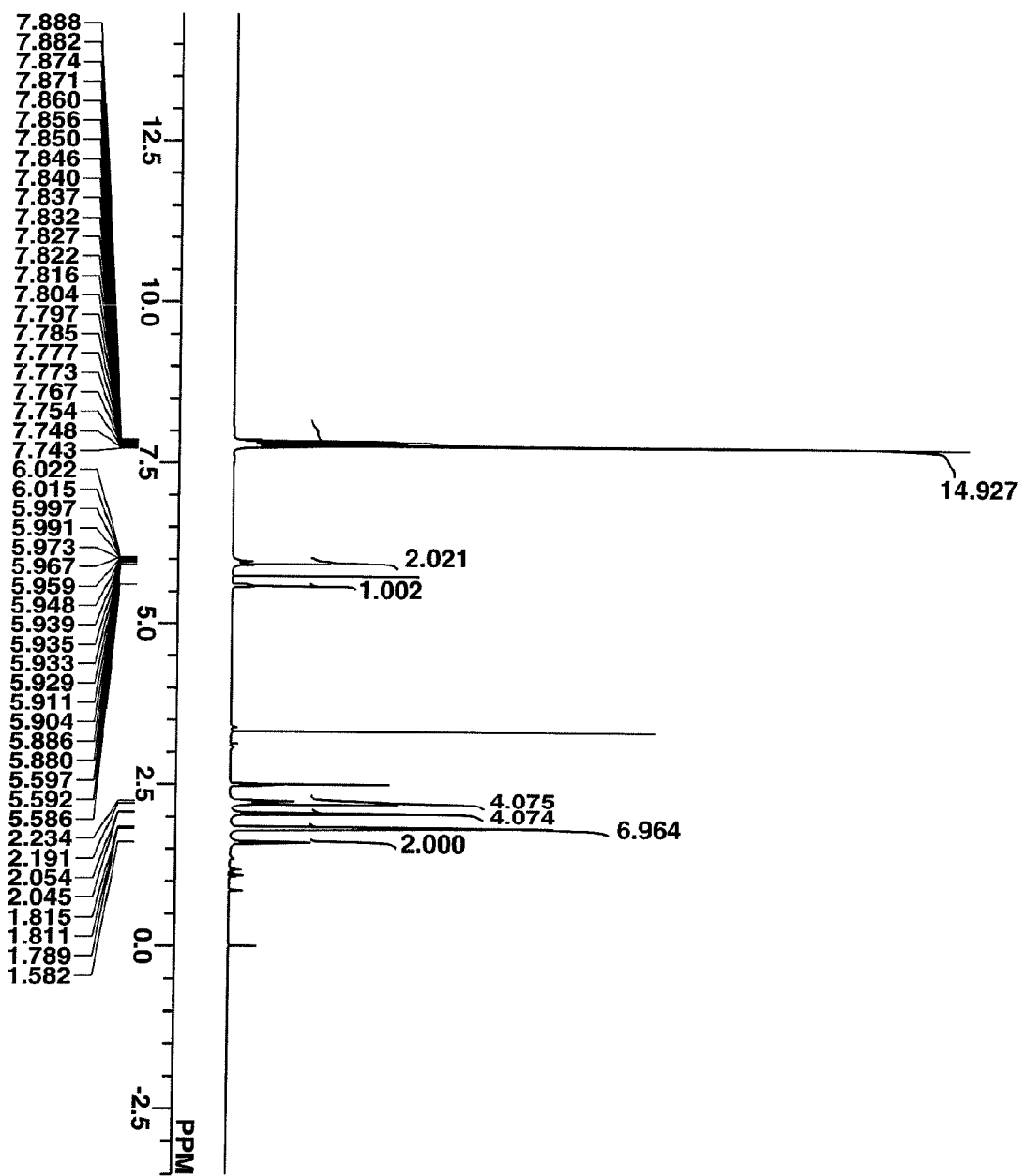
FIG. 4 is a diagram showing the $^1$H-NMR spectrum of Monomer 3 in Synthesis Example 2-3.
Figure 5:
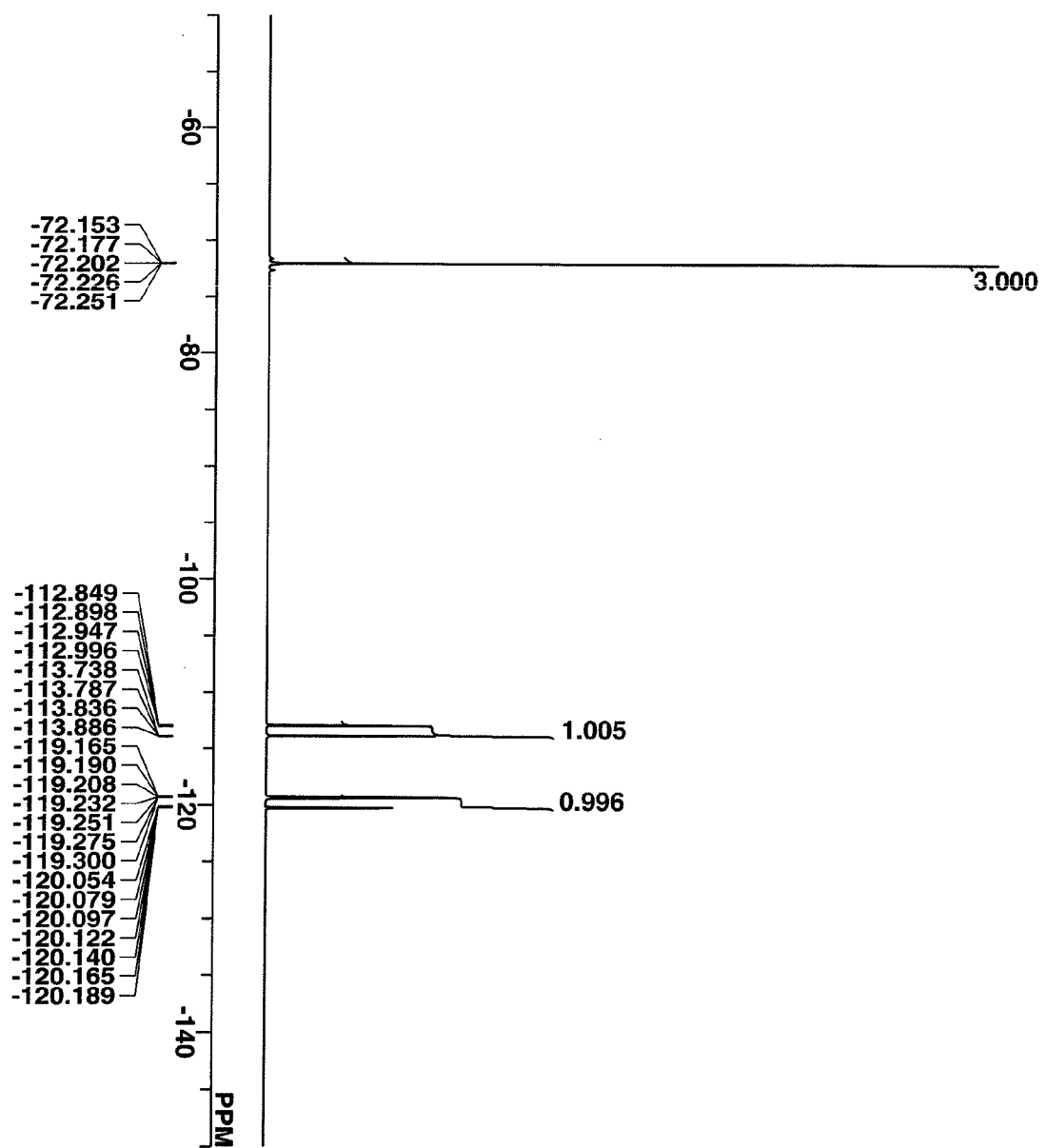
FIG. 5 is a diagram showing the $^{19}$F-NMR spectrum of Monomer 3 in Synthesis Example 2-3.

The compound was analyzed by spectroscopy. The nuclear magnetic resonance spectra, $^1$H-NMR and F-NMR/DMSO-$d_6$ are shown in FIGS. 4 and 5. Note that in $^1$H-NMR, traces of residual solvents (diisopropyl ether, methyl isobutyl ketone, water) were observed. The data of infrared (IR) absorption spectroscopy and time-of-flight mass spectrometry (TOFMS) are shown below.

IR Spectra (KBr, cm$^{-1}$)
3446, 3064, 2917, 2863, 1756, 1710, 1635, 1477, 1448, 1375, 1330, 1251, 1214, 1182, 1091, 993, 927, 898, 750, 684, 640, 574, 551, 518, 501

TOFMS (MALDI)
Positive M$^+$263 (corresponding to $(C_6H_5)_3S^+$)
Negative M$^-$475 (corresponding to $CF_3CH(OCO-C_{14}H_{19}O_2)CF_2SO_3^-$)

Synthesis Example 2-4

Synthesis of triphenylsulfonium 1,1,3,3,3-pentafluoro-2-(2-methacryloyloxy-5-oxo-4-oxa-tricyclo[4.2.1.0$^{3,7}$]nonane-9-carbonyloxy)-propane-1-sulfonate (Monomer 4)

2-methacryloyloxy-5-oxo-4-oxa-tricyclo[4.2.1.0$^{3,7}$]-nonanecarboxylic acid was reacted with oxalyl chloride in toluene medium, thus converting to a corresponding carboxylic acid chloride.

To 2.8 g (0.01 mole) of the resulting 2-methacryloyloxy-5-oxo-4-oxa-tricyclo[4.2.1.0$^{3,7}$]nonanecarbonyl chloride were added 4.9 g (0.01 mole) of triphenylsulfonium 2-hydroxy-1,1,3,3,3-pentafluoropropane-1-sulfonate in Synthesis Example 1-11 and 20 g of methylene chloride, which was ice cooled. To the solution, a solution of 1.0 g (0.01 mole) of triethylamine and 0.2 g (0.002 mole) of N,N-dimethylaminopyridiene in 5 g of methylene chloride was added such that the temperature might not exceed 5° C., followed by stirring at room temperature for 3 hours. Thereafter, 10 g of 5% dilute hydrochloric acid was added. The organic layer was separated and washed with water whereupon methylene chloride was distilled off under vacuum. The residue was combined with 30 g of methyl isobutyl ketone and washed with dilute aqueous ammonia and then with water, whereupon the methyl isobutyl ketone was distilled off under vacuum. The residue was purified by silica gel chromatography. The target compound, triphenylsulfonium 1,1,3,3,3-pentafluoro-2-(2-methacryloyloxy-5-oxo-4-oxatricyclo[4.2.1.0$^{3,7}$]nonane-9-carbonyloxy)-propane-1-sulfonate was obtained as colorless solid (5.0 g, yield 69%). The compound has the following structure.

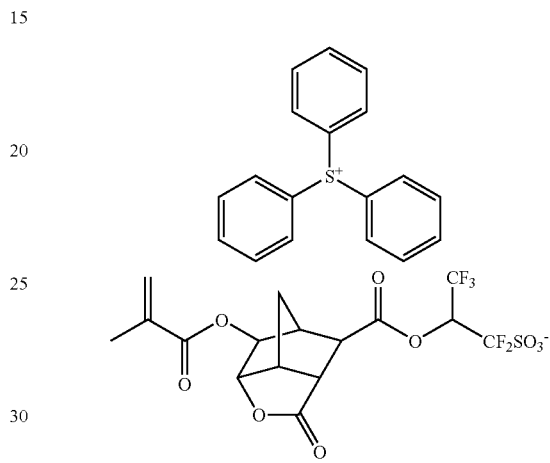

Figure 6:
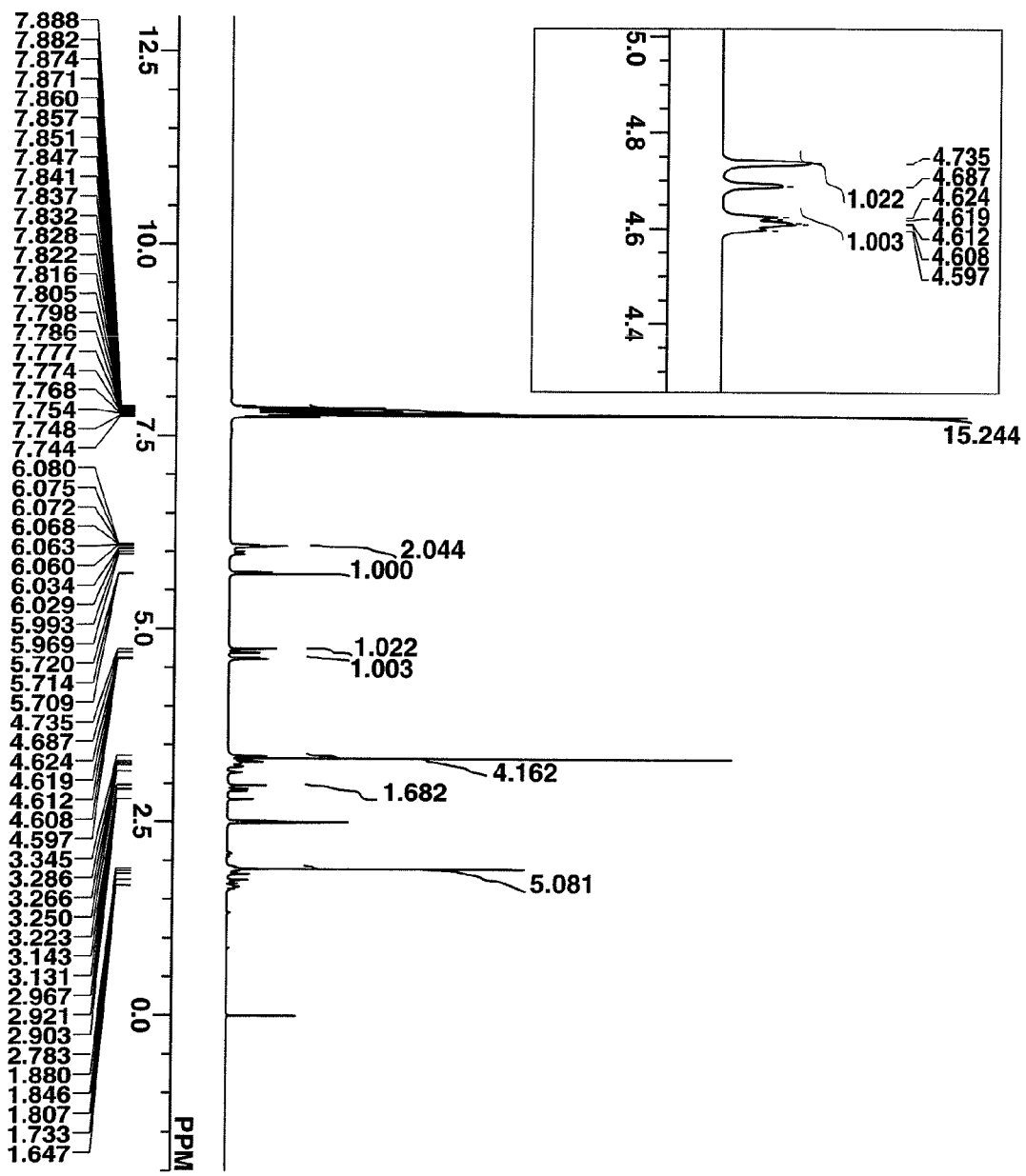
FIG. 6 is a diagram showing the $^1$H-NMR spectrum of Monomer 4 in Synthesis Example 2-4.
Figure 7:
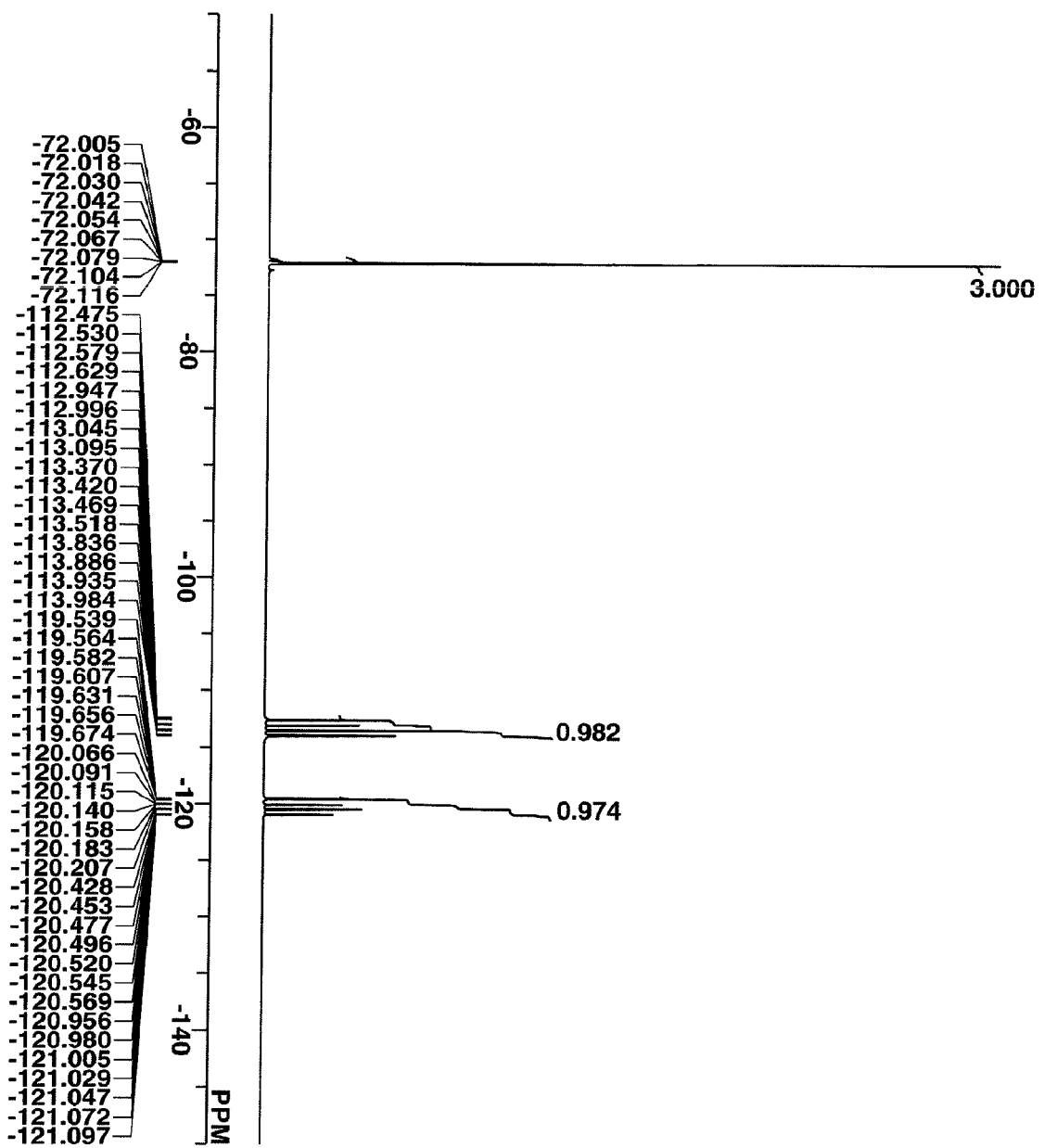
FIG. 7 is a diagram showing the $^{19}$F-NMR spectrum of Monomer 4 in Synthesis Example 2-4.

The compound was analyzed by spectroscopy. The nuclear magnetic resonance spectra, $^1$H-NMR and $^{19}$F-NMR/DMSO-$d_6$ are shown in FIGS. 6 and 7. Note that in $^1$H-NMR, traces of residual solvents (methylene chloride, water) were observed. The data of IR spectroscopy and TOFMS are shown below.

IR Spectra (KBr, cm$^{-1}$)
1785, 1720, 1477, 1448, 1373, 1322, 1253, 1216, 1174, 1112, 1074, 1016, 995, 750, 684, 642, 503

TOFMS (MALDI)
Positive M$^+$263 (corresponding to $(C_6H_5)_3S^+$)
Negative M$^-$477 (corresponding to $CF_3CH(OCO-C_{12}H_{13}O_4)CF_2SO_3^-$)

Synthesis Example 2-5

Synthesis of triphenylsulfonium 1,1,3,3,3-pentafluoro-2-(4-vinyl-benzoyloxy)-propane-1-sulfonate (Monomer 5)

4-vinylbenzoic acid was reacted with oxalyl chloride in toluene medium, thus converting to a corresponding carboxylic acid chloride.

Under ice cooling, 2.0 g (12 mmol) of the resulting 4-vinylbenzoyl chloride in methylene chloride was added dropwise to a mixture of 4.9 g (10 mmol) of triphenylsulfonium 2-hydroxy-1,1,3,3,3-pentafluoropropane-1-sulfonate in Synthesis Example 1-11, 1.21 g (12 mmol) of triethylamine, 0.24 g (2 mmol) of N,N-dimethylaminopyridine, and 20 g of methylene chloride. The reaction mixture was stirred at room temperature for 2 hours. Thereafter, 11 g of 5% dilute hydrochloric acid was added. The organic layer was separated and washed with water whereupon methylene chloride was distilled off under vacuum. The residue was combined with 30 g of methyl isobutyl ketone and washed with dilute aqueous ammonia and then with water, whereupon the methyl isobutyl ketone was distilled off under vacuum. Diisopropyl ether was added to the residue, followed by decantation. The target compound, triphenylsulfonium 1,1,3,3,3-pentafluoro-2-(4-vinyl-benzoyloxy)-propane-1-sulfonate was obtained as colorless oil (5.3 g, yield 85%). The compound has the following structure.

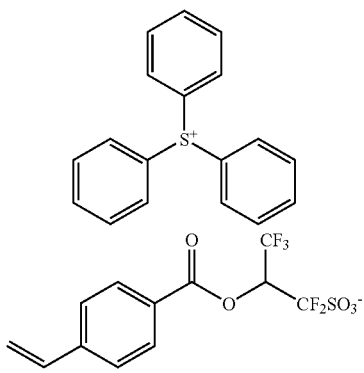

Figure 8:
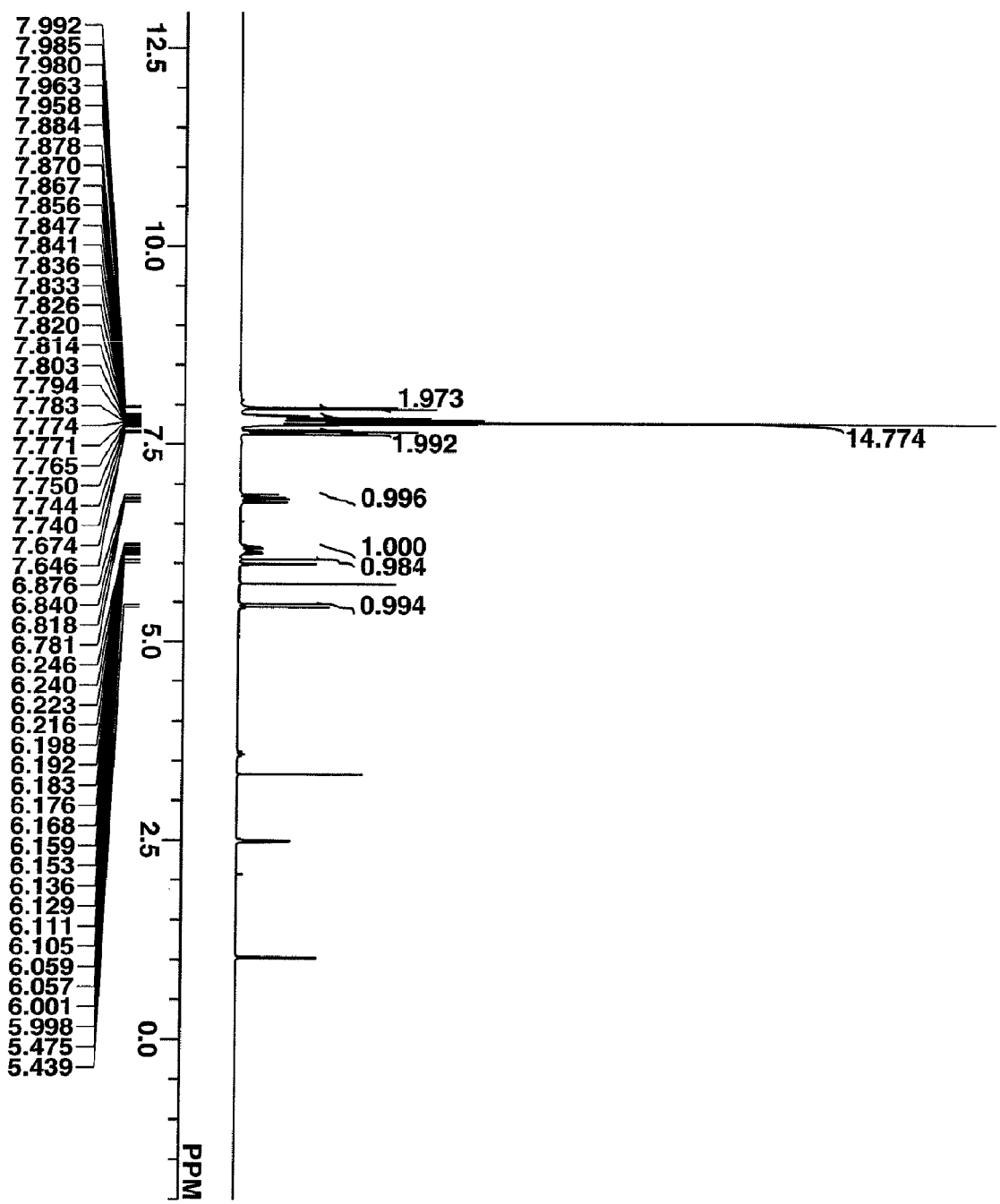
FIG. 8 is a diagram showing the $^1$H-NMR spectrum of Monomer 5 in Synthesis Example 2-5.
Figure 9:
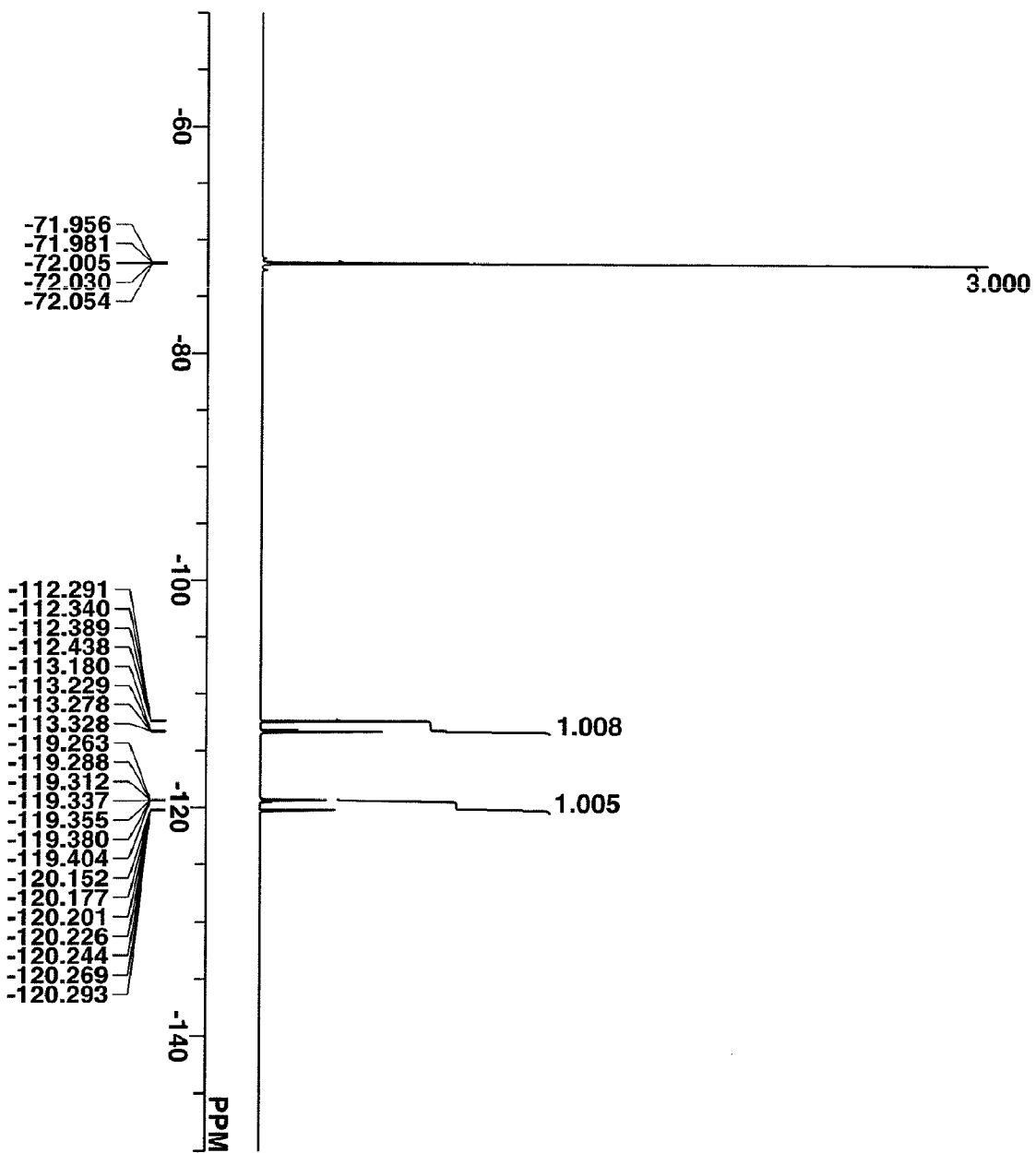
FIG. 9 is a diagram showing the $^{19}$F-NMR spectrum of Monomer 5 in Synthesis Example 2-5.

The compound was analyzed by spectroscopy. The nuclear magnetic resonance spectra, $^1$H-NMR and $^{19}$F-NMR/DMSO-$d_6$ are shown in FIGS. 8 and 9. Note that in $^1$H-NMR, traces of residual solvents (methylene chloride, diisopropyl ether, water) were observed. The data of IR spectroscopy and TOFMS are shown below.
IR Spectra (D-ATR, cm$^{-1}$)
 1739, 1606, 1476, 1447, 1371, 1326, 1244, 1216, 1179, 1162, 1100, 1070, 1013, 992, 901, 860, 839, 777, 745, 711, 681, 638, 603, 562
TOFMS (MALDI)
 Positive M$^-$263 (corresponding to $(C_6H_5)_3S^+$)
 Negative M$^-$359 (corresponding to CF$_3$CH(OCO—C$_8$H$_7$)CF$_2$SO$_2^-$)

Synthesis Example 2-6

Synthesis of triphenylsulfonium 1,1,3,3,3-pentafluoro-2-(4-methacryloyloxy-benzoyloxy)-propane-1-sulfonate (Monomer 6)

4-methacryloyloxybenzoic acid was reacted with oxalyl chloride in toluene medium, thus converting to a corresponding carboxylic acid chloride.
 To 2.4 g (11 mmol) of the resulting 4-methacryloyloxybenzoic chloride were added 4.9 g (10 mmol) of triphenylsulfonium 2-hydroxy-1,1,3,3,3-pentafluoropropane-1-sulfonate in Synthesis Example 1-11 and 20 g of methylene chloride, which was ice cooled. To the solution, a solution of 1.1 g (11 mmol) of triethylamine and 0.2 g (2 mmol) of N,N-dimethylaminopyridiene in 5 g of methylene chloride was added such that the temperature might not exceed 5° C., followed by stirring at room temperature for 3 hours. Thereafter, 11 g of 5% dilute hydrochloric acid was added. The organic layer was separated and washed with water whereupon methylene chloride was distilled off under vacuum. The residue was combined with 30 g of methyl isobutyl ketone and washed with dilute aqueous ammonia and then with water, whereupon the methyl isobutyl ketone was distilled off under vacuum. The residue was washed with diisopropyl ether and purified by silica gel chromatography. The target compound, triphenylsulfonium 1,1,3,3,3-pentafluoro-2-(4-methacryloyloxy-benzoyloxy)-propane-1-sulfonate was obtained as colorless oil (6.0 g, yield 88%). The compound has the following structure.

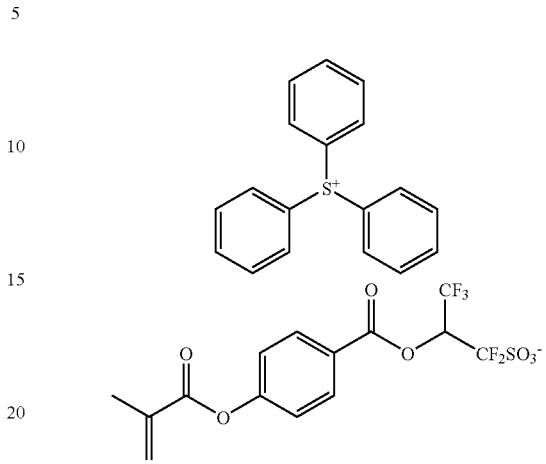

Figure 10:
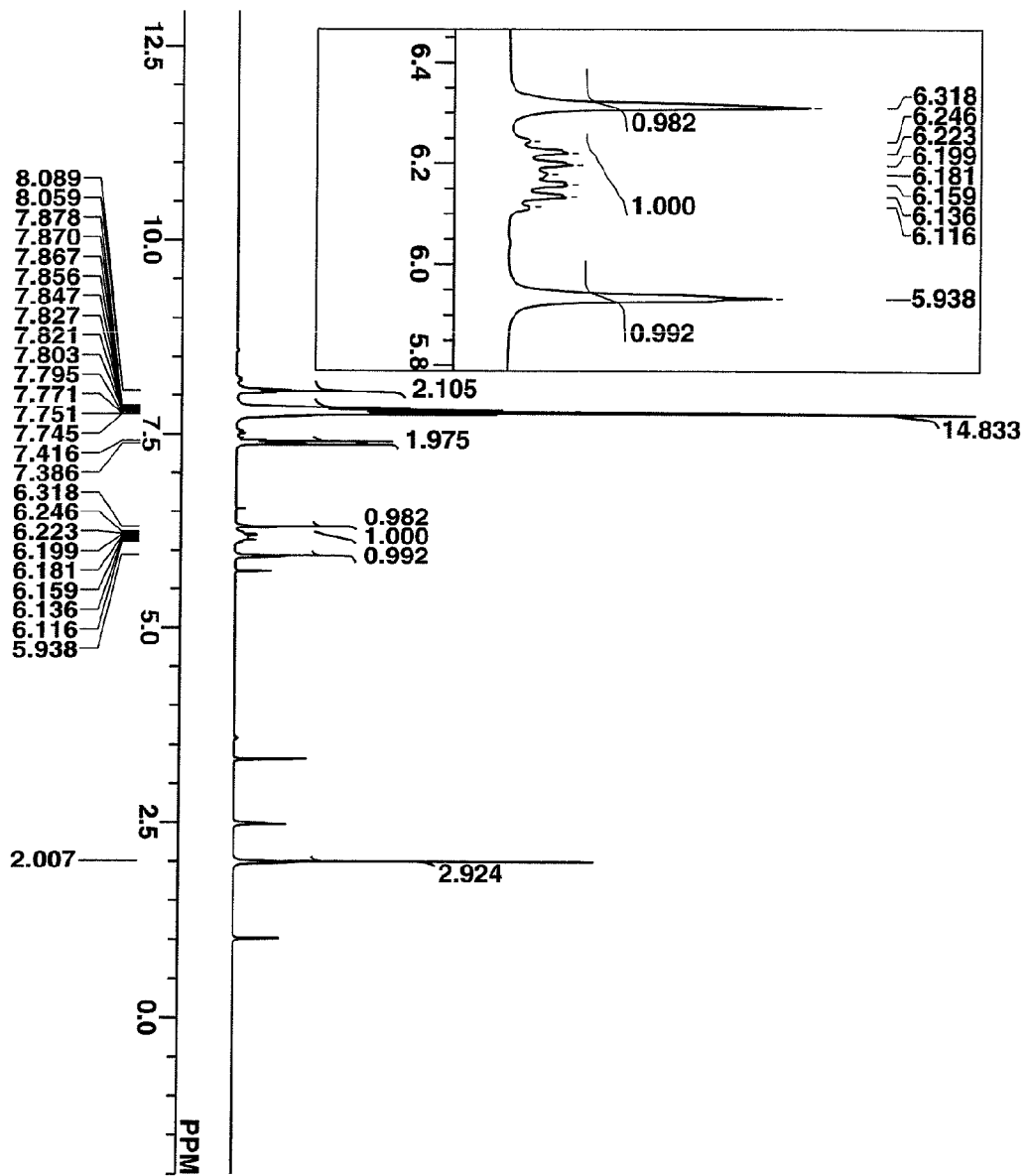
FIG. 10 is a diagram showing the $^1$H-NMR spectrum of Monomer 6 in Synthesis Example 2-6.
Figure 11:
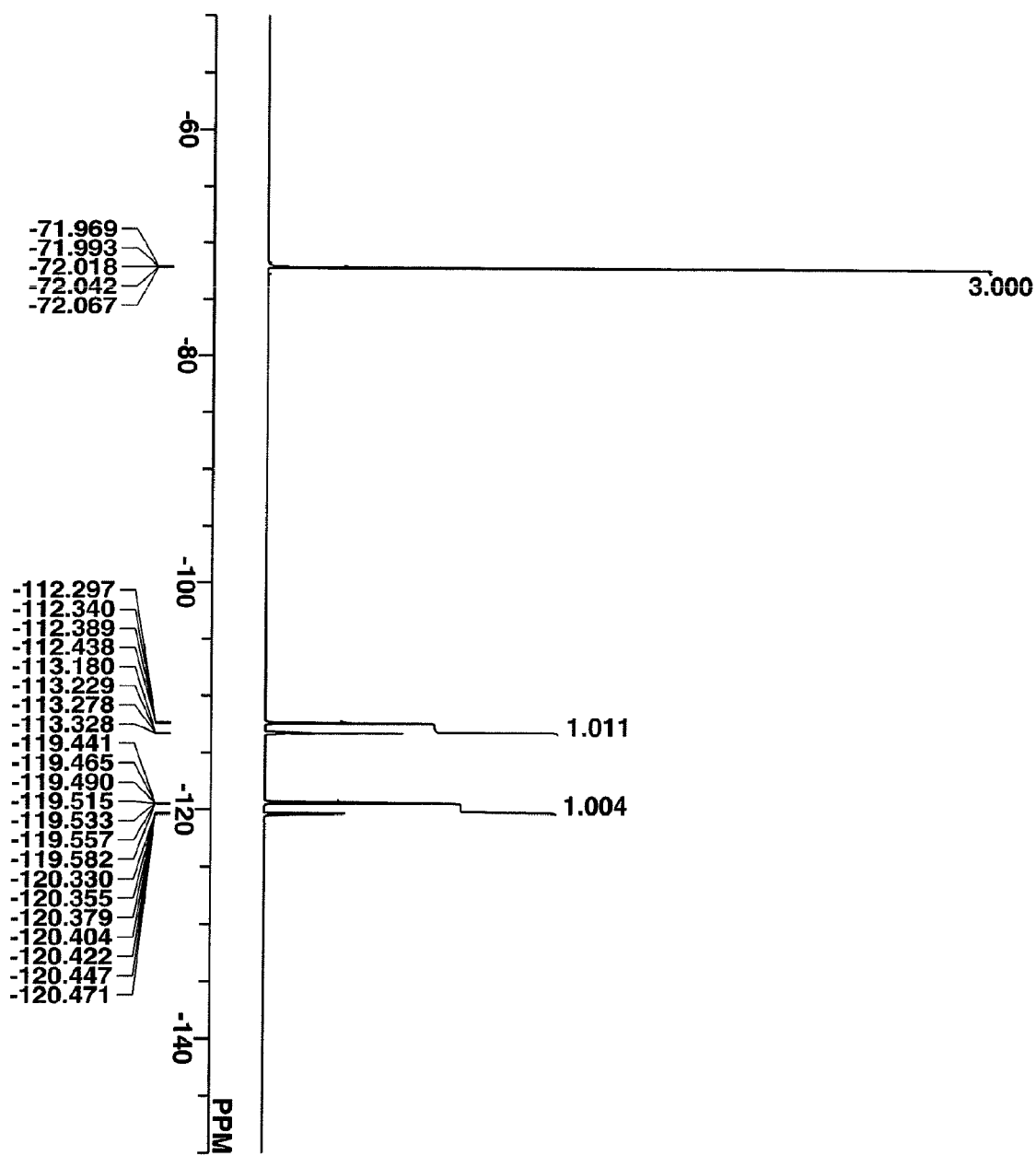
FIG. 11 is a diagram showing the $^{19}$F-NMR spectrum of Monomer 6 in Synthesis Example 2-6.

The compound was analyzed by spectroscopy. The nuclear magnetic resonance spectra, $^1$H-NMR and $^{19}$F-NMR/DMSO-$d_6$ are shown in FIGS. 10 and 11. Note that in $^1$H-NMR, traces of residual solvents (methylene chloride, diisopropyl ether, water) were observed. The data of IR spectroscopy and TOFMS are shown below.
IR Spectra (D-ATR, cm$^{-1}$)
 1737, 1601, 1504, 1476, 1447, 1372, 1321, 1245, 1208, 1184, 1160, 1094, 1071, 1013, 993, 945, 902, 836, 746, 682, 637, 619, 572, 563
TOFMS (MALDI)
 Positive M$^+$263 (corresponding to $(C_6H_5)_3S^+$)
 Negative M$^-$417 (corresponding to CF$_3$CH(OCO—C$_{10}$H$_9$O$_2$)CF$_2$SO$_3^-$)

Synthesis Example 2-7

Synthesis of triphenylsulfonium 1,1,3,3,3-pentafluoro-2-(6-methacryloyloxy-naphthalene-2-carbonyloxy)-propane-1-sulfonate (Monomer 7)

6-methacryloyloxy-naphthalene-2-carboxylic acid was reacted with oxalyl chloride in toluene medium, thus converting to a corresponding carboxylic acid chloride.
 To 3.0 g (11 mmol) of the resulting 6-methacryloyloxynaphthalene-2-carboxylic acid chloride were added 4.9 g (10 mmol) of triphenylsulfonium 2-hydroxy-1,1,3,3,3-pentafluoropropane-1-sulfonate in Synthesis Example 1-11 and 20 g of methylene chloride, which was ice cooled. To the solution, a solution of 1.1 g (11 mmol) of triethylamine and 0.2 g (2 mmol) of N,N-dimethylaminopyridine in 5 g of methylene chloride was added such that the temperature might not exceed 5° C., followed by stirring at room temperature for 3 hours. Thereafter, 11 g of 5% dilute hydrochloric acid was added. The organic layer was separated and washed with water whereupon methylene chloride was distilled off under vacuum. The residue was combined with 30 g of methyl isobutyl ketone and washed with dilute aqueous ammonia and then with water, whereupon the methyl isobutyl ketone was distilled off under vacuum. The residue was washed with diisopropyl ether and purified by silica gel chromatography. The target compound, triphenylsulfonium 1,1,3,3,3-pentafluoro-2-(6-methacryloyloxy-naphthalene-2-carbonyloxy)-propane-1-sulfonate was obtained as colorless solid (6.5 g, yield 89%). The compound has the following structure.

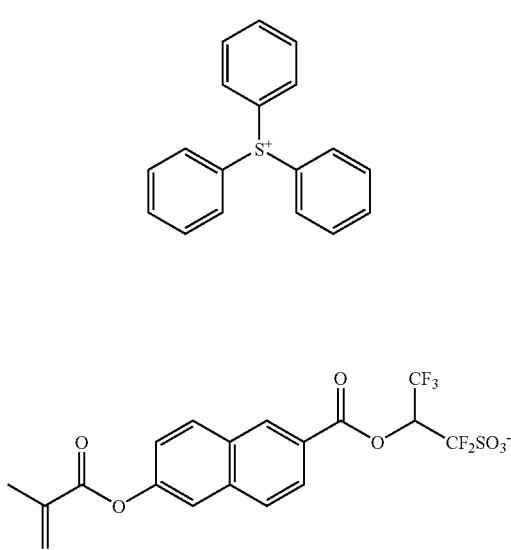

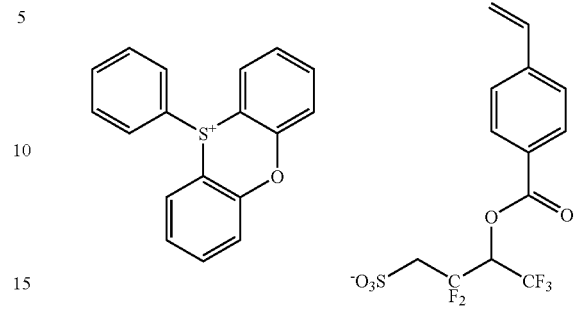

Figure 12:
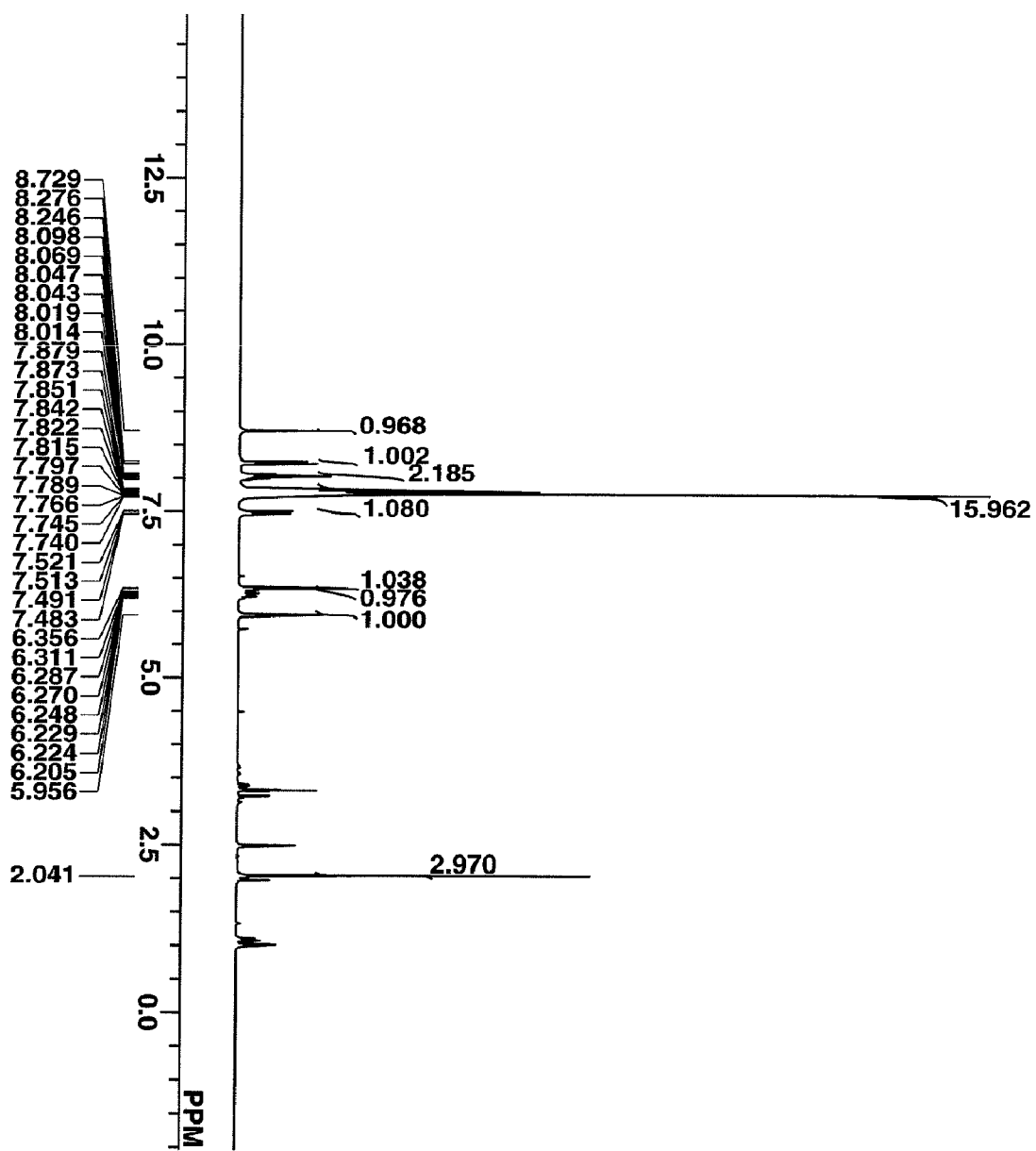
FIG. 12 is a diagram showing the $^1$H-NMR spectrum of Monomer 7 in Synthesis Example 2-7.
Figure 13:
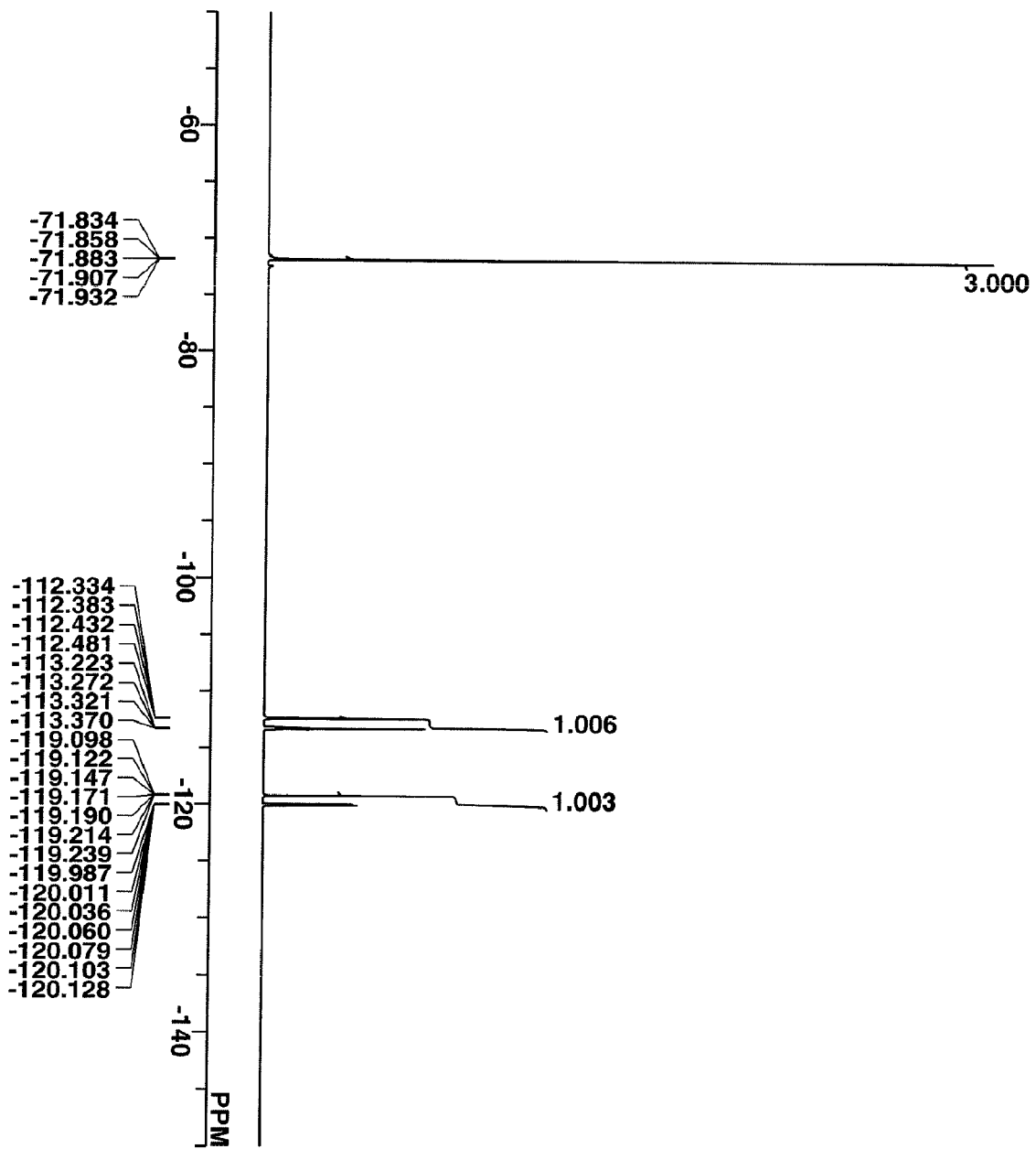
FIG. 13 is a diagram showing the $^{19}$F-NMR spectrum of Monomer 7 in Synthesis Example 2-7.

The compound was analyzed by spectroscopy. The nuclear magnetic resonance spectra, $^1$H-NMR and $^{19}$F-NMR/DMSO-$d_6$ are shown in FIGS. 12 and 13. Note that in $^1$H-NMR, traces of residual solvents (methylene chloride, diisopropyl ether, water) were observed. The data of IR spectroscopy and TOFMS are shown below.

IR Spectra (D-ATR, cm$^{-1}$)

1732, 1630, 1475, 1447, 1373, 1320, 1247, 1216, 1183, 1148, 1134, 1097, 1071, 992, 947, 925, 894, 827, 807, 743, 682, 637, 606

TOFMS (MALDI)

Positive M$^+$263 (corresponding to $(C_6H_5)_3S^+$)

Negative M$^-$467 (corresponding to CF$_3$CH(OCO—C$_{14}$H$_{11}$O$_2$)CF$_2$SO$_3^-$)

Analogous compounds were synthesized by following the procedure of Synthesis Examples 2-3 to 2-7 aside from using one of PAG2 to PAG8 instead of PAG1, i.e., triphenylsulfonium 2-hydroxy-1,1,3,3,3-pentafluoropropane-1-sulfonate. The compounds correspond to Monomers 3 to 7 wherein the cation is replaced by 4-tert-butylphenyldiphenylsulfonium, 4-tert-butoxyphenyldiphenylsulfonium, tris(4-methylphenyl)sulfonium, tris(4-tert-butylphenyl)sulfonium, bis(4-tert-butylphenyl)iodonium, dimethylphenylsulfonium, and phenacyltetrahydrothiophenium.

Synthesis Example 2-8

Synthesis of 10-phenylphenoxathiinum 2-(4-vinylbenzoyloxy)-1,1,3,3,3-pentafluoropropane-1-sulfonate (Monomer 8)

In the same procedure as above, 10-phenylphenoxathiinum 2-hydroxy-1,1,3,3,3-pentafluoropropane-1-sulfonate was synthesized. Then, acylation was conducted as in Synthesis Example 2-5 and recrystallization was conducted from diisopropyl ether, obtaining the target compound. White crystals (yield 89%). The compound has the following structure.

Figure 14:
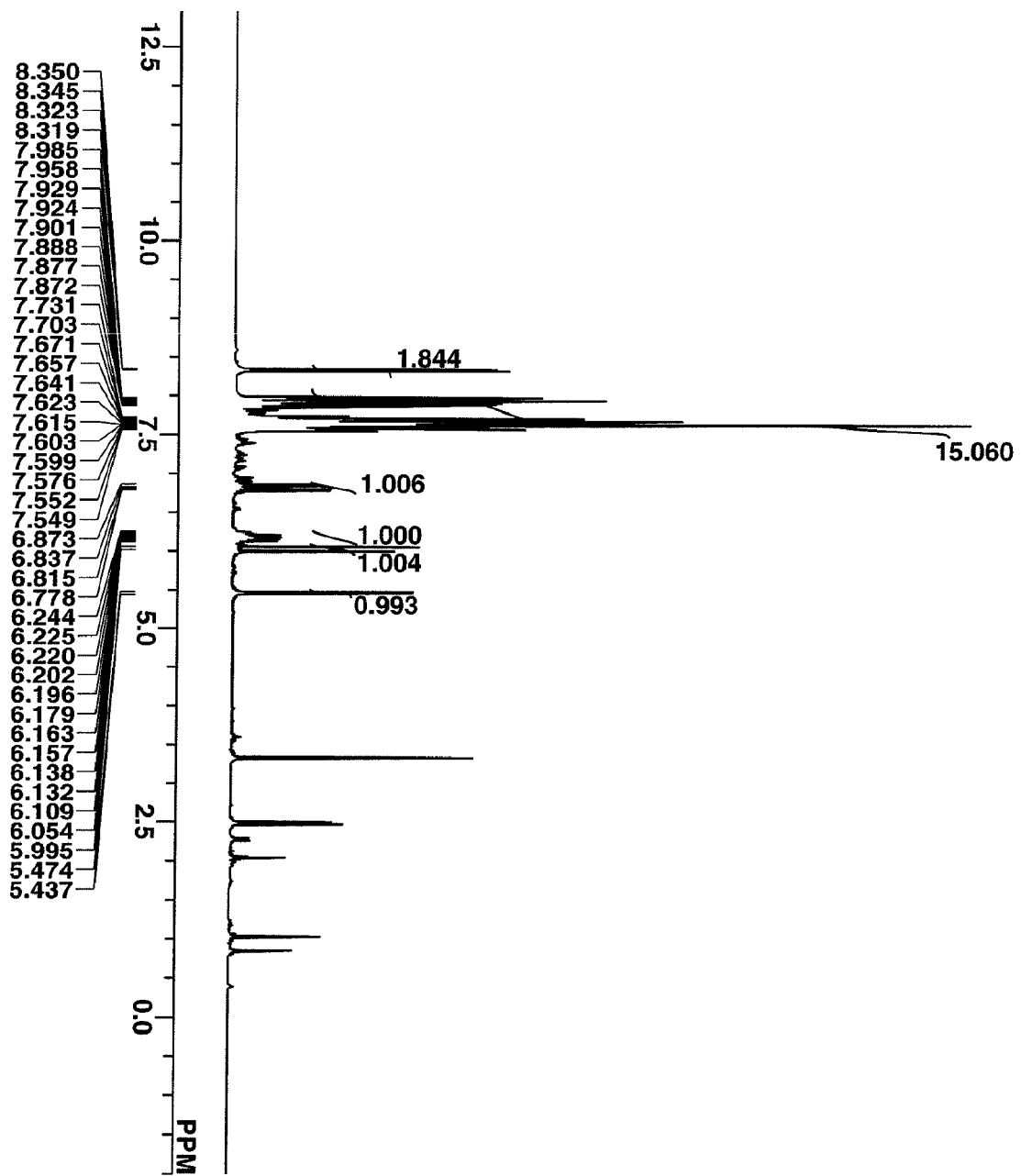
FIG. 14 is a diagram showing the $^1$H-NMR spectrum of Monomer 8 in Synthesis Example 2-8.
Figure 15:
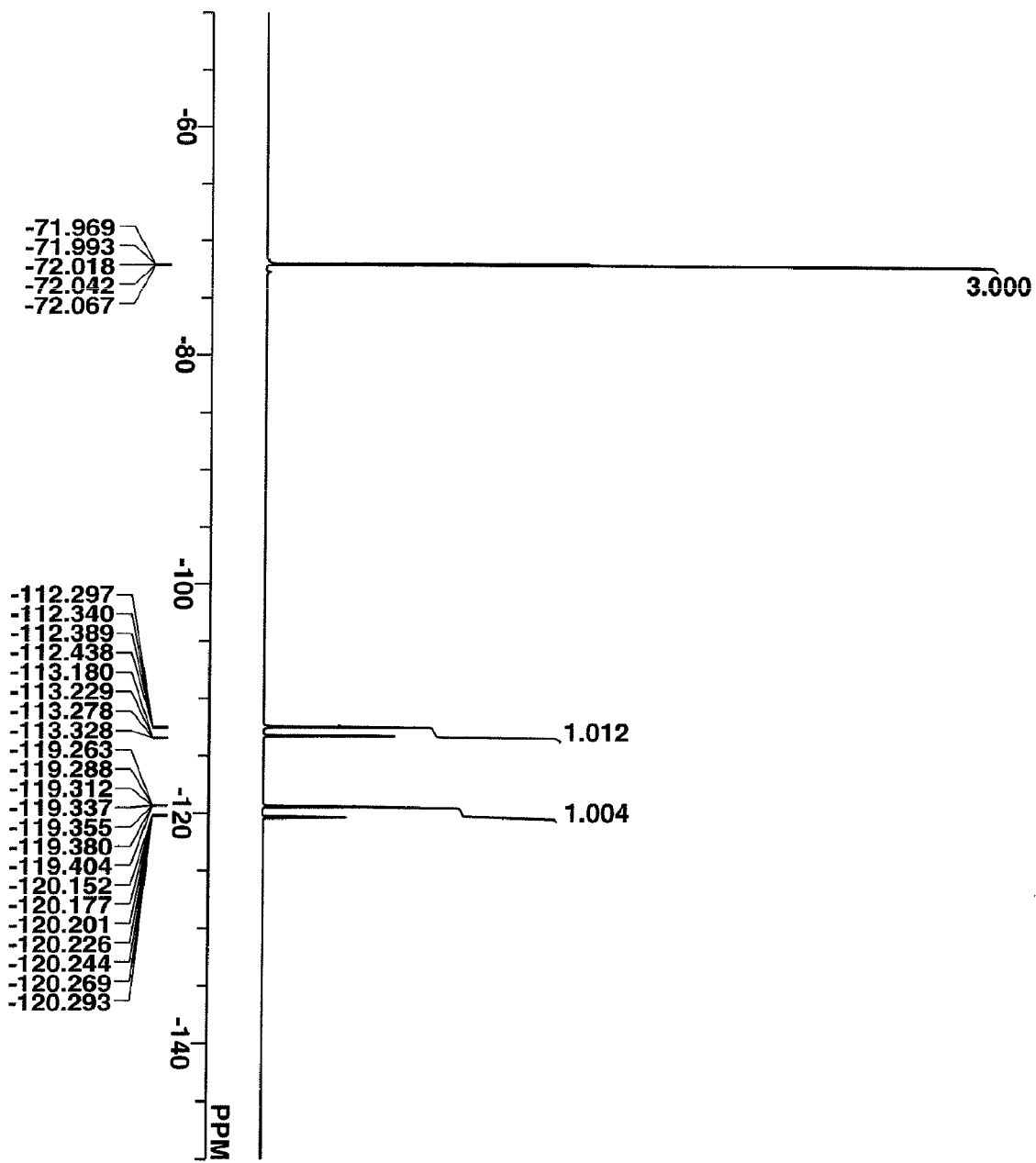
FIG. 15 is a diagram showing the $^{19}$F-NMR spectrum of Monomer 8 in Synthesis Example 2-8.

The compound was analyzed by spectroscopy. The nuclear magnetic resonance spectra, $^1$H-NMR and $^{19}$F-NMR/DMSO-$d_6$ are shown in FIGS. 14 and 15. Note that in $^1$H-NMR, traces of residual solvents (diisopropyl ether, methylisobutyl ketone, water) were observed. The data of IR spectroscopy and TOFMS are shown below.

IR Spectra (D-ATR, cm$^{-1}$)

1742, 1460, 1441, 1255, 1216, 1179, 1166, 1122, 1101, 1072, 991, 762, 708, 639

TOFMS (MALDI)

Positive M$^+$277 (corresponding to $C_{18}H_{13}OS^+$)

Negative M$^-$359 (corresponding to CF$_3$CH(OCO—C$_8$H$_7$)CF$_2$SO$_3^-$)

Polymers within the scope of the invention were synthesized according to the following formulation.

Synthesis Example 3-1

Synthesis of Polymer 1

A flask under a nitrogen blanket was charged with 2.34 g of triphenylsulfonium 1,1,3,3,3-pentafluoro-2-(2-methacryloyloxy-acetoxy)-propane-1-sulfonate, 3.13 g 3-ethyl-3-exo-tetracyclo[4.4.0.1$^{2,5}$.1$^{7,10}$]dodecanyl methacrylate, 2.18 g of 4-hydroxyphenyl methacrylate, 2.54 g of 4,8-dioxatricyclo [4.2.1.0$^{3,7}$]nonan-5-on-2-yl methacrylate, 2.68 g of 3-hydroxy-1-adamantyl methacrylate, 0.31 g of 2,2'-azobisisobutyronitrile, and 17.5 g of methyl ethyl ketone (MEK), to form a monomer solution. Another flask under a nitrogen blanket was charged with 5.8 g of MEK, which was heated to 80° C. with stirring and to which the monomer solution was added dropwise over 4 hours. After the completion of dropwise addition, the polymerization solution was stirred for 2 hours while keeping the temperature of 80° C. It was then cooled to room temperature. The polymerization solution was added dropwise to a mixture of 10 g of MEK and 90 g of hexane, after which the precipitated copolymer was filtered. The copolymer was washed twice with a solvent mixture of 18.5 g of MEK and 41.5 g of hexane and then dried in vacuum at 50° C. for 20 hours. The copolymer was obtained in white powder solid form (8.96 g, yield 90%). It is designated Polymer 1, having the following formula.

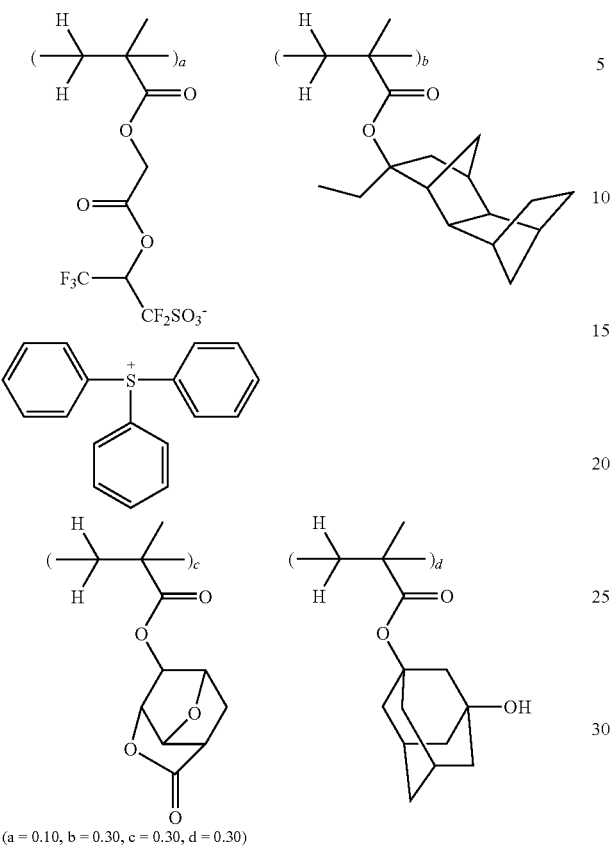

Polymer 1

(a = 0.10, b = 0.30, c = 0.30, d = 0.30)

Synthesis Examples 3-2 to 3-31, 3-40 to 3-42 and Comparative Synthesis Examples 1-1 to 1-2

Synthesis of Polymers 2 to 31, 44 to 46, Comparative Polymers 40 and 41

Resins shown in Table 1 were prepared by the same procedure as Example 3-1 except that the type and proportion of monomers were changed. The structure of the units in Table 1 is shown in Tables 2 to 6. Note that the ratio of incorporated units in Table 1 is expressed in a molar ratio.

Synthesis Examples 3-32 to 3-36 and Comparative Synthesis Example 1-3

Synthesis of Polymers 32 to 36 and Comparative Polymer 42

Each of Polymers 32 to 36 and 42 was obtained by preparing a polymer (Polymers 26 to 31) according to the formulation described above and dissolving it in a solvent mixture of methanol and tetrahydrofuran. Oxalic acid was added to the solution whereupon deprotection reaction was allowed to run at 40° C. The reaction solution was neutralized with pyridine and purified by routine re-precipitation, obtaining a polymer having hydroxystyrene units.

Synthesis Examples 3-37 and 3-38 and Comparative Synthesis Example 1-4

Synthesis of Polymers 37 and 38 and Comparative Polymer 43

Polymers 33, 35 and 36 were reacted with 1-chloro-1-methoxy-2-methylpropane under basic conditions, obtaining the target Polymers 37 and 38 and Comparative Polymer 43.

With respect to the deprotection and protection of polyhydroxystyrene derivatives in Synthesis Examples 3-32 to 3-38 and Comparative Synthesis Examples 1-3 and 1-4, reference should be made to JP-A 2004-115630 and JP-A 2005-8766.

Synthesis Example 3-39

Synthesis of Polymer 39

In accordance with the teachings of JP 3796560, JP 3238465 and JP 3865048, Polymer 32 (4-hydroxystyrene/4-tert-amyloxystyrene copolymer) was reacted with PAG9, triphenylsulfonium 2-(2-chloroacetoxy)-1,1,3,3,3-pentafluoropropane-1-sulfonate under basic conditions, yielding the target Polymer 39.

TABLE 1

| | Resin | Unit 1 (ratio) | Unit 2 (ratio) | Unit 3 (ratio) | Unit 4 (ratio) | Unit 5 (ratio) | Unit 6 (ratio) |
|---|---|---|---|---|---|---|---|
| Synthesis Example 3-1 | Polymer 1 | PM-1M (0.10) | A-1M (0.30) | B-3M (0.30) | B-1M (0.30) | — | — |
| Synthesis Example 3-2 | Polymer 2 | PM-2M (0.10) | A-1M (0.30) | B-3M (0.30) | B-1M (0.30) | — | — |
| Synthesis Example 3-3 | Polymer 3 | PM-3M (0.10) | A-1M (0.30) | B-3M (0.30) | B-1M (0.30) | — | — |
| Synthesis Example 3-4 | Polymer 4 | PM-4M (0.10) | A-1M (0.30) | B-3M (0.30) | B-1M (0.30) | — | — |
| Synthesis Example 3-5 | Polymer 5 | PM-5M (0.10) | A-1M (0.30) | B-3M (0.30) | B-1M (0.30) | — | — |
| Synthesis Example 3-6 | Polymer 6 | PM-1M (0.10) | A-1M (0.30) | B-3M (0.30) | B-1M (0.20) | — | — |
| Synthesis Example 3-7 | Polymer 7 | PM-3M (0.10) | A-1M (0.30) | B-3M (0.30) | B-1M (0.20) | — | — |
| Synthesis Example 3-8 | Polymer 8 | PM-4M (0.10) | A-1M (0.30) | B-3M (0.30) | B-1M (0.20) | — | — |
| Synthesis Example 3-9 | Polymer 9 | PM-1M (0.10) | A-1M (0.30) | B-3M (0.30) | B-7M (0.30) | — | — |
| Synthesis Example 3-10 | Polymer 10 | PM-3M (0.10) | A-1M (0.30) | B-3M (0.30) | B-7M (0.30) | — | — |

TABLE 1-continued

| | Resin | Unit 1 (ratio) | Unit 2 (ratio) | Unit 3 (ratio) | Unit 4 (ratio) | Unit 5 (ratio) | Unit 6 (ratio) |
|---|---|---|---|---|---|---|---|
| Synthesis Example 3-11 | Polymer 11 | PM-4M (0.10) | A-1M (0.30) | B-3M (0.30) | B-7M (0.30) | — | — |
| Synthesis Example 3-12 | Polymer 12 | PM-1M (0.10) | A-1M (0.30) | B-3M (0.30) | B-7M (0.30) | — | — |
| Synthesis Example 3-13 | Polymer 13 | PM-3M (0.10) | A-1M (0.30) | B-3M (0.30) | B-7M (0.30) | — | — |
| Synthesis Example 3-14 | Polymer 14 | PM-4M (0.10) | A-1M (0.30) | B-3M (0.30) | B-7M (0.30) | — | — |
| Synthesis Example 3-15 | Polymer 15 | PM-3M (0.10) | A-1M (0.30) | B-3M (0.30) | B-1M (0.30) | A-3M (0.20) | — |
| Synthesis Example 3-16 | Polymer 16 | PM-3M (0.10) | A-1M (0.30) | B-3M (0.30) | B-2M (0.30) | — | — |
| Synthesis Example 3-17 | Polymer 17 | PM-3M (0.10) | A-1M (0.30) | B-3M (0.30) | B-1M (0.20) | C-3M (0.10) | — |
| Synthesis Example 3-18 | Polymer 18 | PM-3M (0.10) | A-1M (0.30) | B-3M (0.30) | B-1M (0.20) | C-1M (0.10) | — |
| Synthesis Example 3-19 | Polymer 19 | PM-3M (0.10) | A-3M (0.30) | B-3M (0.30) | B-1M (0.20) | C-2M (0.10) | — |
| Synthesis Example 3-20 | Polymer 20 | PM-3M (0.10) | A-1M (0.30) | B-3M (0.30) | B-1M (0.20) | C-4M (0.10) | — |
| Synthesis Example 3-21 | Polymer 21 | PM-3M (0.10) | A-4M (0.30) | B-3M (0.30) | B-1M (0.20) | C-3M (0.10) | — |
| Synthesis Example 3-22 | Polymer 22 | PM-3M (0.10) | A-2M (0.20) | B-3M (0.30) | B-1M (0.30) | A-3M (0.20) | — |
| Synthesis Example 3-23 | Polymer 23 | PM-3M (0.10) | A-1M (0.30) | B-4M (0.30) | B-1M (0.30) | — | — |
| Synthesis Example 3-24 | Polymer 24 | PM-3M (0.10) | A-1M (0.20) | B-6M (0.15) | B-1M (0.30) | B-5M (0.25) | — |
| Synthesis Example 3-25 | Polymer 25 | PM-3M (0.10) | A-1M (0.10) | B-6M (0.25) | B-1M (0.20) | A-5M (0.20) | B-5M (0.15) |
| Synthesis Example 3-26 | Polymer 26 | D-2M (0.65) | D-4M (0.35) | — | — | — | — |
| Synthesis Example 3-27 | Polymer 27 | D-2M (0.70) | D-4M (0.30) | — | — | — | — |
| Synthesis Example 3-28 | Polymer 28 | D-2M (0.90) | D-6M (0.10) | — | — | — | — |
| Synthesis Example 3-29 | Polymer 29 | PM-3M (0.05) | D-2M (0.60) | D-4M (0.35) | — | — | — |
| Synthesis Example 3-30 | Polymer 30 | PM-3M (0.05) | D-2M (0.85) | D-6M (0.10) | — | — | — |
| Synthesis Example 3-31 | Polymer 31 | PM-3M (0.05) | D-2M (0.85) | D-7M (0.10) | — | — | — |
| Synthesis Example 3-32 | Polymer 32 | D-1M (0.65) | D-4M (0.35) | — | — | — | — |
| Synthesis Example 3-33 | Polymer 33 | D-1M (0.90) | D-6M (0.10) | — | — | — | — |
| Synthesis Example 3-34 | Polymer 34 | PM-3M (0.05) | D-1M (0.60) | D-4M (0.35) | — | — | — |
| Synthesis Example 3-35 | Polymer 35 | PM-3M (0.05) | D-1M (0.85) | D-6M (0.10) | — | — | — |
| Synthesis Example 3-36 | Polymer 36 | PM-3M (0.05) | D-1M (0.85) | D-7M (0.10) | — | — | — |
| Synthesis Example 3-37 | Polymer 37 | PM-3M (0.05) | D-1M (0.65) | D-6M (0.10) | D-3M (0.20) | — | — |
| Synthesis Example 3-38 | Polymer 38 | PM-3M (0.05) | D-1M (0.65) | D-7M (0.10) | D-3M (0.20) | — | — |
| Synthesis Example 3-39 | Polymer 39 | PM-6M (0.05) | D-1M (0.60) | D-4M (0.35) | — | — | — |
| Synthesis Example 3-40 | Polymer 44 | PM-8M (0.10) | A-1M (0.30) | B-3M (0.30) | B-7M (0.30) | — | — |
| Synthesis Example 3-41 | Polymer 45 | PM-9M (0.10) | A-1M (0.30) | B-3M (0.30) | B-7M (0.30) | — | — |
| Synthesis Example 3-42 | Polymer 46 | PM-3M (0.05) | B-7M (0.45) | D-7M (0.15) | D-4M (0.35) | — | — |
| Comparative Synthesis Example 1-1 | Comparative Polymer 40 | A-1M (0.30) | B-3M (0.45) | B-1M (0.25) | — | — | — |
| Comparative Synthesis Example 1-2 | Comparative Polymer 41 | PM-7M (0.10) | A-1M (0.30) | B-3M (0.30) | B-1M (0.30) | — | — |
| Comparative Synthesis Example 1-3 | Comparative Polymer 42 | D-1M (0.70) | D-4M (0.30) | — | — | — | — |
| Comparative Synthesis Example 1-4 | Comparative Polymer 43 | D-1M (0.70) | D-6M (0.10) | D-3M (0.20) | — | — | — |

TABLE 2
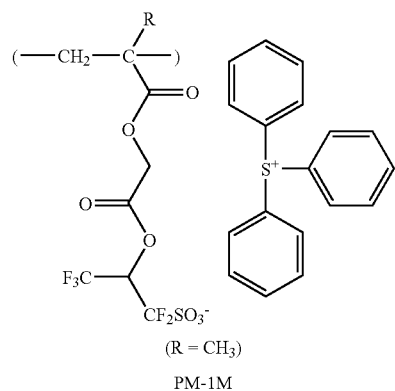
(R = CH₃)
PM-1M
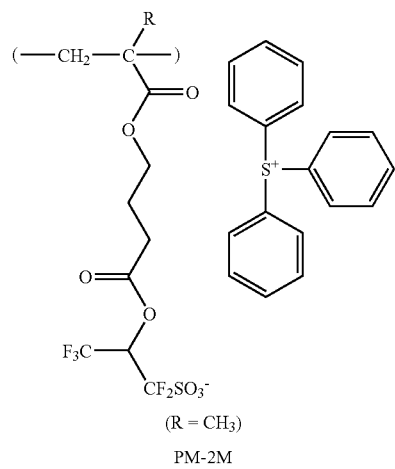
(R = CH₃)
PM-2M
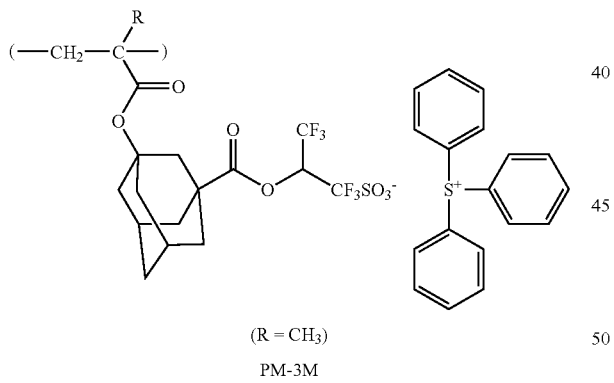
(R = CH₃)
PM-3M
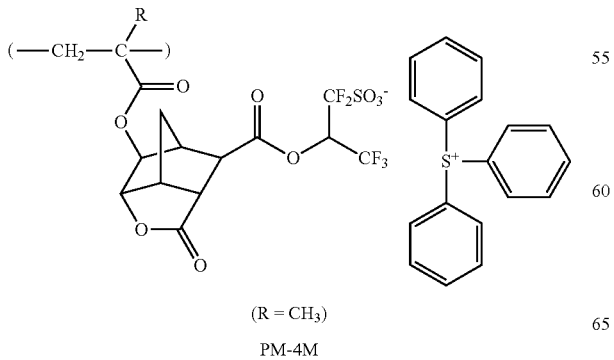
(R = CH₃)
PM-4M
TABLE 2-continued
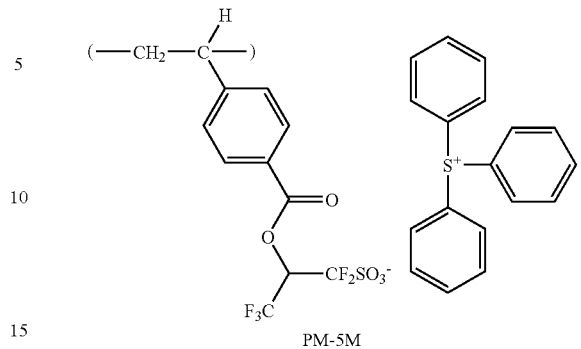
PM-5M
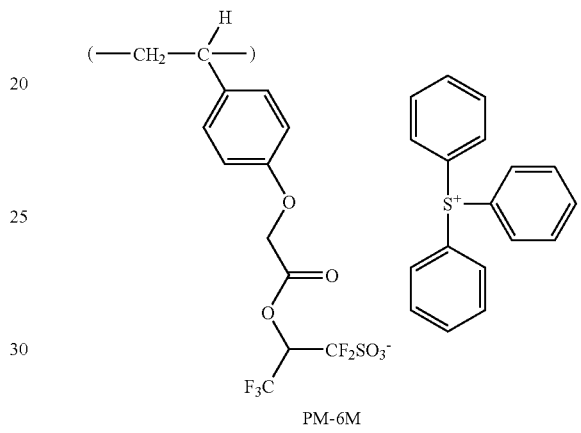
PM-6M
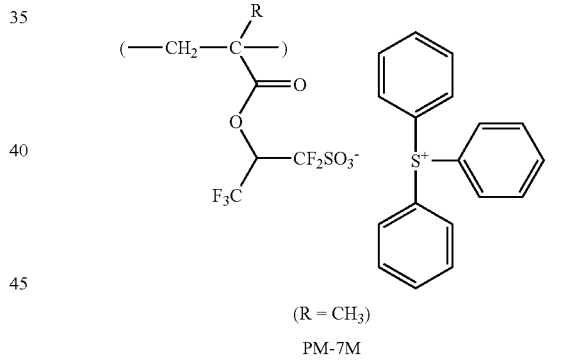
(R = CH₃)
PM-7M
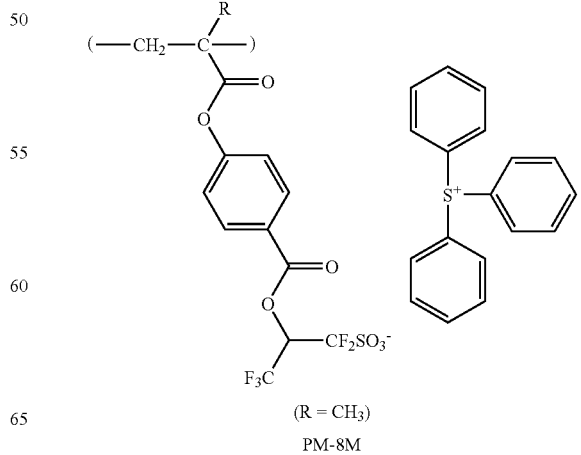
(R = CH₃)
PM-8M TABLE 2-continued
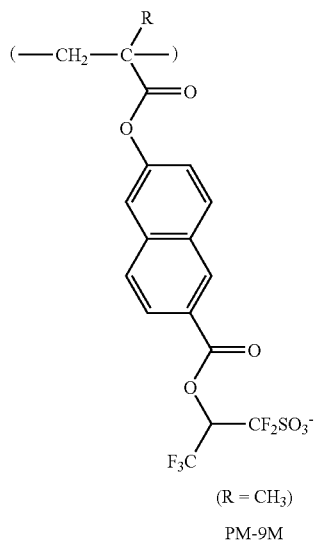
(R = CH₃)
PM-9M
TABLE 3
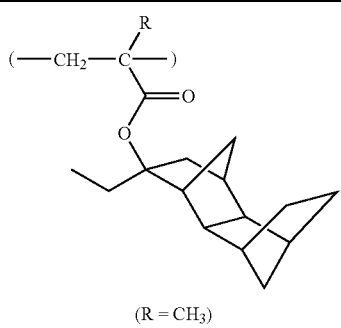
(R = CH₃)
A-1M
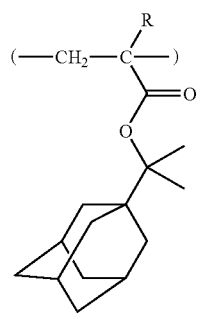
(R = CH₃)
A-2M
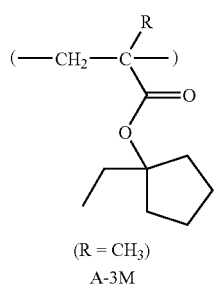
(R = CH₃)
A-3M
TABLE 3-continued
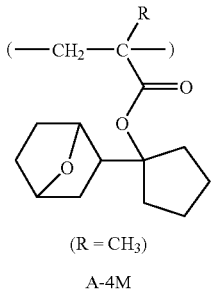
(R = CH₃)
A-4M
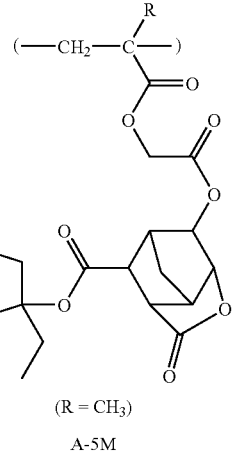
(R = CH₃)
A-5M
TABLE 4
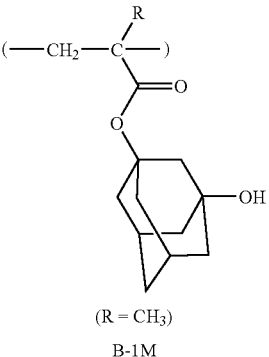
(R = CH₃)
B-1M
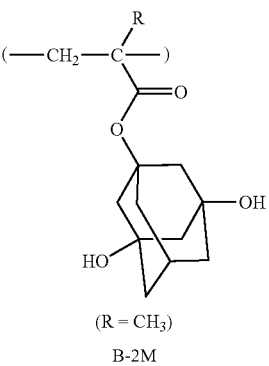
(R = CH₃)
B-2M TABLE 4-continued
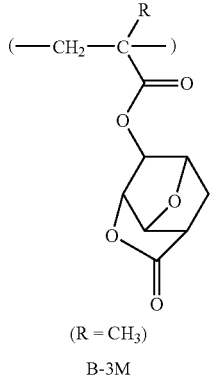
(R = CH₃)
B-3M
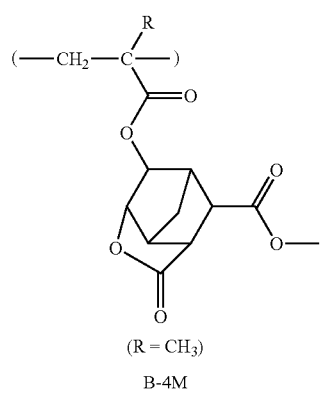
(R = CH₃)
B-4M
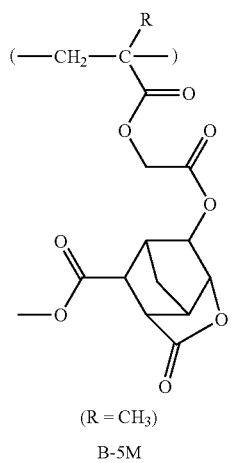
(R = CH₃)
B-5M
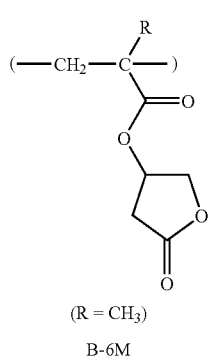
(R = CH₃)
B-6M
TABLE 4-continued
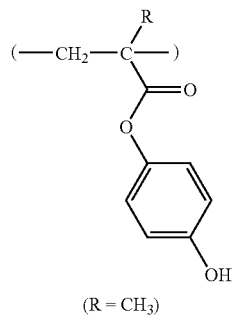
(R = CH₃)
B-7M
TABLE 5
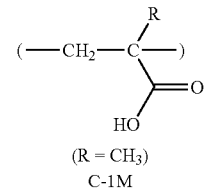
(R = CH₃)
C-1M
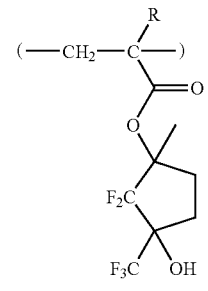
(R = CH₃)
C-2M
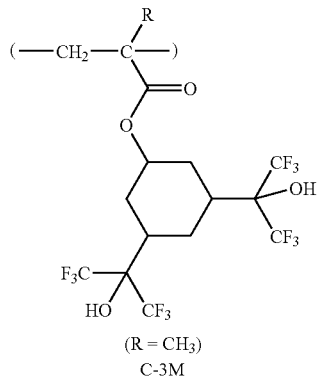
(R = CH₃)
C-3M
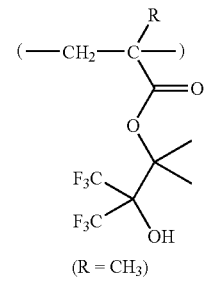
(R = CH₃)
C-4M

TABLE 6

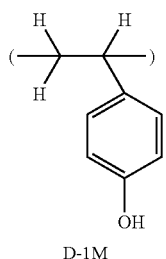

D-1M

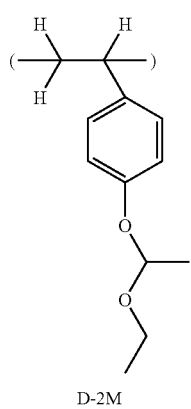

D-2M

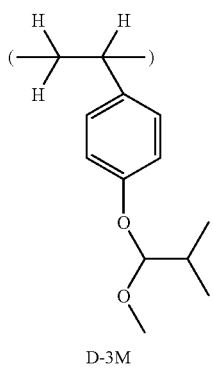

D-3M

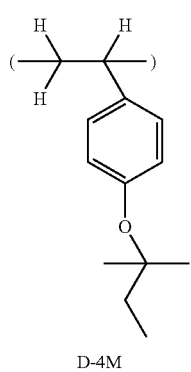

D-4M

TABLE 6-continued

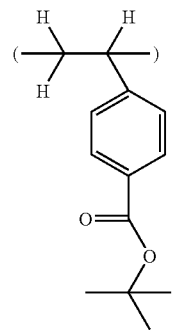

D-5M

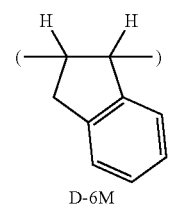

D-6M

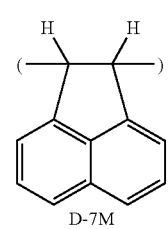

D-7M

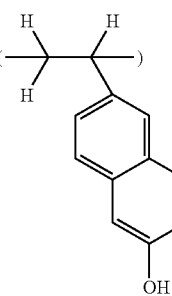

D-8M

Preparation of Resist Compositions

Examples 1-1 to 1-32 & Comparative Examples 1-1 to 1-4

Resist compositions were prepared by using inventive resins (Polymer 1 to 25, 34, 37 to 39 and 44 to 46, abbreviated P-01 to P-25, P-34, P-37 to P-39 and P-44 to P-46) or comparative resins (Comparative Polymers 40 to 43, abbreviated P-40 to P-43) as the base resin, and dissolving the polymer, an acid generator (PAG), and a quencher (Base) in a solvent mixture (PGMEA and CyHO) in accordance with the recipe shown in Table 7. These compositions were each filtered through a Teflon® filter having a pore diameter 0.2 µm, thereby giving inventive resist solutions (R-01 to 29) and comparative resist solutions (R-30 to 33). Note that the solvent contained 0.01 wt % of surfactant (Surfactant 1, Omnova Solutions, Inc.).

TABLE 7

| | Resist | Resin (pbw) | PAG (pbw) | Base (pbw) | Solvent 1 (pbw) | Solvent 2 (pbw) |
|---|---|---|---|---|---|---|
| Example 1-1 | R-01 | P-01 (80) | — | Base-1 (1.10) | PGMEA (896) | CyHO (364) |
| Example 1-2 | R-02 | P-02 (80) | — | Base-1 (1.10) | PGMEA (896) | CyHO (364) |
| Example 1-3 | R-03 | P-03 (80) | — | Base-1 (1.10) | PGMEA (896) | CyHO (364) |
| Example 1-4 | R-04 | P-04 (80) | — | Base-1 (1.10) | PGMEA (896) | CyHO (364) |
| Example 1-5 | R-05 | P-05 (80) | — | Base-1 (1.10) | PGMEA (896) | CyHO (364) |
| Example 1-6 | R-06 | P-06 (80) | — | Base-1 (1.10) | PGMEA (896) | CyHO (364) |
| Example 1-7 | R-07 | P-07 (80) | — | Base-1 (1.10) | PGMEA (896) | CyHO (364) |
| Example 1-8 | R-08 | P-08 (80) | — | Base-1 (1.10) | PGMEA (896) | CyHO (364) |
| Example 1-9 | R-09 | P-09 (80) | — | Base-1 (1.10) | PGMEA (896) | CyHO (364) |
| Example 1-10 | R-10 | P-10 (80) | — | Base-1 (1.10) | PGMEA (896) | CyHO (364) |
| Example 1-11 | R-11 | P-11 (80) | — | Base-1 (1.10) | PGMEA (896) | CyHO (364) |
| Example 1-12 | R-12 | P-12 (80) | — | Base-1 (1.10) | PGMEA (896) | CyHO (364) |
| Example 1-13 | R-13 | P-13 (80) | — | Base-1 (1.10) | PGMEA (896) | CyHO (364) |
| Example 1-14 | R-14 | P-14 (80) | — | Base-1 (1.10) | PGMEA (896) | CyHO (364) |
| Example 1-15 | R-15 | P-15 (80) | — | Base-1 (1.10) | PGMEA (896) | CyHO (364) |
| Example 1-16 | R-16 | P-16 (80) | — | Base-1 (1.10) | PGMEA (896) | CyHO (364) |
| Example 1-17 | R-17 | P-17 (80) | — | Base-1 (1.10) | PGMEA (896) | CyHO (364) |
| Example 1-18 | R-18 | P-18 (80) | — | Base-1 (1.10) | PGMEA (896) | CyHO (364) |
| Example 1-19 | R-19 | P-19 (80) | — | Base-1 (1.10) | PGMEA (896) | CyHO (364) |
| Example 1-20 | R-20 | P-20 (80) | — | Base-1 (1.10) | PGMEA (896) | CyHO (364) |
| Example 1-21 | R-21 | P-21 (80) | — | Base-1 (1.10) | PGMEA (896) | CyHO (364) |
| Example 1-22 | R-22 | P-22 (80) | — | Base-1 (1.10) | PGMEA (896) | CyHO (364) |
| Example 1-23 | R-23 | P-23 (80) | — | Base-1 (1.10) | PGMEA (896) | CyHO (364) |
| Example 1-24 | R-24 | P-24 (80) | PAG-1 (3.0) | Base-1 (1.10) | PGMEA (896) | CyHO (364) |
| Example 1-25 | R-25 | P-25 (80) | — | Base-1 (1.10) | PGMEA (896) | CyHO (364) |
| Example 1-26 | R-26 | P-34 (80) | — | Base-1 (1.10) | PGMEA (896) | EL (364) |
| Example 1-27 | R-27 | P-37 (80) | — | Base-1 (1.10) | PGMEA (896) | EL (364) |
| Example 1-28 | R-28 | P-38 (80) | — | Base-1 (1.10) | PGMEA (896) | EL (364) |
| Example 1-29 | R-29 | P-39 (80) | — | Base-1 (1.10) | PGMEA (896) | EL (364) |
| Example 1-30 | R-34 | P-44 (80) | — | Base-1 (1.10) | PGMEA (896) | CyHO (364) |
| Example 1-31 | R-35 | P-45 (80) | — | Base-1 (1.10) | PGMEA (896) | CyHO (364) |
| Example 1-32 | R-36 | P-46 (80) | — | Base-1 (1.10) | PGMEA (896) | EL (364) |
| Comparative Example 1-1 | R-30 | P-40 (80) | PAG-1 (6.5) | Base-1 (1.10) | PGMEA (896) | CyHO (364) |
| Comparative Example 1-2 | R-31 | P-41 (80) | — | Base-1 (1.10) | PGMEA (896) | CyHO (364) |
| Comparative Example 1-3 | R-32 | P-42 (80) | PAG-1 (6.5) | Base-1 (1.10) | PGMEA (896) | EL (364) |
| Comparative Example 1-4 | R-33 | P-43 (80) | PAG-1 (6.5) | Base-1 (1.10) | PGMEA (896) | EL (364) |

The acid generator, quencher (base) and solvent shown in Table 7 have the following meanings.
PAG-1: triphenylsulfonium nonafluorobutanesulfonate
Base-1: tri(2-methoxymethoxyethyl)amine
PGMEA: 1-methoxyisopropyl acetate
CyHO: cyclohexanone
EL: ethyl lactate
Surfactant 1: 3-methyl-3-(2,2,2-trifluoroethoxymethyl)oxetane/tetrahydrofuran/2,2-dimethyl-1,3-propane diol copolymer (Omnova Solutions, Inc.)

Evaluation of Resolution, Exposure Latitude and Line Width Roughness on ArF Lithography Examples 2-1 to 2-19 & Comparative Examples 2-1 to 2-2

On a silicon substrate, an antireflective coating solution (ARC-29A, Nissan Chemical Co., Ltd.) was coated and baked at 200° C. for 60 seconds to form an ARC of 78 nm thick. Each of inventive resist compositions (R-01 to 08, R-15 to 25) and comparative resist compositions (R-30 and 31) was spin coated on the ARC-coated silicon substrate and baked on a hot plate at 100° C. for 60 seconds, forming a resist film of 100 nm thick. The wafer was exposed by means of an ArF excimer laser scanner NSR-S307E (Nikon Corp., NA 0.85, 4/5 annular illumination, 6% halftone phase shift mask), post-exposure baked (PEB) at 100° C. for 60 seconds, and developed with a 2.38 wt % tetramethylammonium hydroxide aqueous solution for 60 seconds.

The optimum exposure (Eop) was defined as the exposure dose (mJ/cm$^2$) which provided a 1:1 resolution at the top and bottom of a 80-nm grouped line-and-space pattern. The maximum resolution of the resist was defined as the minimum line width (nm) of a line-and-space pattern that was resolved and separated at the optimum exposure. For the evaluation of exposure latitude, an exposure dose tolerance which provided a pattern size of 80 nm±10% when the exposure dose was changed from the optimum was determined, and the tolerance value was divided by the optimum dose and expressed in percent. A greater value indicates a smaller performance change with a change of exposure dose, that is, better exposure latitude. The line width roughness (LWR) of a 80-nm line-and-space pattern was measured using measurement SEM (S-9380 by Hitachi Hitechnologies, Ltd.).

TABLE 8

|  | Resist composition | Optimum exposure (mJ/cm$^2$) | Maximum resolution (nm) | Exposure latitude (%) | LWR (nm) |
|---|---|---|---|---|---|
| Example 2-1 | R-01 | 30 | 70 | 14.2 | 4.5 |
| Example 2-2 | R-02 | 32 | 70 | 13.5 | 4.4 |
| Example 2-3 | R-03 | 30 | 75 | 14.2 | 5.3 |
| Example 2-4 | R-04 | 34 | 75 | 13.7 | 5.4 |
| Example 2-5 | R-05 | 33 | 70 | 13.6 | 4.9 |
| Example 2-6 | R-06 | 33 | 75 | 14.5 | 4.2 |
| Example 2-7 | R-07 | 35 | 70 | 13.8 | 4.0 |
| Example 2-8 | R-08 | 31 | 75 | 15.0 | 5.1 |
| Example 2-9 | R-15 | 33 | 70 | 13.9 | 4.3 |
| Example 2-10 | R-16 | 31 | 75 | 14.2 | 5.5 |
| Example 2-11 | R-17 | 30 | 70 | 14.0 | 5.2 |
| Example 2-12 | R-18 | 32 | 75 | 13.6 | 5.3 |
| Example 2-13 | R-19 | 34 | 75 | 14.3 | 4.8 |
| Example 2-14 | R-20 | 36 | 70 | 14.1 | 5.0 |
| Example 2-15 | R-21 | 33 | 75 | 14.7 | 4.2 |
| Example 2-16 | R-22 | 30 | 70 | 13.8 | 4.1 |
| Example 2-17 | R-23 | 32 | 70 | 14.4 | 5.2 |
| Example 2-18 | R-24 | 32 | 75 | 13.5 | 4.5 |
| Example 2-19 | R-25 | 30 | 75 | 14.7 | 5.0 |
| Comparative Example 2-1 | R-30 | 30 | 80 | 12.1 | 7.4 |
| Comparative Example 2-2 | R-31 | 37 | 80 | 10.3 | 8.2 |

The data of Examples in Table 8 demonstrate that the inventive resist compositions exhibit good resolution performance, good exposure latitude and low LWR values when processed by ArF excimer laser lithography.

Evaluation of Resolution on EB Lithography

Examples 3-1 to 3-5 & Comparative Examples 3-1 to 3-2

On a 8-inch silicon wafer having an antireflective coating (DUV-42 by Brewer Science) of 610 Å thick coated thereon, each of the inventive resist compositions (R-26 to R-29, R-33) or comparative resist compositions (R-32 and R-33) was spin coated and heat treated at 100° C. for 60 seconds to form a resist film of 2,000 Å thick. Using an EB lithography system HL-800D (Hitachi Hitechnologies, Ltd.) at an accelerating voltage of 50 keV, exposure was performed on the resist film. The resist film was post-exposure baked (PEB) at 120° C. for 60 seconds and developed with a 2.38 wt % TMAH aqueous solution, obtaining a positive pattern.

The resist pattern was evaluated as follows. The optimum exposure (sensitivity, Eop) was defined as the exposure dose (μC/cm$^2$) which provided a 1:1 resolution at the top and bottom of a 120-nm line-and-space pattern. The resolution of the resist was defined as the minimum line width of a line-and-space pattern that was ascertained separate at the optimum exposure. The profile of the resolved resist pattern was evaluated by observing a cross section of the resist under a SEM.

The post-exposure delay (PED) in vacuum was evaluated by exposing the coated wafer on an EB lithography system, holding it in the vacuum system for 24 hours, thereafter effecting PEB and development. The size of lines of a 120-nm line-and-space pattern was measured and a percent change thereof was calculated. For example, when the line size increases by 12 nm, the change is reported as +10%. A smaller change indicates better stability. The test results are shown in Table 9.

TABLE 9

|  | Resist composition | Eop (μC/cm$^2$) | Resolution (nm) | Pattern profile | Line size change by PED |
|---|---|---|---|---|---|
| Example 3-1 | R-26 | 18 | 80 | Rectangular | 0 |
| Example 3-2 | R-27 | 20 | 80 | Rectangular | 0 |
| Example 3-3 | R-28 | 20 | 80 | Rectangular | 0 |
| Example 3-4 | R-29 | 18 | 80 | Rectangular | 0 |
| Example 3-5 | R-36 | 17 | 80 | Rectangular | 0 |
| Comparative Example 3-1 | R-32 | 25 | 100 | Somewhat rounded top | +10% |
| Comparative Example 3-2 | R-33 | 25 | 100 | Somewhat rounded top | +10% |

It is evident from Table 9 that the resist composition of the invention is also improved in resolution and vacuum PED when processed by EB lithography.

Evaluation of Sensitivity and Resolution on EUV Lithography

Examples 4-1 to 4-10 & Comparative Examples 4-1 to 4-2

On a silicon wafer treated with hexamethyldisilazane (HMDS), each of inventive resist compositions (R-01 to 05, 09 to 11, 34, 35) and comparative resist compositions (R-30 and 31) was spin coated and baked at 110° C. for 60 seconds, forming a resist film of 50 nm thick. The wafer was exposed by means of an EUV microstepper (NA 0.3, monopolar illumination), post-exposure baked (PEB) at 95° C. for 60 seconds, and developed with a 2.38 wt % tetramethylammonium hydroxide aqueous solution for 30 seconds, obtaining a positive pattern.

The optimum exposure (sensitivity, Eop) was defined as the exposure dose (mJ/cm$^2$) which provided a 1:1 resolution at the top and bottom of a 32-nm line-and-space pattern. The maximum resolution of the resist was defined as the minimum line width (nm) of a line-and-space pattern that was resolved and separated at the optimum exposure. The results are shown in Table 10.

TABLE 10

| | Resist composition | Eop (mJ/cm$^2$) | Resolution (nm) |
|---|---|---|---|
| Example 4-1 | R-01 | 17 | 26 |
| Example 4-2 | R-02 | 17 | 25 |
| Example 4-3 | R-03 | 18 | 25 |
| Example 4-4 | R-04 | 18 | 26 |
| Example 4-5 | R-05 | 18 | 26 |
| Example 4-6 | R-09 | 12 | 24 |
| Example 4-7 | R-10 | 12 | 24 |
| Example 4-8 | R-11 | 12 | 25 |
| Example 4-9 | R-34 | 11 | 24 |
| Example 4-10 | R-35 | 11 | 25 |
| Comparative Example 4-1 | R-30 | 26 | 32 |
| Comparative Example 4-2 | R-31 | 24 | 30 |

It is evident from Table 10 that the resist composition of the invention is also improved in sensitivity and resolution when processed by EUV lithography.

Japanese Patent Application No. 2008-219475 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A sulfonium salt having the general formula (1):

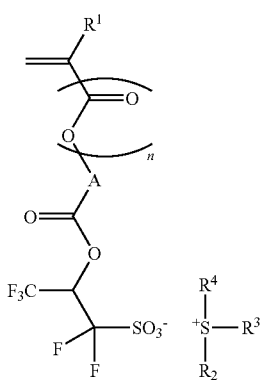

(1)

wherein R$^1$ is hydrogen, fluorine, methyl or trifluoromethyl, R$^2$, R$^3$ and R$^4$ are each independently a substituted or unsubstituted, straight or branched C$_1$-C$_{10}$ alkyl, alkenyl or oxoalkyl group or a substituted or unsubstituted C$_6$-C$_{18}$ aryl, aralkyl or aryloxoalkyl group, or at least two of R$^2$, R$^3$ and R$^4$ may bond together to form a ring with the sulfur atom to which they are attached, A is a divalent C$_1$-C$_{20}$ organic group which may contain a heteroatom, and n is 0 or 1.

2. A polymer capable of generating a sulfonic acid in response to high-energy radiation or heat, the sulfonic acid comprising recurring units of the general formula (1a):

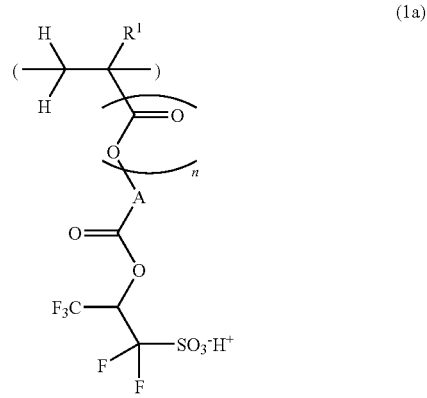

(1a)

wherein R$^1$ is hydrogen, fluorine, methyl or trifluoromethyl, A is a divalent C$_1$-C$_{20}$ organic group which may contain a heteroatom, and n is 0 or 1.

3. A polymer comprising recurring units of the general formula (1b):

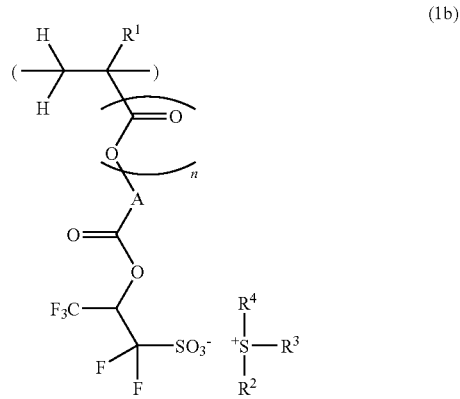

(1b)

wherein R$^1$ is hydrogen, fluorine, methyl or trifluoromethyl, R$^2$, R$^3$ and R$^4$ are each independently a substituted or unsubstituted, straight or branched C$_1$-C$_{10}$ alkyl, alkenyl or oxoalkyl group or a substituted or unsubstituted C$_6$-C$_{18}$ aryl, aralkyl or aryloxoalkyl group, or at least two of R$^2$, R$^3$ and R$^4$ may bond together to form a ring with the sulfur atom to which they are attached, A is a divalent C$_1$-C$_{20}$ organic group which may contain a heteroatom, and n is 0 or 1.

4. The polymer of claim 3, further comprising recurring units of at least one type selected from the general formulae (2) to (6):

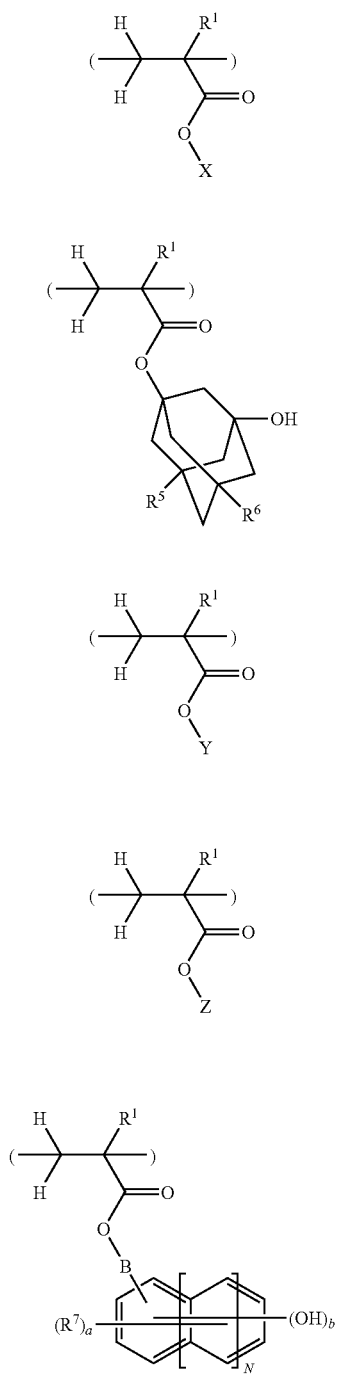

wherein R¹ is as defined above, R⁵ and R⁶ are each independently hydrogen or hydroxyl, X is an acid labile group, Y is a substituent group having lactone structure, Z is hydrogen, $C_1$-$C_{15}$ fluoroalkyl or $C_1$-$C_{15}$ fluoroalcohol-containing substituent group, N is an integer of 0 to 2, R⁷ is hydrogen or $C_1$-$C_{10}$ alkyl, B is a single bond or a divalent $C_1$-$C_{10}$ organic group which may have oxygen substituted thereon, a is an integer of 0 to 3, and b is an integer of 1 to 3.

5. The polymer of claim 3, further comprising recurring units of at least one type selected from the general formulae (7) to (11):

wherein R¹ and X are as defined above, and G is oxygen or carbonyloxy (—C(=O)O—).

6. A resist composition comprising the polymer of claim 3 as a base resin.

7. The resist composition of claim 6, further comprising a surfactant which is insoluble in water and soluble in an alkaline developer.

8. A pattern forming process comprising the steps of:
applying the resist composition of claim 6 onto a substrate to form a coating,
heat treating the coating and exposing it to high-energy radiation through a photomask,
optionally heat treating the exposed coating and developing it with a developer.

9. A pattern forming process comprising the steps of:
applying the resist composition of claim 6 onto a substrate to form a resist coating,
heat treating the resist coating,
applying onto the resist coating a protective coating which is insoluble in water and soluble in an alkaline developer, exposing the coated substrate to high-energy radiation from a projection lens through a photomask while holding water between the substrate and the projection lens, optionally heat treating the exposed coating and developing it with a developer.

10. A pattern forming process comprising the steps of applying the resist composition of claim 6 onto a substrate to form a coating, heat treating the coating, imagewise writing with an electron beam, heat treating the coating, and developing it with a developer.

11. A resist composition comprising the polymer of claim 3 and a polymer free of recurring units of formula (1b) as a base resin.

* * * * *